(12) United States Patent
Yeh et al.

(10) Patent No.: US 9,583,980 B2
(45) Date of Patent: Feb. 28, 2017

(54) MIDFIELD COUPLER

(71) Applicant: NeuSpera Medical Inc.

(72) Inventors: Alexander Jueshyan Yeh, Los Altos Hills, CA (US); Milton M. Morris, Houston, TX (US)

(73) Assignee: NeuSpera Medical Inc., San Jose, CA (US)

( * ) Notice: Subject to any disclaimer, the term of this patent is extended or adjusted under 35 U.S.C. 154(b) by 0 days.

(21) Appl. No.: 15/200,543

(22) Filed: Jul. 1, 2016

(65) Prior Publication Data

US 2016/0344240 A1 Nov. 24, 2016

Related U.S. Application Data

(63) Continuation of application No. PCT/US2015/030995, filed on May 15, 2015.

(51) Int. Cl.
| | | |
|---|---|---|
| *H01F 27/42* | (2006.01) |
| *H01F 37/00* | (2006.01) |
| *H01F 38/00* | (2006.01) |
| *A61N 1/378* | (2006.01) |
| *A61N 1/372* | (2006.01) |
| *A61B 18/18* | (2006.01) |

(52) U.S. Cl.
CPC ............. *H02J 50/20* (2016.02); *A61B 18/18* (2013.01); *A61N 1/3787* (2013.01); *A61N 1/37229* (2013.01); *H02J 50/12* (2016.02); *H02J 50/23* (2016.02); *A61B 2018/1838* (2013.01)

(58) Field of Classification Search
CPC ............ H02J 50/15; H02J 50/20; A61B 18/18
USPC .......................................................... 307/104
See application file for complete search history.

(56) References Cited

U.S. PATENT DOCUMENTS

| | | | |
|---|---|---|---|
| 5,324,316 | A | 6/1994 | Schulman et al. |
| 5,735,887 | A | 4/1998 | Barreras, Sr. et al. |
| 6,051,017 | A | 4/2000 | Loeb et al. |
| 6,061,596 | A | 5/2000 | Richmond et al. |

(Continued)

FOREIGN PATENT DOCUMENTS

| | | |
|---|---|---|
| CN | 105744986 A | 7/2016 |
| EP | 1171190 A1 | 1/2002 |

(Continued)

OTHER PUBLICATIONS

"International Application Serial No. PCT/US2015/030995, International Search Report mailed Oct. 16, 2015", 4 pgs.

(Continued)

*Primary Examiner* — Carlos Amaya
(74) *Attorney, Agent, or Firm* — Schwegman Lundberg & Woessner, P.A.

(57) ABSTRACT

Described herein are devices, systems, and methods for wireless power transfer utilizing a midfield source and implant. In one variation, a midfield source may be realized by a patterned metal plate composed of one of more sub-wavelength structures. These midfield sources may manipulate evanescent fields outside a material (e.g., tissue) to excite and control propagating fields inside the material (e.g., tissue) and thereby generate spatially confined and adaptive energy transport in the material (e.g., tissue). The energy may be received by an implanted device, which may be configured for one or more functions such as stimulation, sensing, or drug delivery.

11 Claims, 41 Drawing Sheets

(56) References Cited

U.S. PATENT DOCUMENTS

| | | |
|---|---|---|
| 6,175,764 B1 | 1/2001 | Loeb |
| 6,185,455 B1 | 2/2001 | Loeb |
| 6,201,453 B1 | 3/2001 | Chan |
| 6,214,032 B1 | 4/2001 | Loeb et al. |
| 6,360,750 B1 | 3/2002 | Gerber et al. |
| 6,473,652 B1 | 10/2002 | Sarwal et al. |
| 6,477,425 B1 | 11/2002 | Nowick et al. |
| 6,505,074 B2 | 1/2003 | Boveja et al. |
| 6,582,441 B1 | 6/2003 | He et al. |
| 6,650,943 B1 | 11/2003 | Whitehurst |
| 6,652,449 B1 | 11/2003 | Gross et al. |
| 6,709,385 B2 | 3/2004 | Forsell |
| 6,735,474 B1 | 5/2004 | Loeb et al. |
| 6,836,684 B1 | 12/2004 | Rijkhoff et al. |
| 6,953,429 B2 | 10/2005 | Forsell et al. |
| 6,990,376 B2 | 1/2006 | Tanaagho et al. |
| 7,027,860 B2 | 4/2006 | Bruninga et al. |
| 7,054,689 B1 | 5/2006 | Whitehurst et al. |
| 7,062,330 B1 | 6/2006 | Boveja et al. |
| 7,142,925 B1 | 11/2006 | Bhadra et al. |
| 7,191,007 B2 | 3/2007 | Desai et al. |
| 7,295,879 B2 | 11/2007 | Denker et al. |
| 7,330,756 B2 | 2/2008 | Marnfeldt |
| 7,351,921 B1 | 4/2008 | Haller |
| 7,499,753 B2 | 3/2009 | Forsell |
| 7,580,752 B2 | 8/2009 | Gerber et al. |
| 7,582,053 B2 | 9/2009 | Gross et al. |
| 7,599,744 B2 | 10/2009 | Giordano et al. |
| 7,621,863 B2 | 11/2009 | Forsell |
| 7,643,880 B2 | 1/2010 | Tanagho et al. |
| 7,647,112 B2 | 1/2010 | Tracey et al. |
| 7,706,892 B2 | 4/2010 | Colvin et al. |
| 7,763,034 B2 | 7/2010 | Siegel et al. |
| 7,781,683 B2 | 8/2010 | Haller et al. |
| 7,857,819 B2 | 12/2010 | Jaax et al. |
| 7,881,803 B2 | 2/2011 | Parramon et al. |
| 7,908,014 B2 | 3/2011 | Schulman et al. |
| 7,979,126 B2 | 7/2011 | Payne et al. |
| 7,979,140 B2 | 7/2011 | Schulman |
| 8,019,419 B1 | 9/2011 | Panescu et al. |
| 8,019,423 B2 | 9/2011 | Possover |
| 8,055,336 B1 | 11/2011 | Schulman et al. |
| 8,096,939 B2 | 1/2012 | Forsell |
| 8,175,716 B2 | 5/2012 | Rahman et al. |
| 8,214,048 B1 | 7/2012 | Whitehurst et al. |
| 8,369,963 B2 | 2/2013 | Parramon et al. |
| 8,386,048 B2 | 2/2013 | McClure et al. |
| 8,401,663 B2 | 3/2013 | Aghassian |
| 8,489,191 B2 | 7/2013 | Possover |
| 8,494,658 B2 | 7/2013 | Crowe et al. |
| 8,498,716 B2 | 7/2013 | Chen et al. |
| 8,504,138 B1 | 8/2013 | Pivonka et al. |
| 8,556,796 B2 | 10/2013 | Forsell |
| 8,585,617 B2 | 11/2013 | Mashiach et al. |
| 8,588,917 B2 | 11/2013 | Whitehurst et al. |
| 8,624,787 B2 | 1/2014 | Druyan et al. |
| 8,630,705 B2 | 1/2014 | Mann et al. |
| 8,634,928 B1 | 1/2014 | O'driscoll et al. |
| 8,639,342 B2 | 1/2014 | Possover |
| 8,655,451 B2 | 2/2014 | Klosterman et al. |
| 8,666,491 B2 | 3/2014 | Chen et al. |
| 8,774,912 B2 | 7/2014 | Gerber |
| 8,836,172 B2 | 9/2014 | Hamam et al. |
| 8,849,412 B2 | 9/2014 | Perryman et al. |
| 8,862,241 B2 | 10/2014 | Forsell |
| 8,874,217 B2 | 10/2014 | Alataris et al. |
| 8,886,321 B2 | 11/2014 | Rohrer et al. |
| 8,886,339 B2 | 11/2014 | Faltys et al. |
| 8,892,214 B2 | 11/2014 | Bonde et al. |
| 8,903,502 B2 | 12/2014 | Perryman et al. |
| 8,909,343 B2 | 12/2014 | Towe |
| 8,972,004 B2 | 3/2015 | Simon et al. |
| 8,983,612 B2 | 3/2015 | Fang et al. |
| 8,989,861 B2 | 3/2015 | Su et al. |
| 9,020,602 B2 | 4/2015 | Aghassian |
| 9,031,665 B2 | 5/2015 | Aghassian |
| 9,042,997 B2 | 5/2015 | Rahman et al. |
| 9,044,158 B2 | 6/2015 | Varahramyan et al. |
| 9,072,904 B2 | 7/2015 | Parramon et al. |
| 9,168,374 B2 | 10/2015 | Su |
| 9,192,764 B2 | 11/2015 | Rohrer et al. |
| 9,233,258 B2 | 1/2016 | Simon et al. |
| 9,242,106 B2 | 1/2016 | Klosterman et al. |
| 9,254,393 B2 | 2/2016 | Perryman et al. |
| 9,289,607 B2 | 3/2016 | Su et al. |
| 9,351,655 B2 | 5/2016 | McDonald et al. |
| 9,351,664 B2 | 5/2016 | Forsell |
| 9,352,150 B2 | 5/2016 | Stevenson |
| 9,352,158 B2 | 5/2016 | Lee et al. |
| 9,352,162 B2 | 5/2016 | Lamont et al. |
| D758,596 S | 6/2016 | Perryman et al. |
| 9,357,949 B2 | 6/2016 | Drew |
| 9,358,381 B2 | 6/2016 | Smon |
| 9,358,383 B2 | 6/2016 | Boyd et al. |
| 9,358,390 B2 | 6/2016 | Polefko et al. |
| 9,358,391 B2 | 6/2016 | Zhu et al. |
| 9,358,392 B2 | 6/2016 | Mashiach |
| 9,358,394 B2 | 6/2016 | Steinke et al. |
| 9,358,395 B2 | 6/2016 | Tweden et al. |
| 9,358,396 B2 | 6/2016 | Holley |
| 9,358,398 B2 | 6/2016 | Moffitt et al. |
| 9,358,399 B2 | 6/2016 | Carbunaru et al. |
| 9,359,449 B2 | 6/2016 | Deisseroth et al. |
| 9,364,658 B2 | 6/2016 | Wechter |
| 9,364,666 B2 | 6/2016 | Chen |
| 9,364,667 B1 | 6/2016 | Dinsmoor et al. |
| 9,364,668 B2 | 6/2016 | Marsh |
| 9,364,672 B2 | 6/2016 | Marnfeldt |
| 9,364,673 B2 | 6/2016 | Lamont et al. |
| 9,364,678 B2 | 6/2016 | Atanasoska et al. |
| 9,364,679 B2 | 6/2016 | John |
| 9,365,628 B2 | 6/2016 | Deisseroth et al. |
| 9,366,871 B2 | 6/2016 | Ghosh et al. |
| 9,368,710 B2 | 6/2016 | Wang et al. |
| 9,370,664 B2 | 6/2016 | Marnfeldt et al. |
| 9,375,563 B2 | 6/2016 | Govea |
| 9,375,567 B2 | 6/2016 | Fell |
| 9,375,571 B2 | 6/2016 | Errico et al. |
| 9,375,574 B2 | 6/2016 | Kaula et al. |
| 9,375,575 B2 | 6/2016 | Moffitt et al. |
| 9,381,342 B2 | 7/2016 | Barker |
| 9,381,346 B2 | 7/2016 | Lee et al. |
| 9,381,359 B2 | 7/2016 | Parramon et al. |
| 9,381,360 B2 | 7/2016 | Hershey |
| 9,381,364 B2 | 7/2016 | Rahman et al. |
| 9,381,367 B2 | 7/2016 | Janzig |
| 9,387,322 B2 | 7/2016 | Bhadra et al. |
| 9,387,326 B2 | 7/2016 | Moffitt |
| 9,387,327 B2 | 7/2016 | Alataris et al. |
| 9,387,328 B2 | 7/2016 | Lee |
| 9,387,334 B2 | 7/2016 | Lee et al. |
| 9,387,338 B2 | 7/2016 | Burnett |
| 9,392,955 B2 | 7/2016 | Folkerts et al. |
| 9,393,396 B2 | 7/2016 | Peyman |
| 9,393,421 B2 | 7/2016 | Carbunaru et al. |
| 9,393,422 B2 | 7/2016 | Moffitt et al. |
| 9,393,423 B2 | 7/2016 | Parramon et al. |
| 9,393,433 B2 | 7/2016 | Parramon et al. |
| 9,393,435 B2 | 7/2016 | Mashiach |
| 9,394,347 B2 | 7/2016 | Deisseroth et al. |
| 9,397,639 B2 | 7/2016 | Feldman et al. |
| 9,398,901 B2 | 7/2016 | Tischendorf et al. |
| 9,399,130 B2 | 7/2016 | Bonde et al. |
| 9,399,131 B2 | 7/2016 | DiGiore et al. |
| 9,399,132 B2 | 7/2016 | Parramon et al. |
| 9,399,134 B2 | 7/2016 | Simon et al. |
| 9,401,625 B2 | 7/2016 | Zottola et al. |
| 2002/0055779 A1 | 5/2002 | Andrews |
| 2003/0009201 A1 | 1/2003 | Forsell |
| 2003/0169207 A1 | 9/2003 | Beigel |
| 2004/0049240 A1 | 3/2004 | Gerber et al. |
| 2004/0055610 A1 | 3/2004 | Forsell |
| 2004/0138725 A1 | 7/2004 | Forsell |
| 2004/0193229 A1 | 9/2004 | Starkebaum et al. |

(56) References Cited

U.S. PATENT DOCUMENTS

| | | |
|---|---|---|
| 2004/0250820 A1 | 12/2004 | Forsell |
| 2005/0055063 A1 | 3/2005 | Loeb et al. |
| 2005/0113878 A1 | 5/2005 | Gerber |
| 2005/0283202 A1 | 12/2005 | Gellman |
| 2006/0149333 A1 | 7/2006 | Tanagho et al. |
| 2006/0155347 A1 | 7/2006 | Forsell |
| 2006/0161204 A1 | 7/2006 | Colvin et al. |
| 2006/0161225 A1 | 7/2006 | Sormann et al. |
| 2007/0055324 A1 | 3/2007 | Thompson et al. |
| 2007/0060955 A1 | 3/2007 | Strother et al. |
| 2007/0191908 A1 | 8/2007 | Jacob et al. |
| 2007/0282378 A1 | 12/2007 | Huang et al. |
| 2008/0039904 A1 | 2/2008 | Bulkes et al. |
| 2008/0077184 A1 | 3/2008 | Denker et al. |
| 2008/0188917 A1 | 8/2008 | Gerber et al. |
| 2008/0275524 A1 | 11/2008 | Furness et al. |
| 2009/0058361 A1 | 3/2009 | John |
| 2009/0069869 A1 | 3/2009 | Stouffer et al. |
| 2009/0157145 A1 | 6/2009 | Cauller |
| 2009/0247817 A1 | 10/2009 | Forsell |
| 2009/0254144 A1 | 10/2009 | Bhadra et al. |
| 2010/0241195 A1 | 9/2010 | Meadows et al. |
| 2010/0286734 A1 | 11/2010 | Yun et al. |
| 2010/0292629 A1 | 11/2010 | Dacey, Jr. et al. |
| 2011/0071590 A1 | 3/2011 | Mounaim et al. |
| 2011/0093036 A1 | 4/2011 | Mashiach |
| 2011/0172733 A1 | 7/2011 | Lima et al. |
| 2011/0245892 A1 | 10/2011 | Kast et al. |
| 2012/0010680 A1 | 1/2012 | Wei et al. |
| 2012/0095531 A1 | 4/2012 | Derbas et al. |
| 2012/0101874 A1 | 4/2012 | Ben-Haim et al. |
| 2012/0136413 A1 | 5/2012 | Bonde et al. |
| 2012/0197342 A1* | 8/2012 | Towe ............ A61N 1/06 607/45 |
| 2012/0203218 A1 | 8/2012 | Bonn |
| 2012/0203306 A1 | 8/2012 | Sarvazyan et al. |
| 2012/0235502 A1 | 9/2012 | Kesler et al. |
| 2012/0283800 A1 | 11/2012 | Perryman et al. |
| 2012/0316622 A1 | 12/2012 | Whitehurst et al. |
| 2013/0053767 A1 | 2/2013 | Pivonka et al. |
| 2013/0110201 A1 | 5/2013 | Bonde et al. |
| 2013/0165996 A1 | 6/2013 | Meadows et al. |
| 2013/0181517 A1 | 7/2013 | Maguire |
| 2013/0215979 A1 | 8/2013 | Yakovlev et al. |
| 2013/0261692 A1 | 10/2013 | Cardinal et al. |
| 2013/0274829 A1 | 10/2013 | Gupta et al. |
| 2013/0289446 A1 | 10/2013 | Stone et al. |
| 2013/0289647 A1 | 10/2013 | Bhadra et al. |
| 2014/0163580 A1 | 6/2014 | Tischendorf et al. |
| 2014/0163644 A1 | 6/2014 | Scott et al. |
| 2014/0180365 A1 | 6/2014 | Perryman et al. |
| 2014/0257268 A1 | 9/2014 | Sachs et al. |
| 2014/0350041 A1 | 11/2014 | Yun et al. |
| 2014/0350633 A1 | 11/2014 | Gustafson et al. |
| 2015/0134026 A1 | 5/2015 | Kaula et al. |
| 2015/0134028 A1 | 5/2015 | Kaula et al. |
| 2015/0157389 A1 | 6/2015 | Ben-Ezra et al. |
| 2015/0224323 A1 | 8/2015 | Chen et al. |
| 2015/0249344 A1 | 9/2015 | Poon et al. |
| 2015/0321017 A1 | 11/2015 | Perryman et al. |
| 2015/0335285 A1 | 11/2015 | Poon et al. |
| 2016/0023003 A1 | 1/2016 | Perryman et al. |
| 2016/0023005 A1 | 1/2016 | Perryman et al. |
| 2016/0151628 A1 | 6/2016 | Simon et al. |
| 2016/0151633 A1 | 6/2016 | Goetz et al. |
| 2016/0151639 A1 | 6/2016 | Scharf et al. |
| 2016/0158051 A1 | 6/2016 | Mische |
| 2016/0158542 A1 | 6/2016 | Ahmed |
| 2016/0158549 A1 | 6/2016 | Woods et al. |
| 2016/0158553 A1 | 6/2016 | Panken et al. |
| 2016/0158558 A1 | 6/2016 | Shanahan et al. |
| 2016/0158564 A1 | 6/2016 | Rao et al. |
| 2016/0158565 A1 | 6/2016 | Lee |
| 2016/0158566 A1 | 6/2016 | Thacker et al. |
| 2016/0166203 A1 | 6/2016 | Goldstein |
| 2016/0166326 A1 | 6/2016 | Bakker et al. |
| 2016/0166829 A1 | 6/2016 | Pianca et al. |
| 2016/0166833 A1 | 6/2016 | Oh et al. |
| 2016/0166841 A1 | 6/2016 | Ostroff |
| 2016/0175583 A1 | 6/2016 | Kveen et al. |
| 2016/0175607 A1 | 6/2016 | Deisseroth et al. |
| 2016/0183842 A1 | 6/2016 | Najafi |
| 2016/0184179 A1 | 6/2016 | Asfora |
| 2016/0184591 A1 | 6/2016 | Feldman et al. |
| 2016/0184592 A1 | 6/2016 | Marnfeldt et al. |
| 2016/0184597 A1 | 6/2016 | Andresen et al. |
| 2016/0190698 A1 | 6/2016 | Andresen et al. |
| 2016/0193466 A1 | 7/2016 | Burnett |
| 2016/0193469 A1 | 7/2016 | Cardinal et al. |
| 2016/0193472 A1 | 7/2016 | Ozawa et al. |
| 2016/0199096 A1 | 7/2016 | Gardanier et al. |
| 2016/0199657 A1 | 7/2016 | Jiang et al. |
| 2016/0199658 A1 | 7/2016 | Nassif et al. |
| 2016/0199659 A1 | 7/2016 | Jiang et al. |
| 2016/0199660 A1 | 7/2016 | Rao et al. |
| 2016/0203187 A1 | 7/2016 | Alonso et al. |
| 2016/0206457 A1 | 7/2016 | Wong et al. |
| 2016/0206876 A1 | 7/2016 | Rajguru et al. |
| 2016/0206881 A1 | 7/2016 | Libbus |
| 2016/0213914 A1 | 7/2016 | He et al. |
| 2016/0213930 A1 | 7/2016 | Walker et al. |
| 2016/0213932 A1 | 7/2016 | Lee |
| 2016/0216768 A1 | 7/2016 | Goetz et al. |
| 2016/0216769 A1 | 7/2016 | Goetz et al. |
| 2016/0220828 A1 | 8/2016 | Poon et al. |
| 2016/0303385 A1 | 10/2016 | Poon et al. |
| 2016/0303386 A1 | 10/2016 | Poon et al. |
| 2016/0336813 A1 | 11/2016 | Yeh et al. |
| 2016/0339256 A1 | 11/2016 | Poon et al. |
| 2016/0344238 A1 | 11/2016 | Yeh et al. |

FOREIGN PATENT DOCUMENTS

| | | |
|---|---|---|
| EP | 1121046 B1 | 10/2004 |
| EP | 0802816 B1 | 5/2005 |
| EP | 1119314 B1 | 6/2006 |
| EP | 1600193 B1 | 8/2006 |
| EP | 1587463 B1 | 3/2007 |
| EP | 1587464 B1 | 8/2007 |
| EP | 1587465 B1 | 11/2007 |
| EP | 1217972 B1 | 12/2007 |
| EP | 1545702 B1 | 2/2008 |
| EP | 1911490 A1 | 4/2008 |
| EP | 1545695 B1 | 8/2008 |
| EP | 1702587 B1 | 12/2008 |
| EP | 1171190 B1 | 5/2011 |
| EP | 2247338 B1 | 8/2012 |
| EP | 2389975 B1 | 8/2012 |
| EP | 1904173 B8 | 12/2015 |
| EP | 2155062 B1 | 6/2016 |
| EP | 2211977 B1 | 6/2016 |
| EP | 2498872 B1 | 6/2016 |
| EP | 2914169 A4 | 6/2016 |
| EP | 3024540 A1 | 6/2016 |
| EP | 3030310 A1 | 6/2016 |
| EP | 3033147 A1 | 6/2016 |
| EP | 3037129 A1 | 6/2016 |
| EP | 2016083443 A1 | 6/2016 |
| EP | 2016090175 A1 | 6/2016 |
| EP | 2016090196 A1 | 6/2016 |
| EP | 2167189 B1 | 7/2016 |
| EP | 2195239 B1 | 7/2016 |
| EP | 2370172 B1 | 7/2016 |
| EP | 2658606 B1 | 7/2016 |
| EP | 2734268 B1 | 7/2016 |
| EP | 3038704 A1 | 7/2016 |
| EP | 3041565 A1 | 7/2016 |
| EP | 3041566 A1 | 7/2016 |
| EP | 3041567 A1 | 7/2016 |
| EP | 3041570 A1 | 7/2016 |
| EP | 3041571 A1 | 7/2016 |
| EP | 3042695 A1 | 7/2016 |
| EP | 3046621 | 7/2016 |
| EP | 3046621 A1 | 7/2016 |

(56) References Cited

FOREIGN PATENT DOCUMENTS

| EP | 3047874 A1 | 7/2016 |
|---|---|---|
| WO | WO-2008080073 A2 | 7/2008 |
| WO | WO-2011150430 A2 | 12/2011 |
| WO | WO-2014071079 A1 | 5/2014 |
| WO | WO-2014205407 A2 | 12/2014 |
| WO | WO-2015039108 A2 | 3/2015 |
| WO | WO-2015039108 A3 | 3/2015 |
| WO | WO-2015196164 A2 | 6/2015 |
| WO | WO-2015139053 A1 | 9/2015 |
| WO | WO-2015179225 A1 | 11/2015 |
| WO | 2015196164 A2 | 12/2015 |
| WO | WO-2016028608 A1 | 2/2016 |
| WO | WO-2016029159 A2 | 2/2016 |
| WO | WO-2016083460 A1 | 6/2016 |
| WO | WO-2016083465 A1 | 6/2016 |
| WO | WO-2016094269 A1 | 6/2016 |
| WO | WO-2016103245 A1 | 6/2016 |
| WO | WO-2016109833 A1 | 7/2016 |
| WO | WO-2016109836 A2 | 7/2016 |
| WO | WO-2016112398 A1 | 7/2016 |
| WO | WO-2016112400 A1 | 7/2016 |
| WO | WO-2016112401 A1 | 7/2016 |
| WO | WO-2016114923 A1 | 7/2016 |
| WO | WO-2016115031 A2 | 7/2016 |
| WO | WO-2016118943 A2 | 7/2016 |

OTHER PUBLICATIONS

"International Application Serial No. PCT/US2015/030995, Invitation to Pay Add'l Fees and Partial Search Rpt mailed Aug. 12, 2015", 2 pgs.
"International Application Serial No. PCT/US2015/030995, Written Opinion mailed Oct. 16, 2015", 6 pgs.
"U.S. Appl. No. 15/208,108, Preliminary Amendment filed Aug. 5, 2016", 7 pgs.
"U.S. Appl. No. 15/208,155, Preliminary Amendment filed Aug. 5, 2016", 9 pgs.
"International Application Serial No. PCT/US2014/055885, International Preliminary Report on Patentability mailed Mar. 31, 2016", 9 pgs.
"International Application Serial No. PCT/US2014/055885, International Search Report mailed Mar. 5, 2015", 5 pgs.
"International Application Serial No. PCT/US2014/055885, Written Opinion mailed Mar. 5, 2015", 7 pgs.
Aubert, Nerve, "RFID Technology for Human Implant Devices Technologie RFID pour implants dans le corps humain", Comptes rendus á l'Académie des Sciences (Special issue on nanosciences/nanotechnologies), (Mar. 1, 2011), 18 pgs.
Ho, John S., et al., "Midfield Wireless Powering for Implantable Systems", Proceedings of the IEEE. vol. 101, No. 6, [Online] retrieved from the internet: <URL:http://web.stanford.edu/group/poongroup/cgi-bin/wordpress/wp-content/uploads/2013/05/PIEEE%202013%20Ho.pdf>, (Apr. 4, 2013), 1-10.
Kim, Sanghoek, et al., "MidfieldWireless Powering of Subwavelength Autonomous Devices", Physical Review Letters, vol. 110, (May 17, 2013), 203905-1-203905-5.
Occhiuzzi, Cecilia, et al., "Human Body Sensing: a Pervasive Approach by Implanted RFID Tags", 3rd International Symposium on Applied Sciences in Biomedical and Communication Technologies (ISABEL), (Jan. 28, 2011), 5 pgs.
Park, Sung, et al., "Enhancement of wireless power transmission into biological tissues using a high surface impedance ground plane", Progress in Electromagnetics Research. vol. 135, [Online] retrieved from the internet: <URL:http://onlinewww.jpier.org/PIER/pier135/08.1211902.pdf>, (Dec. 12, 2012), 123-136.

Radiom, Soheil, et al., "Far-field RF Powering System for RFID and Implantable Devices with Monolithically Integrated On-Chip Antenna", IEEE Radio Frequency Integrated Circuits Symposium (RFIC), (Jun. 3, 2010), 4 pgs.
Thomas, Stewart, et al., "Modulated backscatter for ultra-low power uplinks from wearable and implantable devices", MedCOMM '12 Proceedings of the 2012 ACM workshop on Medical communication systems, (2012), 1-6.
Yeager, Daniel et al., "A 9 UA, Addressable Gen2 Sensor Tag for Biosignal Acquisition", IEEE Journal of Solid-State Circuits, 45(10), Oct. 2010), 2198-2009.
"U.S. Appl. No. 13/734,772, File History from Jan. 4, 2013 to Jan. 4, 2016", 213 pgs.
"U.S. Appl. No. 14/424,303, Preliminary Amendment filed Jan. 14, 2016", 4 pgs.
"U.S. Appl. No. 15/022,374, Non Final Office Action mailed Sep. 8, 2016", 17 pgs.
"U.S. Appl. No. 15/196,814, First Action Interview—Pre-Interview Communication mailed Sep. 8, 2016", 4 pgs.
"U.S. Appl. No. 15/196,874, First Action Interview—Pre-Interview Communication mailed Sep. 8, 2016", 4 pgs.
"U.S. Appl. No. 15/196,991, First Action Interview—Pre-Interview Communication mailed Sep. 1, 2016", 5 pgs.
"International Application Serial No. PCT/US2014/055885, Invitation to Pay Additional fees mailed Jan. 5, 2015", 2 pgs.
Giamalaki, M. I, et al., "Focused microwave radiometry from a possible functional imaging perspective: theoretical optimization of the properties of a microwave radiometry system", Journal of Instrumentation 4(05), (May 2009), 8 pgs.
Ho, John S, et al., "MidfieldWireless Powering for Implantable Systems", Proceedings of tho IEEE; 101(6), (Jun. 2013), 1369-1378.
Ho, John S, "Planar immersion lens with metasurfaces", Physical Review B. vol. 91, (Mar. 30, 2015), 11 pgs.
Ho, John S, et al., "Wireless power transfer to deep-tissue microimplants". Proceedings of the National Academy of Sciences of the United States of America; 111(22), (Jun. 3, 2014), 7974-7979.
Khaleghi, Ali, et al., "On the Use of a Dielectric Matching Layer for Ultra Wideband Medical Applications", Proceedings of the 7th International Conference on Body Area Networks, (Feb. 2012), 8 pgs.
Maccarini, Paolo, "Modeling the detectability of vesicoureteral reflux using microwave radiometry", Journal of Physics in Medicine and Biology; 55(18), (Sep. 2010), 5417-5435.
U.S. Appl. No. 15/022,374, filed Mar. 16, 2016, Multi-Element Coupler for Generation of Electromagnetic Energy.
U.S. Appl. No. 15/196,814, filed Jun. 29, 2016, Multi-Element Coupler for Generation of Electromagnetic Energy.
U.S. Appl. No. 15/196,874, filed Jun. 29, 2016, Multi-Element Coupler for Generation of Electromagnetic Energy.
U.S. Appl. No. 15/196,991, filed Jun. 29, 2016, Multi-Element Coupler for Generation of Electromagnetic Energy.
U.S. Appl. No. 15/208,108, filed Jul. 12, 2016, Midfield Coupler.
U.S. Appl. No. 15/208,155, filed Jul. 12, 2016, Midfield Coupler.
"European Application Serial No. 14843943.3, Preliminary Amendment filed Dec. 1, 2016", 12 pgs.
"U.S. Appl. No. 15/022,374, Respons filed Dec. 8, 2016 to Non Final Office Action mailed Sep. 8, 2016", 19 pgs.
"U.S. Appl. No. 15/022,374, Response filed Dec. 8, 2016 to Non Final Office Action mailed Sep. 8, 2016", 19 pgs.
"U.S. Appl. No. 15/196,814, Response filed Nov. 14, 2016 to First Action Interview—Office Action Summary mailed Oct. 17, 2016", 10 pgs.
"U.S. Appl. No. 15/208,155, Corrected Notice of Allowance mailed Nov. 10, 2016", 2 pgs.

* cited by examiner

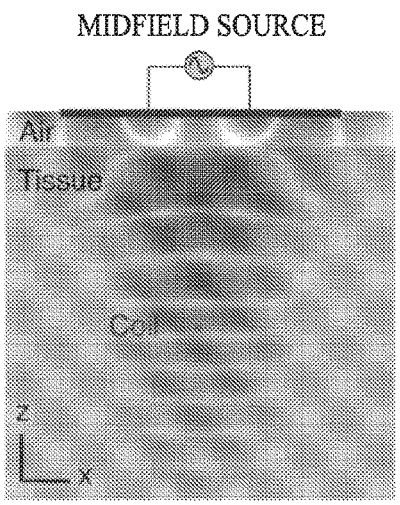 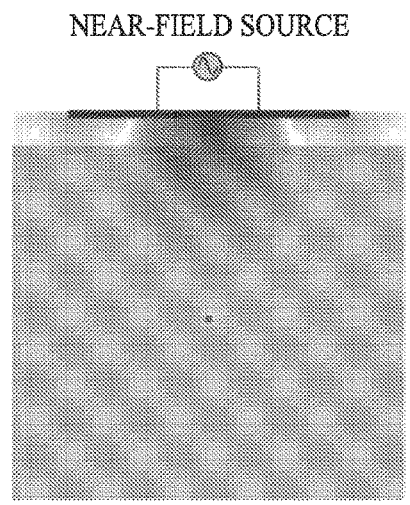
FIG. 3A  FIG. 3B
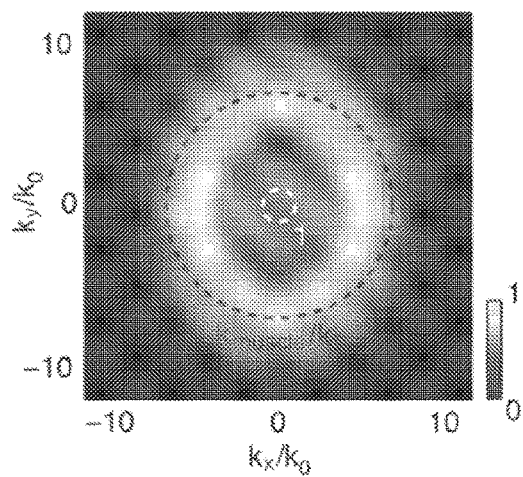 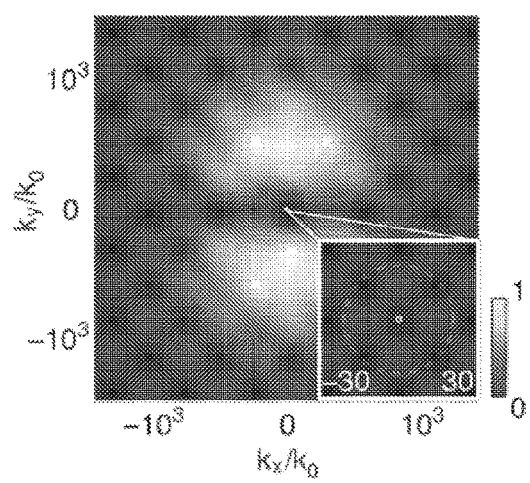
FIG. 3C  FIG. 3D

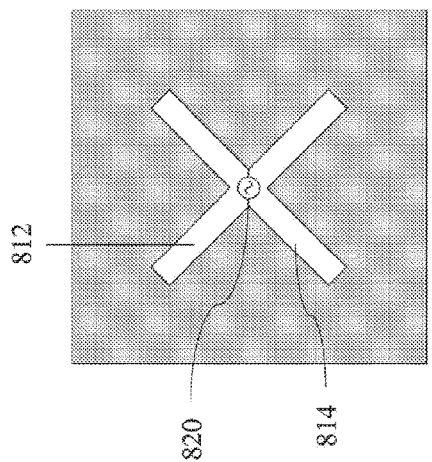
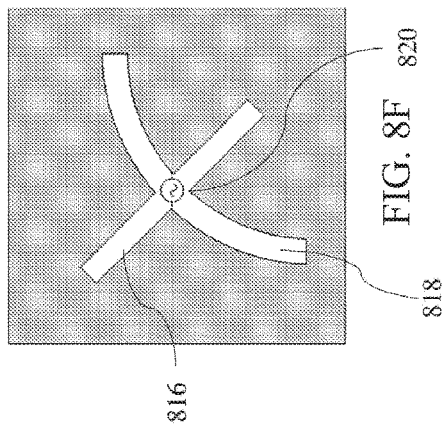
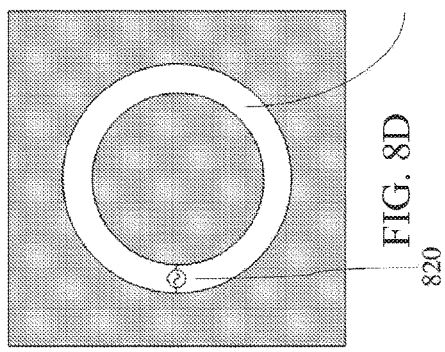
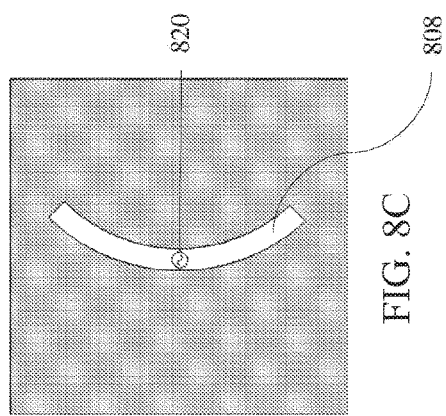
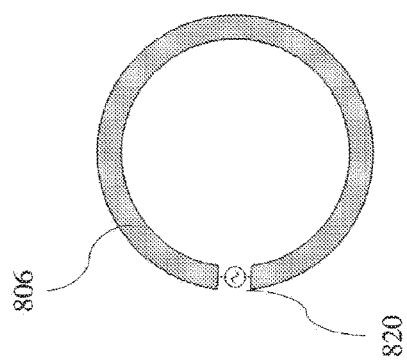
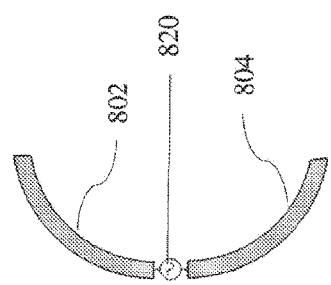

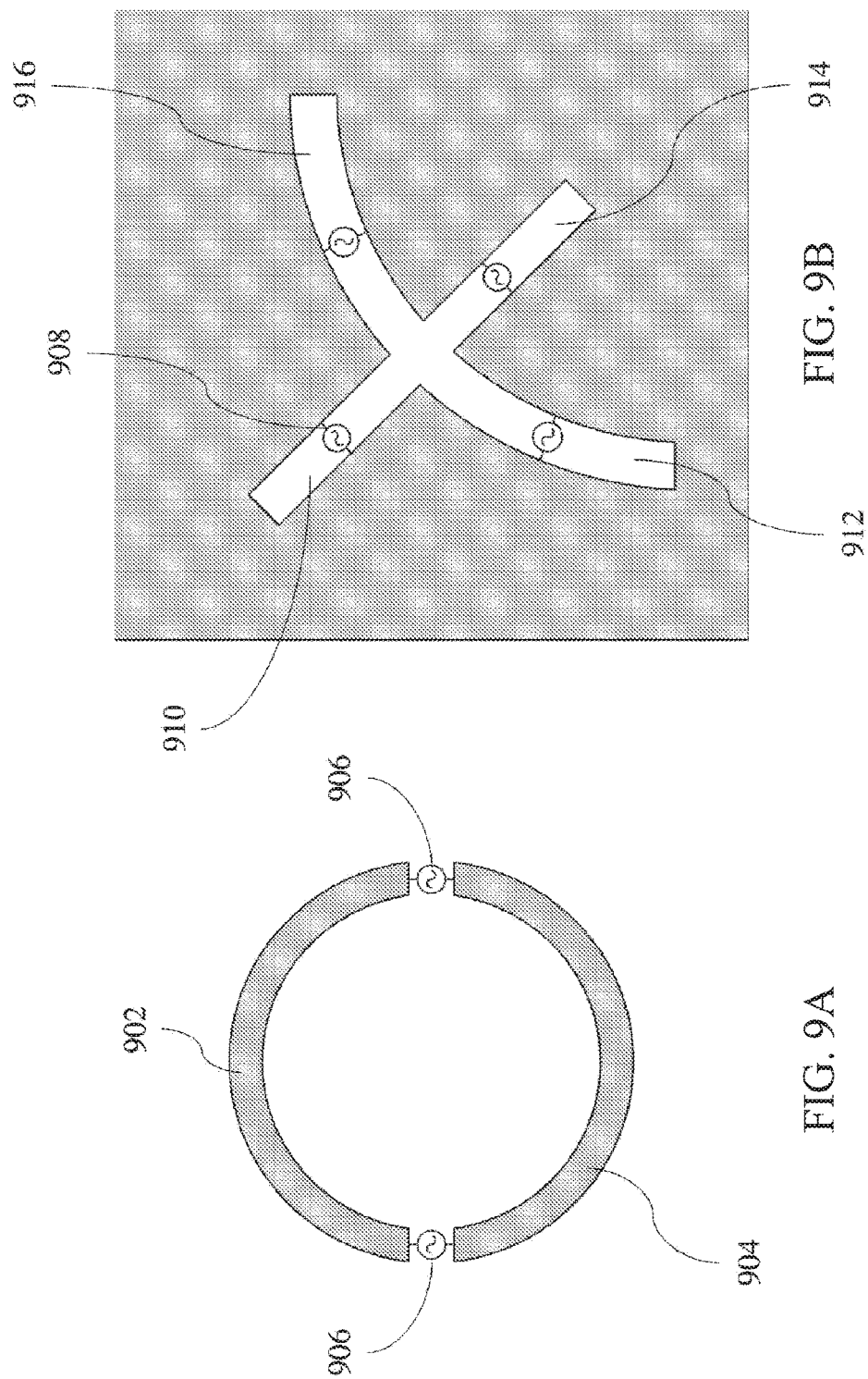

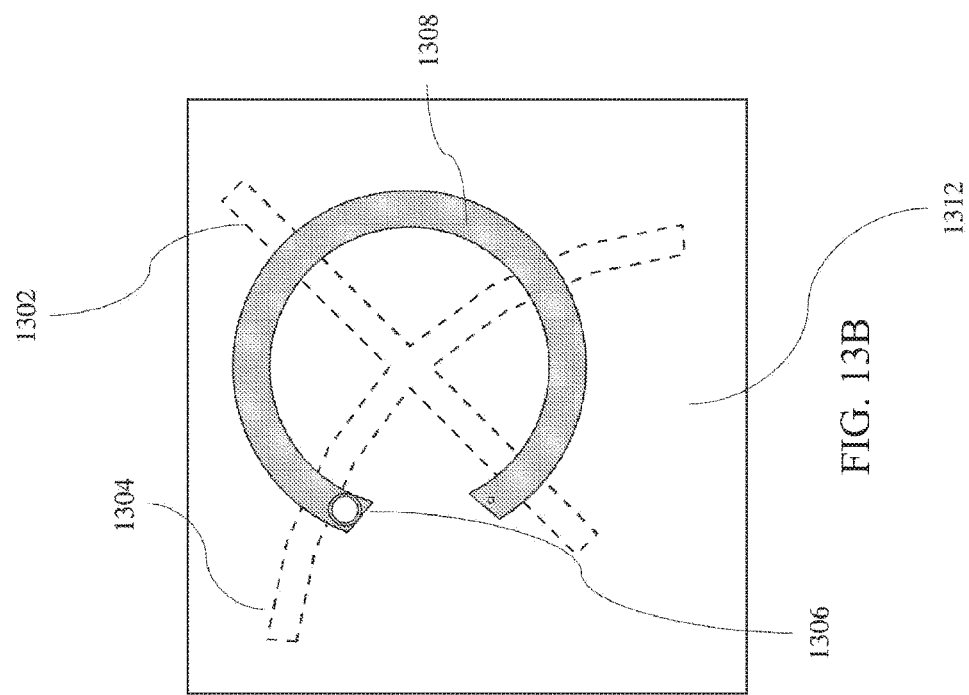
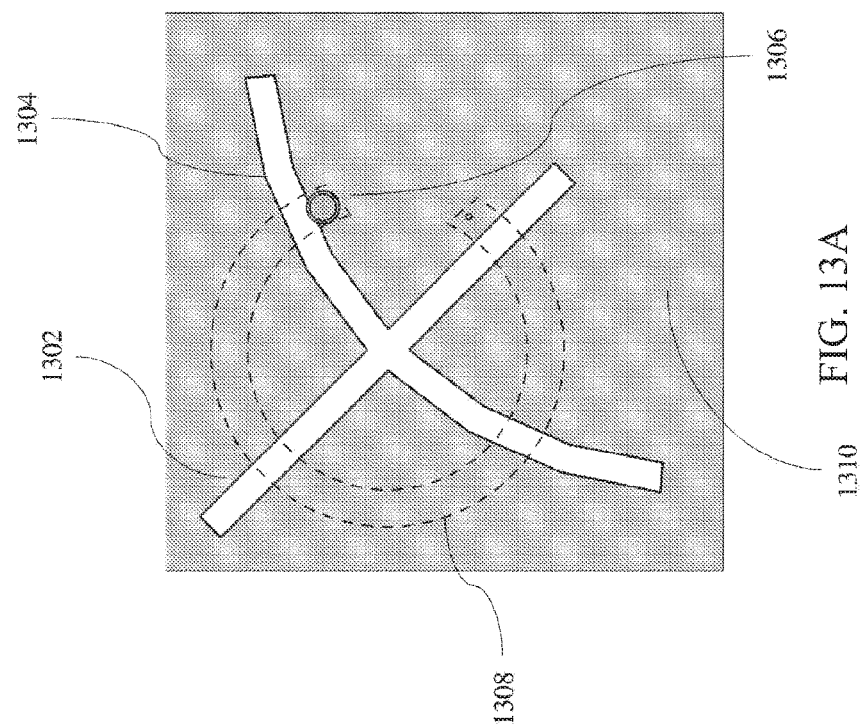
FIG. 13A
FIG. 13B

YZ PLANE　　　XZ PLANE

YZ PLANE　　　XZ PLANE

YZ PLANE         XZ PLANE

YZ PLANE         XZ PLANE

ADAPTIVE

NON-ADAPTIVE

MIDFIELD COUPLER

RELATED APPLICATION

This application is a continuation under 35 U.S.C. §1.111(a) of PCT Application Serial Number PCT/US2015/030995, filed May 15, 2015, and titled "MIDFIELD COUPLER", which is incorporated herein by reference in its entirety.

FIELD

This disclosure is generally related to wireless power transfer. More specifically, described herein are devices, systems, and methods for midfield coupling to an implanted device, such as a microstimulator, sensor, ablation, or drug delivery device.

BACKGROUND

Although considerable progress has been made in energy storage technologies, batteries remain a major obstacle to miniaturization of implantable electronics. As a result, current implantable electrical stimulation systems typically include a large impulse generator containing a titanium case enclosing the battery and circuitry used to generate the electrical pulses. The impulse generator is typically implanted within a cavity in the body such as under the clavicle, below the rib cage, in the lower abdominal region, or in the upper buttock. Electrical pulses are then delivered to a targeted nerve or muscle region via leads routed underneath the skin or through a blood vessel. Problems associated with this current approach include pocket infections, lead dislodgment, lead fracture or perforation, muscle tear due to implanting in or pulling out the leads, and limited locations for the placement of the electrodes. In addition, the lifetime of these devices is burdensomely limited, requiring periodic surgical replacement once the battery unit is depleted.

Alternatively, energy can be wirelessly transferred from an external source, but the ability to transfer power to small implanted devices and/or devices located beyond superficial depths remains challenging. Most of the known wireless powering methods for implantable electronics are based on the near-field coupling method, and these and other suggested methods suffer from a number of disadvantages. The power harvesting structure in the implanted device (e.g., the coil(s) or antenna(s)) is typically large. The largest dimension is typically on the order of a centimeter or larger. The coils external to the body in near-field coupling methods are also typically bulky and inflexible. This presents some difficulties with regard to the incorporation of the external device into daily life. The intrinsic exponential decay of the near field limits miniaturization of the implanted device beyond superficial depths (greater than 1 cm). On the other hand, the radiative nature of the far field severely limits the energy transfer efficiency. It may therefore be desirable to have devices and methods for transmitting wireless power to small implantable devices, and corresponding small implantable devices suitable for less invasive delivery methods.

BRIEF SUMMARY

Described herein are devices, systems, and methods for wireless power transfer utilizing a midfield source and implant. In one variation, a midfield source (coupler) may be realized by a patterned metal plate composed of one of more subwavelength structures. These midfield sources may manipulate evanescent fields outside a material (e.g., tissue) to excite and control propagating fields inside the material and thereby generate spatially confined and adaptive energy transport in the material. The energy may be received by an implanted device, which may be configured for one or more functions such as stimulation, ablation, sensing, or drug delivery, among other functions.

In one variation, the devices described herein are midfield sources. The midfield sources may comprise a midfield plate and one or more excitation ports. The midfield plate may comprise a planar surface and one or more subwavelength structures. The midfield source may be configured for wireless power transmission through tissue. In some variations, the midfield source comprises a planar structure comprising a metal, at least one of a slot or metal strip, and an excitation port coupled to the slot or metal strip, wherein the source is capable of generating an electromagnetic field with a spatial frequency spectrum of the field adjacent to the source having non-negligible components that lie in the range of $$k_0 \leq \sqrt{k_x^2 + k_y^2} < k_{muscle}.$$

In some of these variations, the device comprises at least two slots or at least two metal strips. In some of these variations, the two slots or two metal strips are excited by the same excitation port. In some of these variations the two slots or two metal strips are excited by the same excitation port using a microstrip transmission line. In some variations, the device further comprises a controller for dynamically shifting a focal region of the electromagnetic field. In some variations, the device comprises eight slots, wherein the eight slots are arranged in pairs of an intersecting linear slot and curved slot. In some of these variations, each pair of slots is excited by a single excitation port.

Also described herein are systems for wirelessly powering an implant through tissue. In some variations, the systems may comprise a midfield source comprising a midfield plate comprising a planar structure and a subwavelength structure, and an excitation port for exciting the subwavelength structure, and an implant comprising a receiver coil, wherein the midfield source is configured to transmit power to the implant through propagating modes of the tissue. In some of these variations, the source is capable of generating an electromagnetic field with a spatial frequency spectrum of the field adjacent to the source having non-negligible components that lie in the range of $$k_0 \leq \sqrt{k_x^2 + k_y^2} < k_{muscle}.$$

In some of these variations, the midfield plate comprises a flexible substrate. In some of these variations, the flexible substrate comprises an adhesive and is configured to be attached to a patient's skin. In some of these variations, the diameter of the implant is less than 3 mm. In some of these variations, the implant comprises an electrode. In some variations, the implant comprises a sensor. In some variations, the midfield source comprises a controller for dynamically shifting a focal region of the electromagnetic field in response to feedback from the sensor.

Also described herein are methods for wireless transmitting power to an implant through a material. In some variations, the method comprises generating an electromagnetic field with a source, and wirelessly transferring energy to a receiver coil of the implant through the material, wherein the spatial frequency spectrum of the field adjacent to the source comprises non-negligible components that lie in the range of $$k_0 \leq \sqrt{k_x^2 + k_y^2} < k_{muscle}.$$

In some variations, the source and the implant are at least 5 cm apart, and the implant has a diameter of less than 3 mm. In some of these variations, the power transfer to the coil is at least 10 µW when 500 mW are coupled into the material. In some variations, the method further comprises wirelessly transferring energy to a second receiver coil of a second implant. In some variations, the method further comprises adjusting a focal region of the electromagnetic field.

Also described herein are wireless power systems comprising a source comprising one or more subwavelength structures configured to wirelessly transmit power by manipulating evanescent fields outside of tissue to generate a spatially focused field in the tissue, an implant configured to receive the wireless power from the external module, the implant comprising at least one sensor or stimulator. In some variations, the sensor is selected from the group consisting of a thermal sensor, a chemical sensor, a pressure sensor, an oxygen sensor, a PH sensor, a flow sensor, an electrical sensor, a strain sensor, a magnetic sensor, and an imaging sensor. In some variations, the stimulator is selected from the group consisting of an electrical stimulator, an optical stimulator, a chemical stimulator, and a mechanical stimulator. In some variations, the implantable device comprises a modular design that allows interchangeable sensors and/or stimulators. In some variations, the one or more subwavelength structures are selected from the group consisting of a patch, a PIFA, a slot, a cross slot, an aperture coupled circular slot, and a half slot. In some variations, the source is configured to adjust a position of a focal point of the spatially focused field. In some of these variations, the implant comprises a sensor to detect a power level of received wireless energy, and comprises a transmitter to provide feedback to the external module to automatically adjust the position of the focal point to optimize wireless power transmission. In some variations, the implant is configured to be implanted on, in, or near a heart to apply leadless pacing to the heart. In some variations, the implant is configured to be implanted on, in, or near a brain to apply deep brain stimulation to the brain. In some variations, the implant is configured to be implanted on, in, or near a spinal cord to apply stimulation to the spinal cord. In some variations, the implant is configured to be implanted on, in, or near a muscular tissue of the tongue to apply stimulation to the tongue to treat obstructive sleep apnea.

Also described herein is a method of cardiac pacing, comprising implanting a wireless power receiving module in, on, or near a heart, transmitting a midfield propagating wave to the wireless power receiving module to power the module, sensing a parameter of the heart with the module; and providing electrical pacing to the heart with the module.

Also described herein is a method of deep brain stimulation, comprising implanting a wireless power receiving module in, on, or near a brain, transmitting a midfield propagating wave to the wireless power receiving module to power the module, sensing a parameter of the brain with the module, and providing stimulation to the brain with the module.

Also described herein is a method of stimulating tissue, comprising: implanting a wireless power receiving module into tissue, transmitting a midfield propagating wave to the wireless power receiving module to power the module, and sensing a parameter of the tissue with the module; and providing stimulation to the tissue with the module. In some variations, the method further comprises adjusting a focal point of the propagating wave to optimize wireless power transmission to the module. In some variations, the transmitting step comprises transmitting the wave with a sub-wavelength structure that produces a magnetic field perpendicular to the wave and parallel to a tissue interface.

BRIEF DESCRIPTION OF THE DRAWINGS

FIGS. 3A and 3C show a magnetic field generated by a midfield source for power transfer across the multilayered material of FIG. 2B. FIGS. 3B and 3D show a magnetic field generated by a near-field source for power transfer across the multilayered material of FIG. 2B.

FIGS. 8A-8F show schematics of subwavelength structures described here.

FIGS. 9A-9B show schematics of subwavelength structures described here.

FIGS. 13A-13B show schematics of a midfield source comprising four sub-wavelength structures fed by one excitation port.

FIG. 16A shows the spatial frequency spectrum of the output field. FIG. 16B shows the power transfer efficiency. FIG. 16C shows the scattering spectrum.

FIGS. 27C-27D show measurements of the power transfer in the setup of FIG. 27A and that the power transfer is well below the threshold.

DETAILED DESCRIPTION

Figure 1:
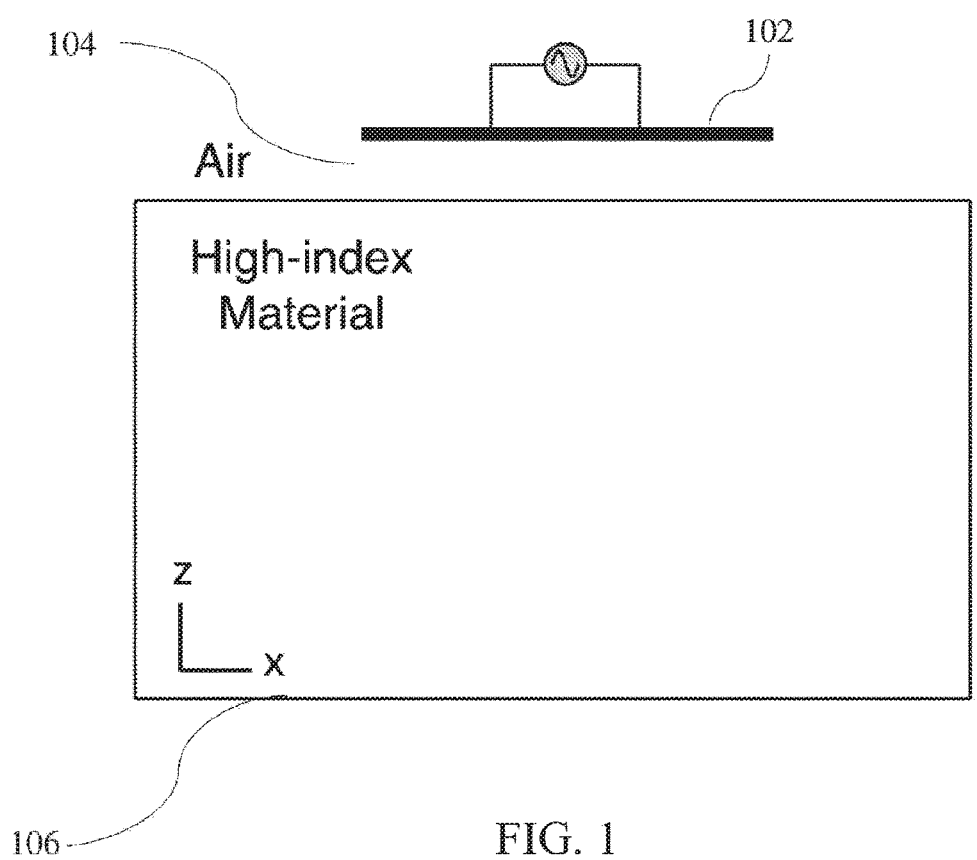
FIG. 1 shows a schematic side view of a source located above an interface between air and a high-index material.

Difficulties in achieving wireless power transfer may occur in the mismatch between the size of the implantable devices/sensors and the power transfer source, the depth of the devices/sensors in a patient, and additionally the spatial arrangement of the devices/sensors relative to the power transfer source. Described here are devices, systems, and methods for wireless powering of microimplants that may overcome these problems. The power sources described herein may generate a non-stationary evanescent field, which may induce energy transfer through the propagating modes of the tissue volume. The region where the energy transfer, termed the electromagnetic midfield, is about a wavelength's distance from the source, where the wavelength corresponds to that of the biological material.

In conventional wireless powering approaches using near-field coupling (inductive coupling and its resonant enhanced derivatives), the evanescent components outside tissue (near the source) remain evanescent inside tissue, which does not allow for effective depth penetration. Unlike conventional near-field coupling, energy from the midfield source is primarily carried in propagating modes and, as a result, the transport depth is limited by environmental losses rather than the intrinsic exponential decay of the near-field. Theoretical studies have shown that energy transfer implemented with these characteristics can be two to three orders of magnitude more efficient than near-field systems. In midfield coupling, the tissue may act as a dielectric to tunnel energy, and coherent interference of the propagating modes may confine the field at the focal plane to dimensions much smaller that the vacuum wavelength, with a spot size subject to the diffraction limit in a high-index material. By locating an implant at this high energy density region, the implant may be able to be made orders of magnitudes smaller, and may be able to be placed deeper within a material, than in systems using traditional wireless powering methods. Indeed, due to the high dielectric permittivity exhibited by biological tissue at microwave frequencies, the power sources described herein may be configured to deliver electromagnetic energy to implantable devices at the scale of a millimeter or less implanted deep inside the body.

Theoretical Basis

The physics underlying the devices, systems, and methods described here arises from an optimization methodology that bounds the performance achievable by any physical realization of a power source. Power transfer occurs when a source generates fields whose interaction with a receiver coil results in work extraction by a load in the receiver circuit. For a subwavelength receiver coil, only the lowest order mode is important, and the power transfer mechanism can be described by electromagnetic induction characteristic of dynamic magnetic field interactions. The power transferred to the coil is given by $$P_{SC} = \int d^3 r M_C(t) \cdot \frac{dB_S(t)}{dt}$$

where $B_S$ is the magnetic field generated by the source and $M_C$ the induced magnetization due to current in the coil. The electric and magnetic fields generated by a time-harmonic current density $J_S$ on surface of the source conductor can be solved by decomposing the current density into its spatial frequency components, each of which obey the usual laws for refraction and reflection across planar interfaces. Using phasor notation with a time dependence of $\exp(-i\omega t)$, the efficiency may be defined as:

$$\eta = \frac{\left|\int d^3 r M_C^* \cdot B_S\right|^2}{[\int d^3 r \operatorname{Im} \in (\omega)|E_S|^2][\int d^3 r \operatorname{Im} \in (\omega)|E_C|^2]}$$

Formally, $\eta$ is the ratio of power available at the coil to the total absorbed power. This equation considers only dissipation in tissue: other losses, such as radiation and ohmic loss, may arise in practice, but the amount of power that can be coupled into the body may be essentially limited by electric field-induced heating.

This efficiency is intrinsic to the fields in the tissue multilayer structure and gives an upper bound on the efficiency that can be obtained. This expression for efficiency can be derived using coupled mode theory: The exchange of energy between the source and receiver is described by the equations $$\dot{a}_S(t)=(i\omega_S-\Gamma_S)a_C(t)+\kappa a_S(t)$$

$$\dot{a}_C(t)=(i\omega_C-\Gamma_C-\Gamma_L)a_C(t)+\kappa a_S(t)$$

where $a_n$ are amplitudes normalized such that $|a_n|^2$ corresponds to the energy in the structure, $\Gamma_n$ the intrinsic decay rates, $\Gamma_L$ the rate of work extraction by the load on the receiver, and $\kappa$ the coupling coefficient. It may be advantageous to operate with the source and receiver in resonance $\omega=\omega_S=\omega_C$. The efficiency of power transfer is defined as $$\eta' = \frac{\Gamma_L|a_S|^2}{\Gamma_S|a_S|^2 + (\Gamma_C+\Gamma_C)|a_S|^2 + \text{Re}(\kappa a_S^* a_C)}$$

In the limit of weak coupling $|\kappa|^2/\Gamma_S\Gamma_C \ll 1$, the expression reduces to $$\eta' = \frac{|\kappa|^2}{\Gamma_S\Gamma_C} \frac{\Gamma_C\Gamma_L}{(1+\Gamma_C/\Gamma_L)^2}$$

which is the product of two efficiencies. The left hand factor can be understood as the efficiency of power transfer to the coil in absence of the load. The right-hand factor corresponds to the efficiency of power extraction by the load—this factor is maximized when the impedance-matching condition $\Gamma_C=\Gamma_L$ is satisfied. From standard power arguments, it can be shown that the left-hand efficiency is given by $$\frac{|\kappa|^2}{\Gamma_S\Gamma_C} = \frac{\left|\int d^3 r B_S^* \cdot M_C\right|^2}{[\int d^3 r \text{Im}\in(\omega)|E_S|^2][\int d^3 r \text{Im}\in(\omega)|E_C|^2]}$$

which is the efficiency defined above. Equivalent expressions can be obtained using other formalisms for coupled electrical systems, such as a two-port lumped element network.

Source $J_S$ may be chosen to maximize efficiency. The global optimum may be analytically solved for a specified powering configuration by defining an electric current with components tangential to a plane between the source structure and tissue. For every source, the electromagnetic equivalence theorem enables such a two-dimensional current density to be chosen from the overall set S that is indistinguishable in the lower $z<0$ half-space from the physical source of the fields. Remarkably, solution to the optimization problem maximize $_{J_S \in S}\eta(J_S)$ can be found in closed-form as a consequence of the vector space structure of S. In contrast with local optimization algorithms, this solution obtained is a rigorous bound on the performance that can be achieved by any physical realization of the wireless powering source.

This theory may be applied to systems comprising an external power source and implanted device, as described herein. FIG. 1 shows a schematic of a side view of a source 102 located above an interface between air 104 and a high-index material 106. The source 102 may produce an in-plane source current density $J_S$. This source current may generate an electric field $E_S$ and magnetic field $H_S$ as described by the dyadic Green functions, $G_E$ and $G_H$:

$$E_S(r)=i\omega\mu_0\int G_E(r-r')J_S(r')dr'$$

$$H_S(r)=\int G_B(r-r')J_S(r')dr'$$

where $\omega$ is the angular frequency and to is the permeability of air. Applying the Fourier transform in each of the transverse coordinates yields the spatial frequency spectra of the fields:

$$E_S(k_x,k_y,z)=i\omega\mu_0 G_E(k_x,k_y,z)J_S(k_x,k_y)$$

$$H_S(k_x,k_y,z)=G_H(k_x,k_y,z)J_S(k_x,k_y).$$

If $k_0$ is the wavenumber of air, the spectral components in air where $$k_x^2+k_y^2>k_0^2$$

correspond to the evanescent fields in air.

Energy transfer from the source 102 to a receiver coil located within the high-index material 106 may occur when the source 102 generates fields whose interaction with the coil results in work extraction by a load in the receiver circuit. The time-averaged power transferred to the coil may be given by $$\langle P_{SC}\rangle = \frac{1}{2}\text{Re}\left[i\omega\int\mu_0 H_S^*(r)\cdot M_C(r)dr\right]$$

where $M_C$ is the induced magnetization on the coil. The power transfer efficiency in terms of the fields is thus defined as $$\eta = \frac{\left|\int\mu_0 H_S^*(r)\cdot M_C(r)dr\right|^2}{\int\text{Im}[\varepsilon(r)]|E_S(r)|^2 dr \int\text{Im}[\varepsilon(r)]|E_C(r)|^2 dr}$$

where $\in$ is the permittivity of the material and $E_C$ is the electric field generated by $M_C$. Formally, $\eta$ is the ratio of power available at the coil to the total power dissipated in the material.

The efficiency of power transfer as defined by $\eta$ above may be changed by the choice of source $J_S$. When the air-material medium is a multilayer structure, the global optimum may be analytically solved. By exploring such global solutions across a range of frequencies with appropriate dispersion models for biological materials, the optimal power transfer for particular biological tissue or tissues may be determined. For example, the theory described above may be used to determine the optimal power transfer for an approximation of the chest wall structure. FIG. 2A illustrates a schematic for power transfer to a coil mounted on the surface of the heart. The chest wall may be approximated by a multilayer structure as shown in FIG. 2B. As shown in FIG. 2A, the powering configuration may consist of a source 202 (described in more detail below) positioned above the skin and a receiver coil 204 (described in more detail below) inserted in the cardiac tissue layer. The optimal power transfer for this approximated chest wall structure may be determined by solving the optimal source $J_S$ across a range of frequencies with appropriate dispersion models for the appropriate biological materials.

In this example, optimal power transfer may occur at 1.6 GHz. To determine this, theoretical efficiency versus frequency curves were generated by solving for the optimal η in a multilayer model of tissue (1 cm air gap, 4 mm skin, 8 mm fat, 8 mm muscle, 16 mm bone, ∞ heart) across a wide search range (10 MHz to 4 GHz) for coils oriented in the x and z directions. The upper frequency bound was selected to be about the self-resonance frequency of the coil. The coil losses were taken into account using an analytical model for a loop of wire embedded in uniform tissue, as well as impedance matching by imposing the constraint Q<10, where Q is the quality factor. Using the Debye dispersion model for each tissue type, the peak efficiency was found to occur at 1.6 GHz.

As shown in FIG. 2B, the solution for $J_S$ may yield a highly oscillatory electric current density 206 that may cause the output field to converge on the receiver coil 204. The fields were calculated from the spectral components of an in-plane source current density $J_S(k_x,k_y)$ using the dyadic Green's function method. This method reduced to a simple transfer function because the plane-wave components are Eigen functions of propagation in the multilayer structure. At each depth z, for example, a dyad $G_H(k_x,k_y,z)$ was applied to calculate the magnetic field $H(k_x,k_y,z)=G_H(k_x,k_y,z) J_C(k_x,k_y)$. An inverse Fourier transform yields the fields at each depth.

Figure 2C:
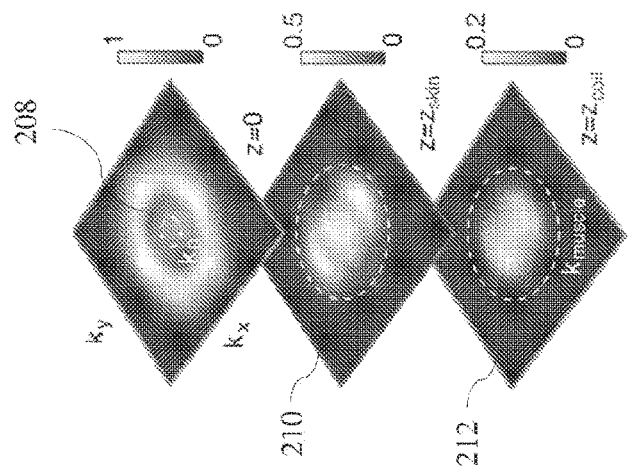
FIGS. 2B and 2C show a magnetic field generated by a source current density optimized for power transfer across a multilayered material.
Figure 2B:
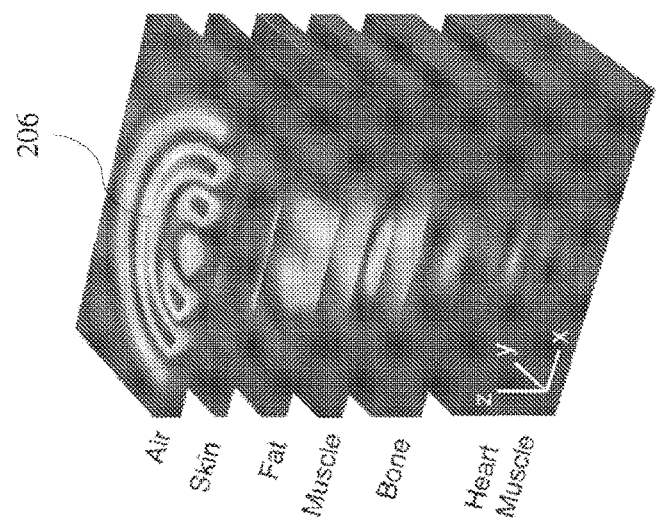
Figure 2A:
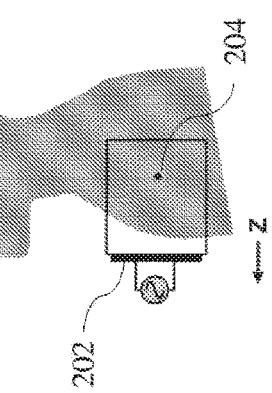
FIG. 2A shows schematic for power transfer to a coil mounted on the surface of the heart.

FIG. 2C plots the spatial frequency spectra at depth planes corresponding to the source (z=0), the skin surface ($z=z_{skin}=-1$ cm), and the coil ($z=z_{coil}=-5$ cm). At the depth plans corresponding to the source and the skin surface, the output fields 208 and 210, respectively, may be composed of significant evanescent components corresponding to $$\sqrt{k_x^2 + k_y^2} > k_0.$$

Near the receiver coil 204, the output field 212 may be composed of significant propagating modes corresponding to $$\sqrt{k_x^2 + k_y^2} \leq k_{muscle},$$

where $k_{muscle}$ is the wavenumber in muscle tissue. Thus, due to the high dielectric permittivity exhibited by biological materials at microwave frequencies, complete control of the propagating modes in tissue may be achieved when the source "lens" affects evanescent wave components that lie in the range of $$k_0 \leq \sqrt{k_x^2 + k_y^2} < k_{msucle}.$$

FIG. 3A shows a time snapshot of the output magnetic field from a midfield source having such a lens, while FIG. 3C shows the normalized spatial frequency spectrum of the output field adjacent to the midfield source. In contrast, FIG. 3B shows a time snapshot of the output field from a corresponding near-field source comprising a coil having a diameter of 4 cm and operating at 10 MHz, normalized such that the maximum electric field in the tissue is the same in FIGS. 3A and 3B. FIG. 3D shows the normalized spatial frequency spectrum of the output field adjacent to the near-field source. As can be seen in FIG. 3B, the fields from the near-field source decay much more quickly than the fields from the midfield source, and are not propagating. Similarly, the spatial frequency spectrum shown in FIG. 3C shows $$k_0 \leq \sqrt{k_x^2 + k_y^2} < k_{msucle},$$

while most of the components shown in FIG. 3D lie in $$\sqrt{k_x^2 + k_y^2} \gg k_{msucle} > k_0 > k_0$$

which are non-propagating in both air and tissue material.

Figures 4A, 4B:
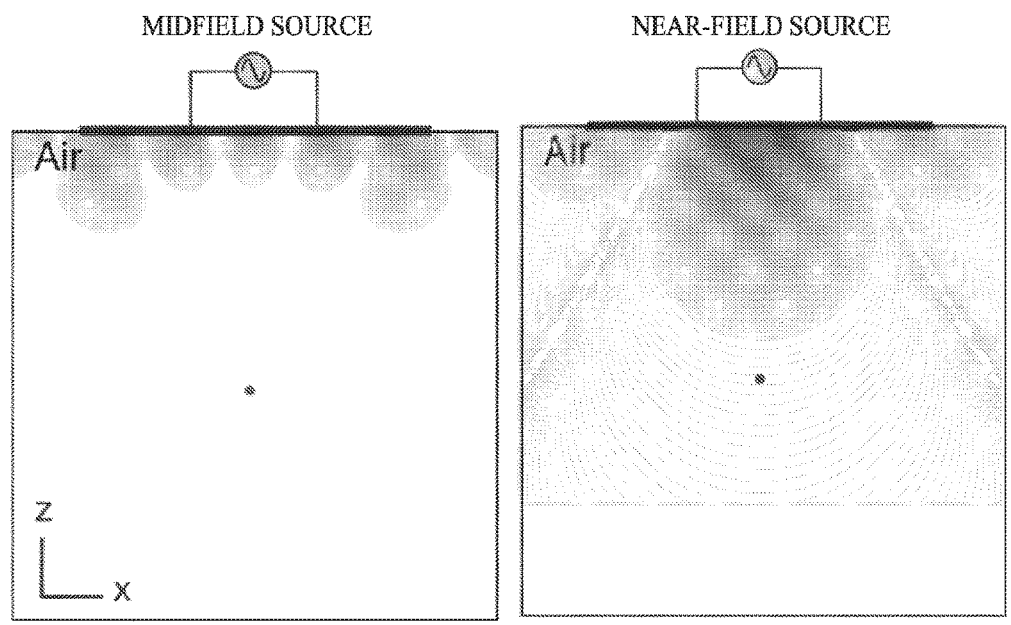
FIGS. 4A and 4B show the magnetic field generated by a midfield source and a near-field source, respectively, in the absence of the multilayered material of FIG. 2B.

Unlike conventional near-field coupling, midfield powering exploits the high dielectric permittivity exhibited by biological materials at microwave frequencies to facilitate the transport of energy. Thus, the benefit may not be seen in instances in which tissue is not present between the source and the receiver coil. For example. FIG. 4A plots the output magnetic field from the midfield source when the tissue material is removed, while FIG. 4B plots the output magnetic field from the near-field source when the tissue material is removed. As can be seen, the magnetic fields from the midfield source shown in FIG. 4A may decay more quickly than when the tissue material is present, and are not propagating, as was shown in FIG. 3A.

Figure 5:
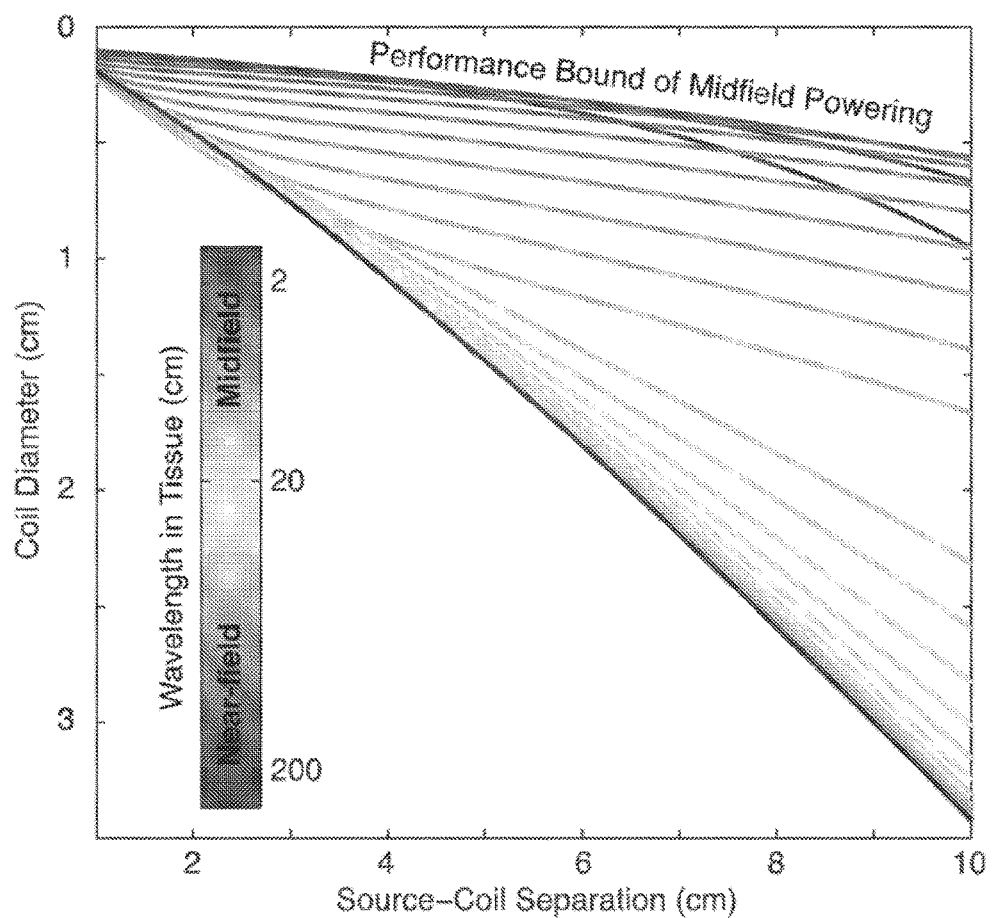
FIG. 5 plots performance curves for midfield and near-field coupling for a fixed power transfer efficiency.

The difference between the power transfer using near-field and midfield coupling may also be illustrated by performance curves—diameter of the receive coil versus power transfer range. FIG. 5 plots the performance curves for a fixed power transfer efficiency $\eta=10^{-3}$ and circuit load of 10Ω. To achieve this efficiency at a given wavelength, the coil size and operating depth is constrained to lie under the performance curve. The curves may be generated by solving for optimal power transfer in an air-muscle half-space for the indicated depths and wavelength in tissue. For example, for an operating depth (distance between the source and the receive coil) of 5 cm, a near-field source may require the diameter of the receiver coil to be at least 15 mm, while a midfield source may only require the diameter of the receiver coil to be at least 2 mm. This performance curve indicates that transporting electromagnetic energy deep in the body to implantable devices at the scale of a millimeter or less is possible.

Devices

Described herein are devices, systems, and methods for realizing a midfield source as described theoretically above. The implementation of a source having the required lensing properties as laid out about requires electromagnetic structures more complex than conventional coil or dipole elements. In one variation, a midfield source may be realized by midfield plate, which may comprise one of more subwavelength structures, and excitation ports configured to excite the subwavelength structures. These midfield sources may manipulate evanescent fields near the source to excite and control propagating fields inside a material (e.g., tissue) and thereby generate a spatially focused and adaptive steering field in the material. The energy may be received by an implanted device, described in more detail below.

The systems described herein may allow for wireless power transfer to implanted devices at depths unattainable with conventional inductive coupling technology. Moreover, the implants may be able to be much smaller (e.g., by one, two, or three orders of magnitude) than the external power source, and much smaller (e.g., by one, two, or three orders of magnitude) than their depth within a material (e.g., tissue). The power that may be transferred to an implant via the systems described herein may also be sufficient to power the delivery of stimuli and/or complex electronics in the implant.

External Module (Midfield Source)

Figure 6C:
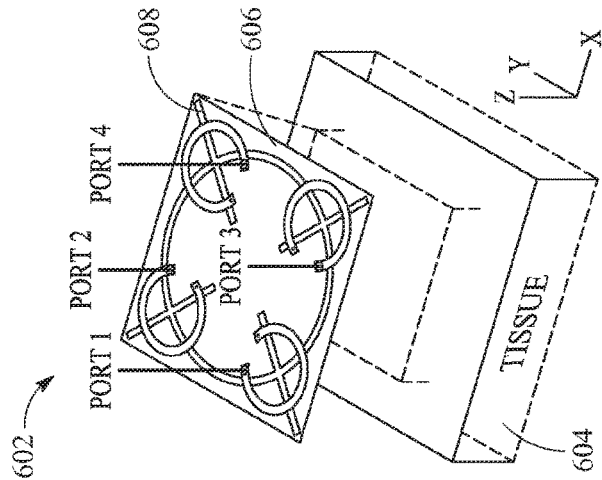
FIGS. 6A-6C show perspective top views of variations of midfield sources described here placed near representative tissue.
Figure 6B:
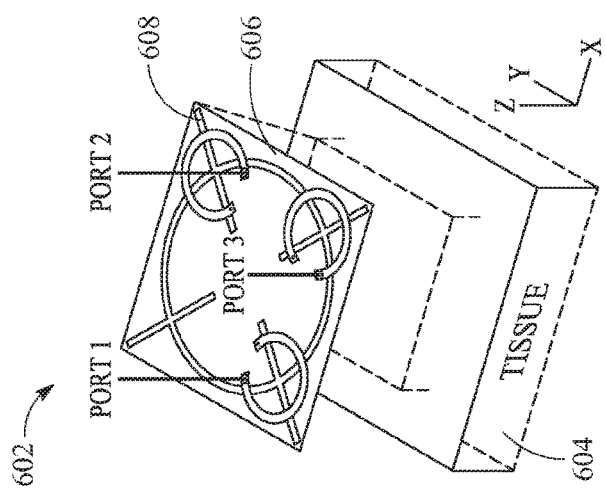
Figure 6A:
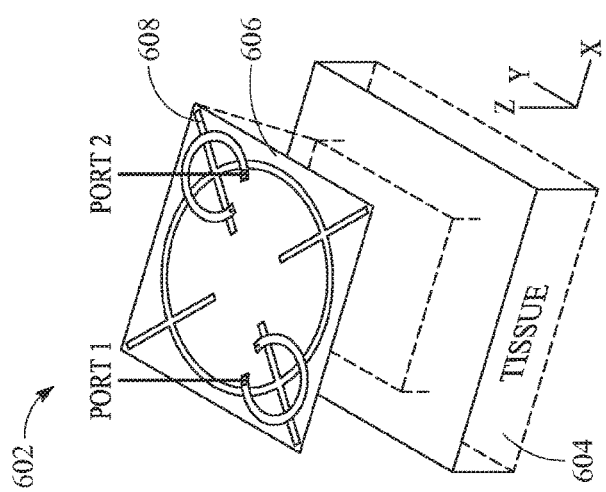

Described herein are midfield sources configured to generate power that may be wirelessly transferred to implants. In some variations, the entire midfield source may be integrated into a hand-held device. As such, the midfield source may be suitable for on-demand use. In other variations, the midfield source may be configured to be worn on the body or affixed to the skin surface. FIGS. 6A-6C show perspective top views of variations of midfield sources 602 placed near representative tissue 604. As shown there, each midfield source 602 may comprise a midfield plate, which may comprise a planar surface 606 and one or more subwavelength structures 608. The one or more subwavelength structures 608 on the midfield plate may be excited by one or more radio-frequency ports, which together may form the midfield source, as described in more detail below.

Planar Surface

In some variations, the planar surfaces of the midfield sources described herein may comprise a solid substrate or plate. For example, the planar surface may in some variations comprise glass epoxy laminates, such as FR-4, which may comprise feed and patterned copper layers. In other variations, the planar surface may comprise Rogers or ceramic for lower substrate loss. The planar surface may have a generally planar shape, and may have any suitable dimensions. The thickness may depend on the number of metal layers in the substrate, and may range from about 1 mm to about 3 cm. In some variations, the solid substrate may be approximately 6 cm by 6 cm, and have a thickness of about 1.6 mm.

In other variations, the planar surface may comprise a flexible substrate. In some variations in which the planar surface comprises a flexible substrate, the flexible substrate may be an ultrathin flexible substrate, and may be configured to conform to an irregular or curved surface, such as a patient's skin. For example, the planar surface may in some variations comprise ultrathin FR-4. In some variations, the flexible substrate may have a thickness of about 10 μm to about 1 mm. More specifically, in some variations, the flexible substrate may have a thickness of about 100 μm. The thickness may depend on the number of metal layers in the substrate and the isolation between different layers.

Figure 28C:
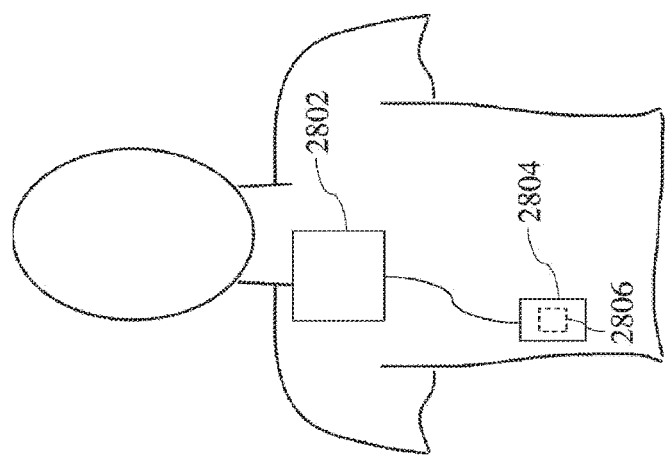
FIGS. 28A-28C show midfield sources attached to a patient.
Figure 28B:
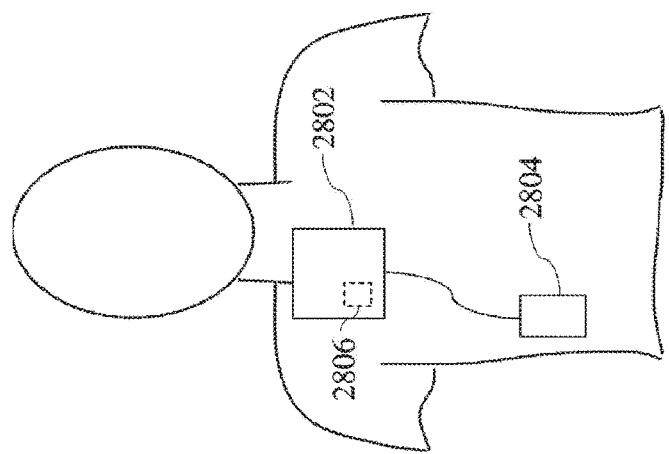
Figure 28A:
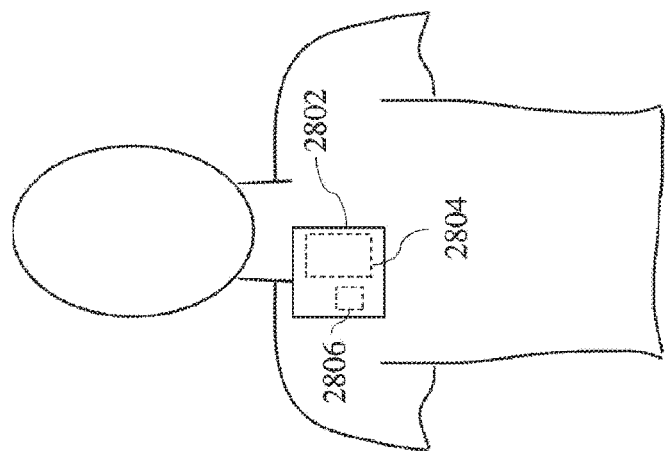

The planar surface may be configured to adhere to a patient's skin, as shown in FIGS. 28A-28C. A spacer may be placed in between the planar surface and skin for insulation. In some variations, the planar surface 2802 together with a battery 2804 and circuits 2806 may be combined into a thin patch. This may be adhered to the skin, as shown in FIG. 28A. In another variations, a battery 2804 may be separate from the patch, and the patch and battery 2804 may be configured to be separately adhered to the skin, as shown in FIG. 28B. In yet another variation, a battery 2804 and circuits 2806 may be combined, and may be configured to be adhered to the skin separately from the patch, as shown in FIG. 28C. A flexible substrate configured to adhere to the patient's skin may be configured to be worn for any suitable period of time, and may depend on the application. For example, in some variations the systems described herein may be used for on-demand stimulation, and the planar surface may be left on the patient's skin during the period of stimulation (e.g., about one hour to about a few hours), although it should be appreciated that the surface may be adhered to the patient's skin for a longer period of time. In other variations, the systems described herein may be used for charging a battery in the implanted device. In some such variations, the planar surface may be left on the patient's skin for about 1 minute to about 10 minutes, although it should be appreciated that the surface may be adhered to the patient's skin for a longer period of time.

Subwavelength Structures

As mentioned briefly above, the planar surface may be combined with one or more subwavelength structures to form a midfield plate. A "subwavelength structure" may be defined relative to the wavelength of the field. If $\lambda_0$ is the wavelength in air and $\lambda_{material}$ is the wavelength in a high-dielectric material, any source structure that is of dimension much less than the wavelength in air $\lambda_0$ may be termed a subwavelength structure. When the relative permittivity of the high-dielectric material is n, the wavelength in the high-dielectric material is $\sqrt{n}$ times smaller than the wavelength in air, that is, $\lambda_{material} = \lambda_0/\sqrt{n}$. For example, the relative permittivity of muscle at 1.6 GHz is 54, and therefore $\lambda_{material} = \lambda_0/7.3$. Hence, any source structure that is of dimension on the order of $\lambda_{material}$ may be a subwavelength structure. More specifically, the largest dimension of each subwavelength structure d may be in between 0.1 $\lambda_{material}$ and 2 $\lambda_{material}$. When this is the case, the subwavelength structures may generate evanescent fields, and when they are placed in close proximity to a high-dielectric material, the evanescent fields may induce energy transfer through the propagating modes of the high-dielectric material. The spatial frequency spectrum of the output field adjacent to the source has significant components in $$k_0 \leq \sqrt{k_x^2 + k_y^2} < k_{muscle},$$

as explained in more detail above.

The subwavelength structures may have any suitable design configured to generate and manipulate propagating fields in material (e.g., tissue), as described in more detail herein. In some variations, the subwavelength structures may comprise slots in a ground plane. In other variations, the subwavelength structures may comprise strips of metal or patches of metal, which may be disposed over a substrate, which may in turn have a ground plane underneath, but need not. The metal strips or patches may comprise any suitable material, such as but not limited to copper. The metal strips and patches may have any suitable thickness, such as but not limited to about 30 μm.

Figure 7A:
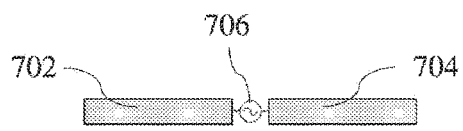
FIGS. 7A-7B show schematics of subwavelength structures described here.
Figure 7B:
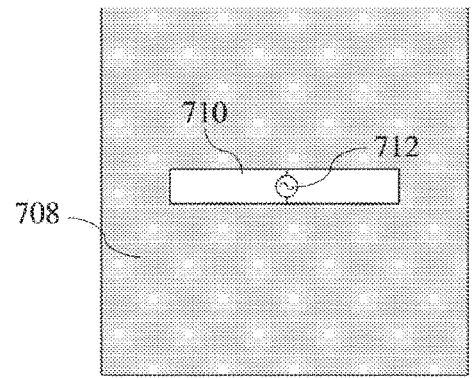

Examples of suitable subwavelength structures are shown in FIGS. 7A-7B. In the variation shown in FIG. 7A, the subwavelength structure may comprise two linear metal strips, 702 and 704, arranged end-to-end. The metal strips 702 and 704 may be excited by a voltage source 706, described in more detail below, located between their ends. The combined length of the metal strips may be between about 1/10 of the wavelength of the magnetic field in the dielectric material (e.g., tissue) and about 2 times the wavelength of the magnetic field in the dielectric material (e.g., tissue), as described above. The metal strips may be placed on top of a planar substrate, as described above. In the variation shown in FIG. 7B, the subwavelength structure may comprise a linear slot 710. The slot may be disposed in a planar surface as described above, such as a metal plate 708 as shown, and the slot 710 may be excited by a voltage source 712, to form a midfield plate (described in more detail below).

Other variations of subwavelength structures are shown in FIGS. 8A-8F. As shown in FIG. 8A, in some variations the subwavelength structure may comprise two curved metal strips 802 and 804, which may form an arc of a circle. As shown in FIG. 8B, in some variations, the subwavelength structure may extend around the full arc of a circle, forming a ring-shaped metal strip 806. In other variations, as shown in FIGS. 8C-8F, the subwavelength structure may comprise one or more slots. In the variation shown in FIG. 8C, the subwavelength structure may comprise a slot 808 forming an arc of a circle. In the variation shown in FIG. 8D, the subwavelength structure may comprise a ring-shaped slot 810. In the variation shown in FIG. 8E, the subwavelength structure may comprise two linear slots 812 and 814 forming a cross. In the variation shown in FIG. 8F, the subwavelength structure may comprise a linear slot 816 and a curved slot 818, intersecting at their midpoints. In each variation shown in FIGS. 8A-8F, each subwavelength structure may be excited by a single voltage source 820 (described in more detail below). That is, there is only one point in the structure where the voltage is fixed.

Figure 17:
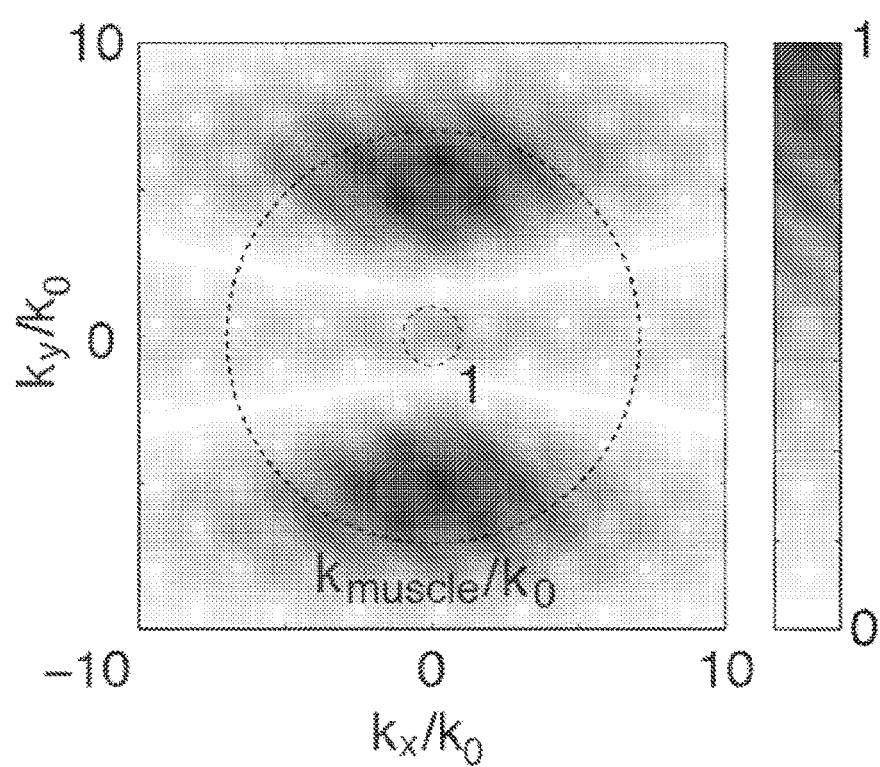
FIG. 17 show the spatial frequency spectra of the output fields from the sub-wavelength structures of FIG. 7A.

Each variation of subwavelength structures described herein may produce electromagnetic fields adjacent to the source where the spatial frequency spectrum of these fields has non-negligible components in $$k_0 \le \sqrt{k_x^2 + k_y^2} < k_{muscle},$$

as explained in more detail above. For example, FIG. 17 shows the spatial frequency spectrum of the transverse electric field adjacent to a midfield source comprising the subwavelength structure shown in FIG. 7A, where the combined length of the metal strips in FIG. 7A is about equal to $\lambda_{muscle}$ at the operating frequency of 1.6 GHz, and the source is placed about 1 cm above an air-muscle interface. As can be seen in FIG. 17, the electric field comprises non-negligible components in $$k_0 \le \sqrt{k_x^2 + k_y^2} < k_{muscle}.$$

In some variations, the subwavelength structures may be configured to minimize the tissue heating effect of the applied fields. Because electric fields induce tissue heating, to minimize the tissue heating effect, subwavelength structures may be configured to yield magnetic fields dominating near the source. Additionally or alternatively, the subwavelength structures may be configured to be low profile. For example, it may be desirable for the subwavelength structures to comprise slots and/or patches due to their low-profile structures.

In other variations, the subwavelength structures may be configured to yield transverse magnetic field dominating near the source. In some of these variations, the subwavelength structure may comprise a patch subwavelength structure—a subwavelength metal plate on a substrate underneath by a ground plane (as shown in FIG. 11A), a PIFA subwavelength structure—similar to a patch subwavelength structure, except that one side of the patch may be shorted to the ground plane (as shown in FIG. 11B), a cross slot subwavelength structure (as shown in FIG. 11C), an aperture-coupled circular slot subwavelength structure, wherein the excitation of the slot structure is by a monopole in proximity to the slot but not touching the slot (as shown in FIG. 11D), and/or a half slot subwavelength structure (as shown in FIG. 11E).

Figure 11A:
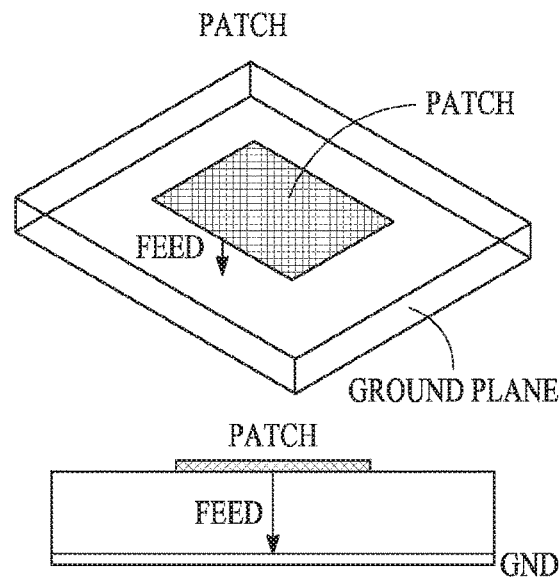
FIGS. 11A-11E show schematics of subwavelength structures described here.
Figure 11B:
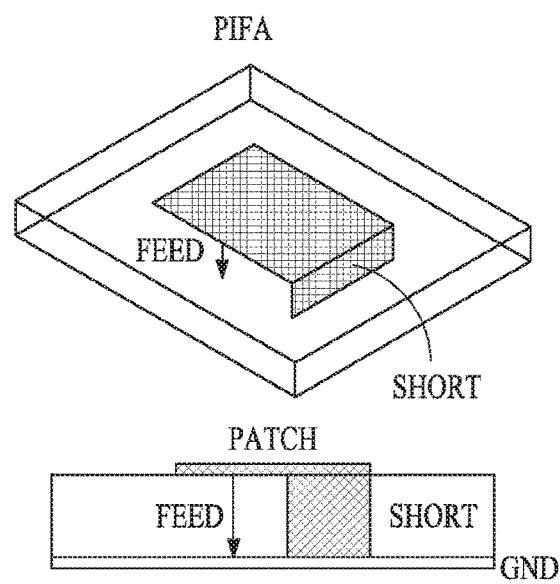
Figure 11E:
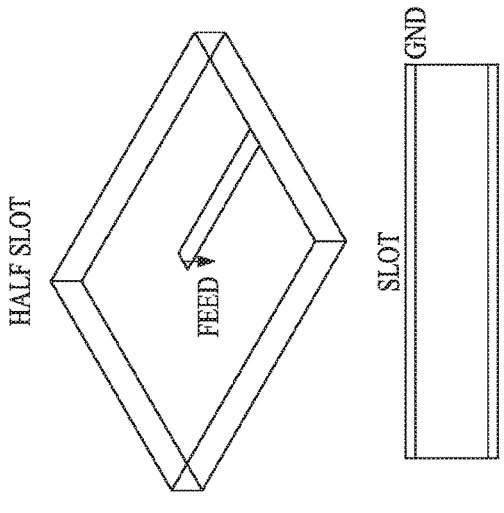
Figure 11D:
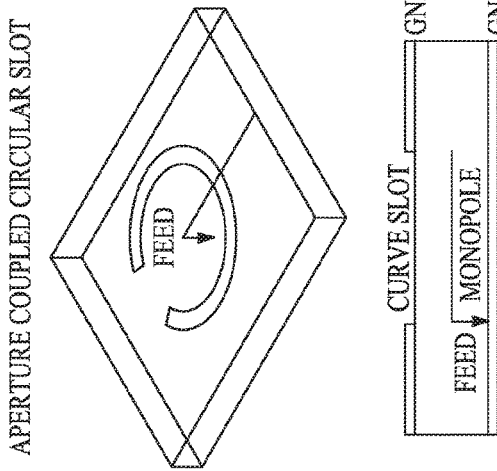
Figure 11C:
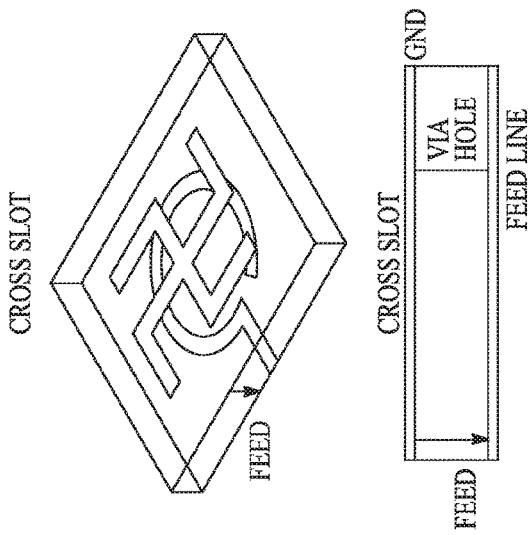
Figure 18A:
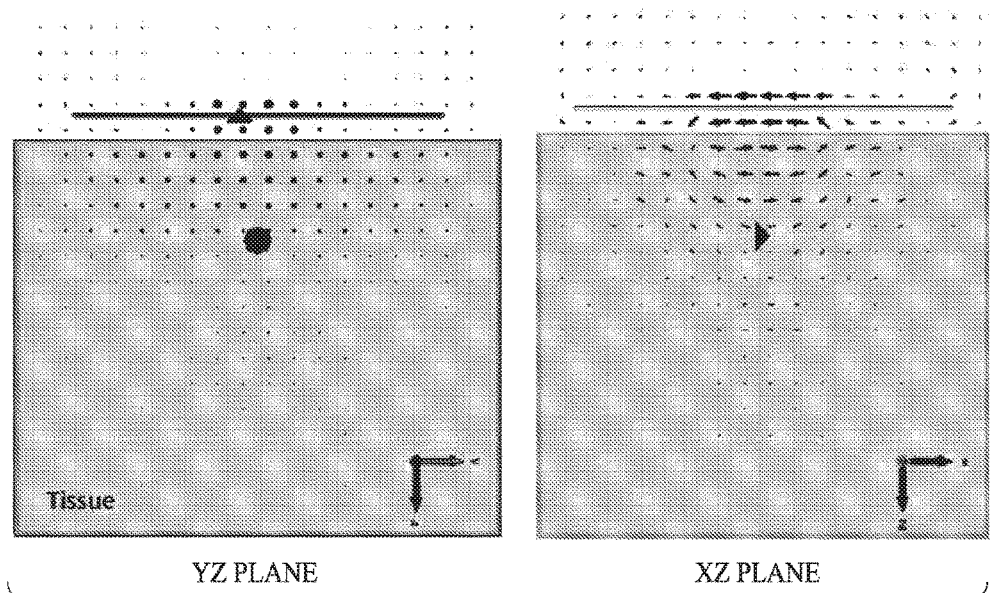
FIGS. 18A-18E show the magnetic fields produced by the subwavelength structures in FIGS. 11A, 11B, 11D, 11C, and 11E, respectively.
Figure 18B:
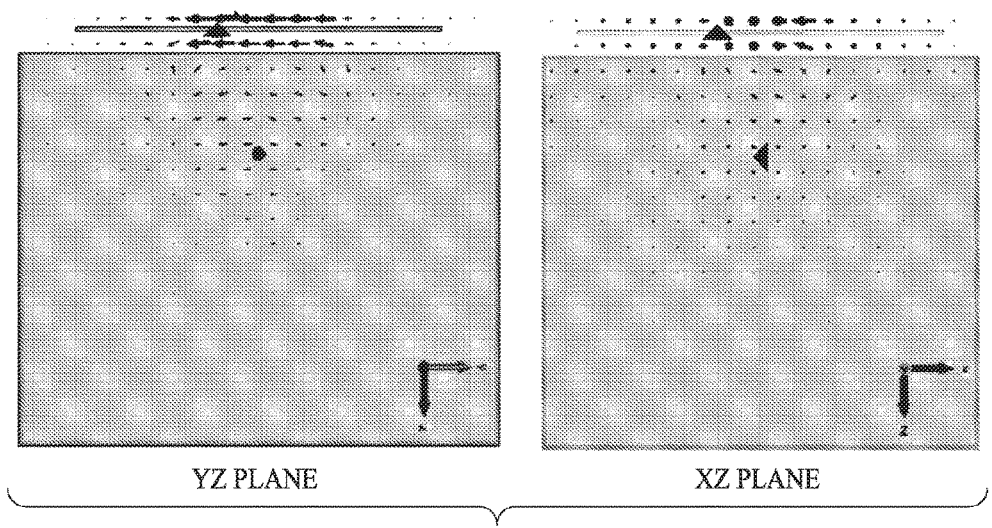
Figure 18C:
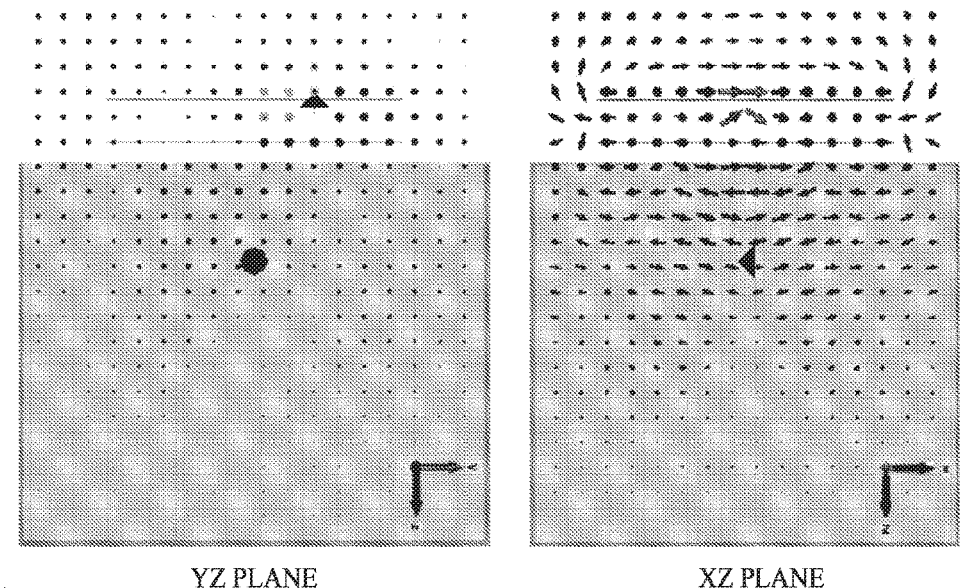
Figure 18D:
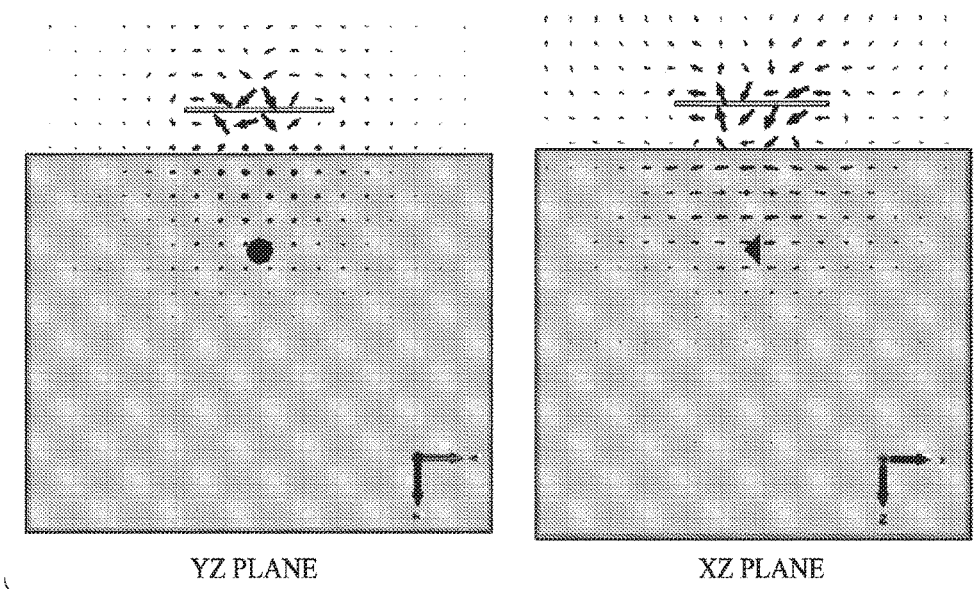
Figure 18E:
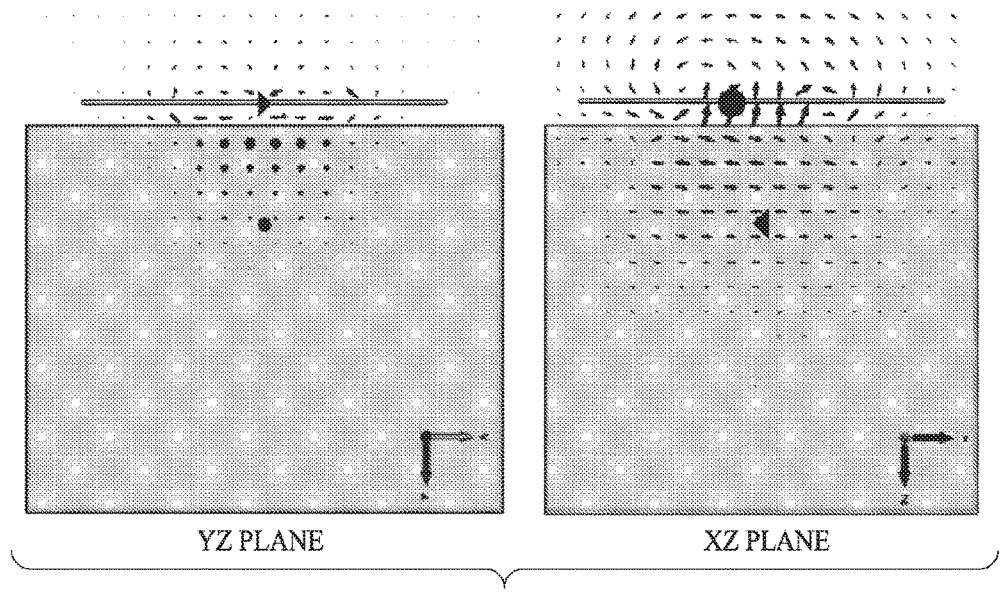
Figure 19:
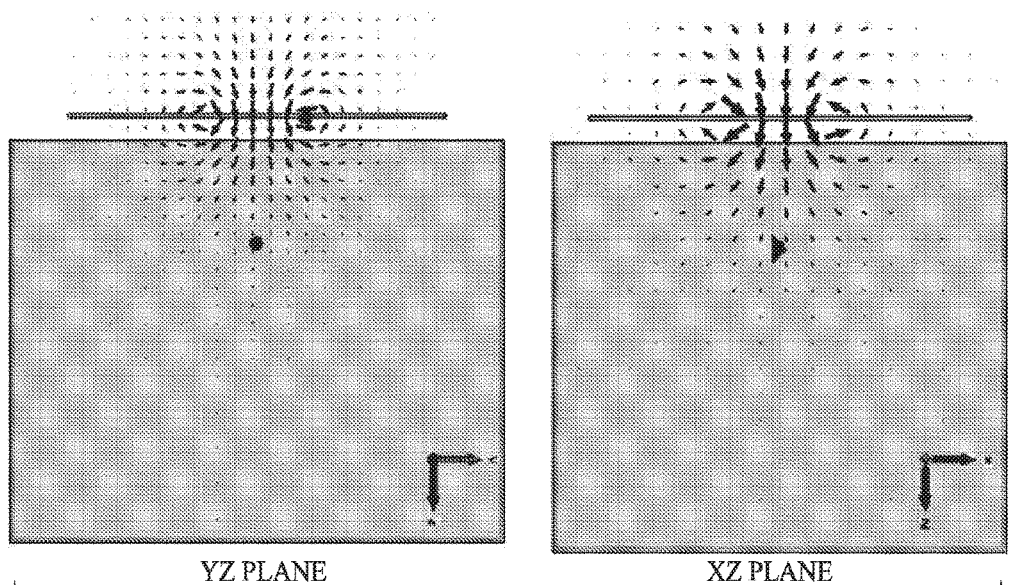
FIG. 19 shows the magnetic field generated by a conventional inductively coupled loop source.

FIGS. 18A-18E show the magnetic fields produced by midfield sources comprising the subwavelength structures of FIGS. 11A-11E. FIG. 18A shows the magnetic field generated with a patch sub-wavelength structure as shown in FIG. 11A. FIG. 18B shows the magnetic field generated with a PIFA subwavelength structure as shown in FIG. 11B. FIG. 18C shows the magnetic field generated with an aperture-coupled circular slot subwavelength structure as shown in FIG. 11D. FIG. 18D shows the magnetic field generated with a cross slot subwavelength structure as shown in FIG. 11C. FIG. 18E shows the magnetic field that results from a half slot subwavelength structure as shown in FIG. 11E. As can be seen, the midfield sources generate a magnetic field parallel to the tissue interface, and perpendicular to the propagating wave generated in tissue that transmits wireless power to an implanted device. In contrast, FIG. 19 shows the magnetic field generated by a conventional inductively coupled loop source. As can be seen, the magnetic field is generated perpendicular to the tissue interface, and is parallel with the direction of desired wireless power transfer to an implant disposed in tissue below the loop source.

Midfield Plate

The planar surface and one or more subwavelength structures as described herein may be combined to form a midfield plate. A midfield plate may comprise any suitable number of subwavelength structures (e.g., one, two, three, four, five, six, seven, eight, or more). Each of the subwavelength structures may be identical, or the midfield plate may comprise a combination of various subwavelength structures, such as those described above.

FIGS. 9A-9B show examples of midfield plates that may comprise more than one subwavelength structure. In the variation shown in FIG. 9A, midfield plate may comprise two semi-circular subwavelength metal strips 902 and 904, configured to form a full ring-shaped structure. Two voltage sources 906 may excite the subwavelength structures. The configuration shown in FIG. 9A is similar to the configuration shown in FIG. 8B, but the configuration in FIG. 9A may comprise two voltage sources, creating two points at which the voltages may be fixed. Thus, the configuration shown in FIG. 9A may comprise two subwavelength structures 902 and 904. FIG. 9B shows a configuration comprising a cross-shape similar to the configuration shown in FIG. 8F, but having four voltage sources 908, creating four points at which the voltages may be fixed, and thus, four subwavelength structures 910, 912, 914, and 916.

Figure 14:
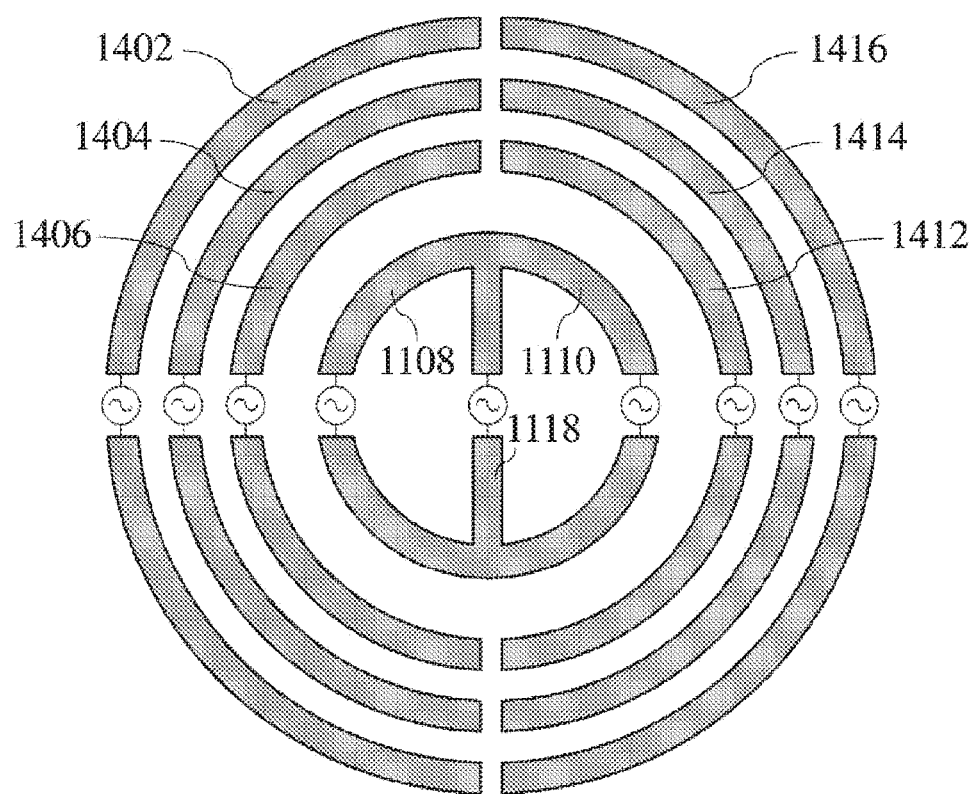
FIG. 14 shows a schematic of a midfield source comprising an array of sub-wavelength structures that approximates an optimal source.
Figure 15:
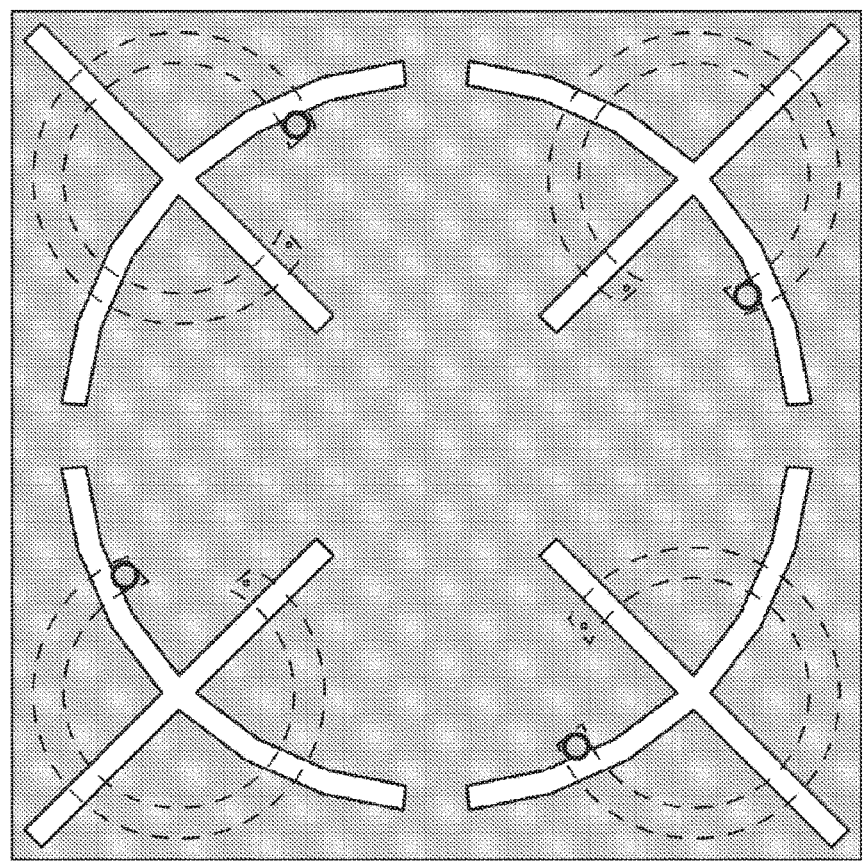
FIG. 15 shows a schematic of a midfield source comprising an array of sub-wavelength structures that approximates an optimal source.

In some variations, the midfield plate may comprise a combination of multiple subwavelength structures that to approach the performance of an optimal source that maximizes the power transfer efficiency, as described above. FIGS. 14 and 15 illustrate two such configurations for midfield sources. In the variation shown in FIG. 15, the midfield plate may comprise of an array of four configurations of subwavelength structures shown in FIG. 13A (described in more detail below). The four configurations of FIG. 13A may be arranged in a circular configuration, with each of the four configurations rotated 90 degrees relative to its neighbors, with the linear slots pointing toward the center of the array. When excited, a midfield plate comprising this arrangement of subwavelength structures may generate circular current paths that may approximate the optimal current density $J_S$ for power delivery across a chest wall to the heart, as described above. In the variation shown, the midfield plate may be excited to form a midfield source by four independent radio-frequency ports connected to microstrip transmission lines, as described in more detail with respect to FIGS. 13A-13B. The amplitude and phase at each port may be chosen to maximize the power transfer efficiency. For appropriate phases between the port signals, the array structure may generate circular current paths that may approximate the optimal current density.

Figure 10A:
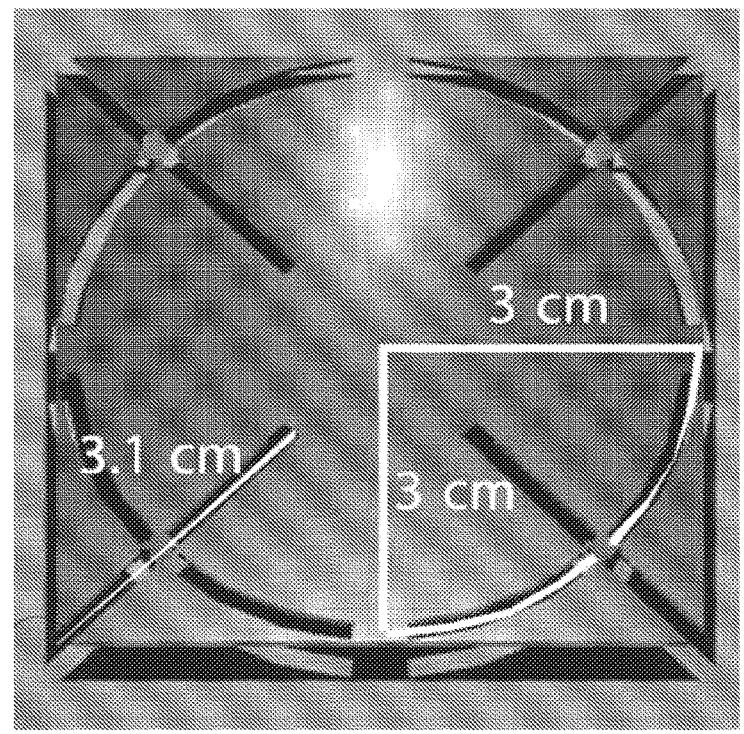
FIGS. 10A-10B show schematics of midfield plates described here.
Figure 10B:
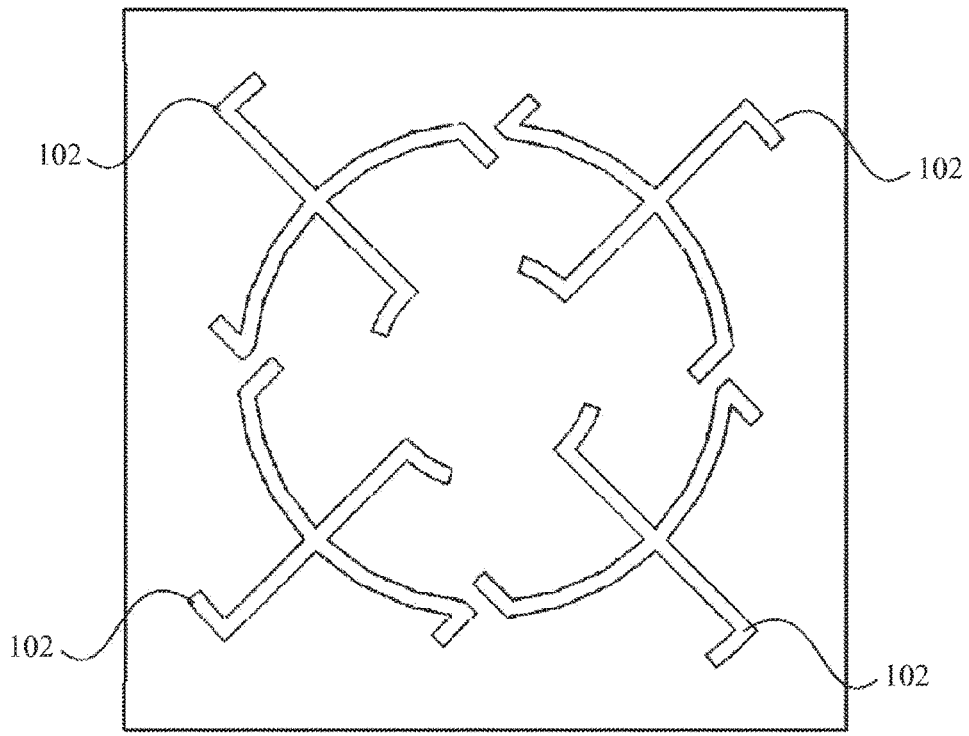
Figure 16A:
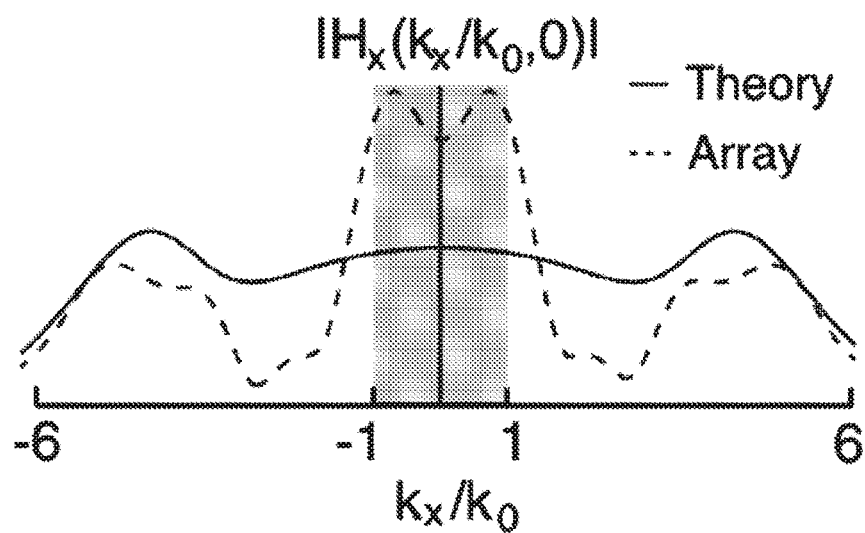
FIGS. 16A-16C show the performance of the midfield source of FIG. 15.
Figure 16B:
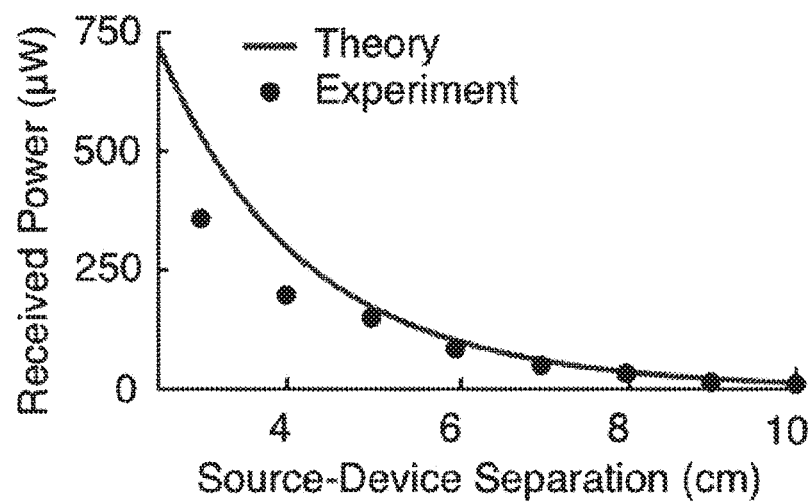
Figure 16C:
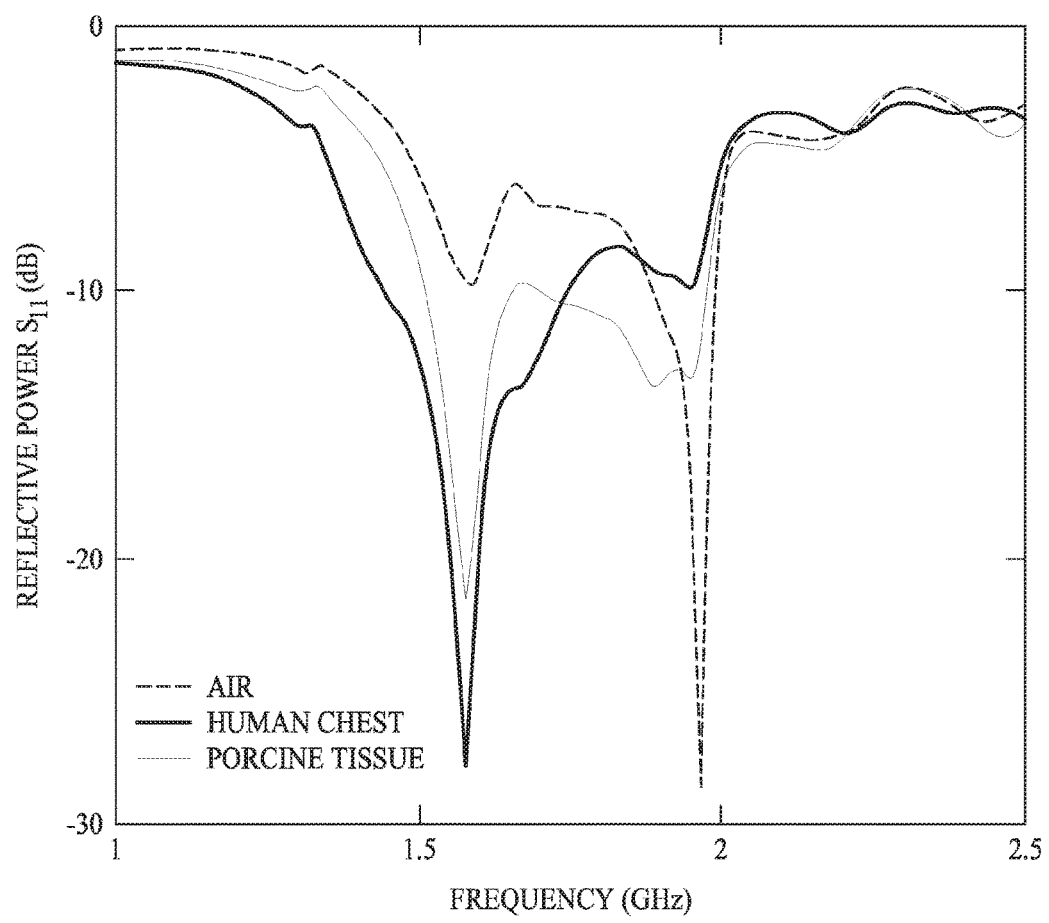

If use of the midfield source shown in FIG. 15 is simulated through an approximated chest wall as shown in the arrangement in FIG. 2A, the spatial frequency spectrum of the array along the $k_x$ axis, compared with the theoretical optimum shown in 210 (at the skin surface) of FIG. 2C, is shown in FIG. 16A. As can be seen in FIG. 16A, the evanescent spectrum may approximate the theoretical optimum, although the contribution of the radiative modes may be about two times greater owing to the inherent directionality of the planar structure. An experimental measurement of the power transfer efficiency is shows in FIG. 16B. When transferring power at 500 mW to an implant having a 2-mm diameter coil and submerged in a liquid solution with dielectric properties mimicking muscle tissue, experimental studies showed that a midfield source having a subwavelength structure configuration as shown in FIG. 15 was able to obtain efficiencies within 10% of the theoretical bound, as shown in FIG. 16B, and evidenced by a pronounced minimum in the scattering spectrum, as shown in FIG. 16C. It should be appreciated that the midfield plate of FIG. 15 may be modified in certain ways. For example, FIG. 10B shows a midfield plate comprising a configuration of subwavelength elements similar to the midfield plate of FIG. 15, except that the slots may comprise bends at each end. These bends may enhances the bandwidth of the midfield source created by exciting the midfield plate.

Planar Immersion Lens

A solid immersion lens includes semispherical domes of high-index material placed at or near the air-material interface that allow light to access these "forbidden" angles of refraction. This capability enables light to be focused to a spot much smaller than the free-space wavelength, with a diffraction-limited resolution set by the material wavelength ~$\lambda/n$. Solid immersion lenses have found extensive use in many applications, including imaging, data storage, and lithography. They are, however, intrinsically three-dimensional and bulky. Replacing conventional solid immersion lenses with flat counterparts would afford opportunities for integration in complex systems, including nanophotonic chips or, in the low frequency regime, conformal biomedical devices.

FIG. 14 shows a planar immersion lens based on metasurfaces. Metasurfaces are flat devices consisting of structured arrays of subwavelength apertures or scatterers that provide an abrupt change in electromagnetic properties as light propagates across the surface. The properties of metasurfaces can be tuned by varying the parameters of the individual subwavelength elements to form a desired spatially varying response. This freedom in design has been used to create devices that generate negative refraction, light vortices, flat lensing, holograms, and other unusual interface phenomena in both optical and microwave regimes. The planar immersion lens of FIG. 14 uses metasurfaces based on electrically thin metallic strips with deep subwavelength spacing that allow radiation incident from air to refract into "forbidden" angles in material. This capability allows production of a thin and planar device that reproduces the functionality of a solid immersion lens. The device can be fabricated on a flexible substrate and can operate at microwave frequencies.

The solid immersion lens is an optical tool that allows light entering material from air or vacuum to focus to a spot much smaller than the free-space wavelength. Conventionally, however, they rely on semispherical topographies and are non-planar and bulky, which limits their integration in many applications. A planar immersion lens is shown in FIG. 14. The resulting planar device, when placed near an interface between air and dielectric material, can focus electromagnetic radiation incident from air to a spot in material smaller than the free-space wavelength.

When light is focused from air into material, refraction at the air-material interface determines the diffraction limit. Conventional optical lenses, placed in the far-field of the interface, control only propagating wave components in air. As a result, their focusing resolution in material is diffraction-limited at the free-space wavelength, $\lambda$. This is at least in part because higher wavevector components in material cannot be accessed by far-field light. These high wavevector components correspond to plane waves propagating at angles greater than the critical angle, which are trapped in the material by total internal reflection.

To allow for interface phenomena different from classical reflection and refraction, a metasurface can be placed at or near an air-material boundary, such as to break translational symmetry at the interface. The metasurface can impart a phase with constant gradient $\nabla\Phi$ on incident light, propagation is governed by a generalized form of Snell's law. The law implies that radiation incident at an angle $\theta_{inc}$ refracts at a forbidden angle $|\theta_{ref}|>\theta_{critical}$ if the phase gradient is sufficiently large $|\nabla\Phi|>k_0-k_0 \sin|\theta_{inc}|$. A phase gradient can be implemented by non-periodically modulating the surface with subwavelength structures of varying impedances. FIG. 14 shows the metasurface. The metasurface can include metallic strips with passive lumped elements (resistors, capacitors, and inductors). At microwave frequencies, these elements can consist of patterned metal traces or commercial impedance components. Across a resonance, the phase of the current in the strips differs from that of the driving electric field by a value between $[0, \pi]$. By selecting suitable passive elements and taking into account both the intrinsic and mutual impedances of the structures, the spatial phase profile of the transmitted wave can be shaped within this phase range. The use of discrete passive elements considerably simplifies the design as the metasurface can be reconfigured by simply changing the elements. Because coupling is explicitly accounted for in the design, the inter-element spacing can be made subwavelength. The phase range can be extended to the full $[0, 2\pi]$ by exploiting changes in polarization (Berry phase), incorporating elements with a magnetic response, and/or cascading multiple layers, although the limited range achieved in the immersion lens of FIG. 14 using a single layer is sufficient.

Refraction at a "forbidden" angle can be achieved using the metasurface to create a phase gradient of $\nabla\Phi=\pi/0.55\lambda$ for radiation at about 1.5 GHz. The spacing between the elements is about $\lambda/20$, and is subwavelength, such as to satisfy sampling requirements. For an s-polarized plane wave incident at $\theta_{inc}=30°$, the beam is entirely refracted to an anomalous angle of $\theta_{ref}=45°$ that lies well beyond the critical angle $\theta_{critical}=30°$. Because the metasurface does not rely on polarization conversion, there is no co-polarized component refracted at an angle dictated by the standard Snell's law. Unlike diffraction gratings, which alter the spatial amplitude profile, the metasurface refracts the incident wave by modulating its phase profile and thus does not result in unwanted diffractive orders.

Anomalous refraction still occurs when a λ/20 air gap is introduced between the metasurface and the interface. This effect is closely related to frustrated total internal reflection. In absence of material below the metasurface, the incident wave completely reflects off the metasurface and forms an evanescent wave at the surface. This evanescent wave propagates along the surface in the direction of the phase gradient, which is a behavior that cannot be realized with a grating. When the material is placed in close proximity to the metasurface, the evanescent field phase matches to a propagating wave in the material, allowing the incident beam to tunnel into the material with the net transport of energy across the interface. By varying the angle of incidence relative to the phase gradient, the angular spectrum of the transmitted beam can be made to lie almost entirely in the forbidden region. The results appear to be in agreement with the generalized Snell's law. The spread around the predicted angle is due at least in part to finite size of the aperture.

To design a planar immersion lens, a field source in air that focuses to a λ/n spot in material can be found. Although focusing across a planar interface has been previously studied, classic expressions for the optimal field source consider only far-field light and yield a ~λ focal spot. A more general approach can be used that accounts for evanescent waves at the interface. An optimization problem over the space of current sheets $j_s$ in the source plane (taken to be z=0) is formulated. The solution can be defined to be the current sheet that maximizes a metric for the degree of focus. Assume that the material is dissipative, allowing small but non-zero loss. The efficiency of work performed on the material as the focusing metric $$\eta = \alpha''|E(r_f)|^2 / \int dr \in'''|E(r)|^2 \quad \text{Equation 1}$$

where $r_f$ is the focal point, $\alpha''$ the imaginary part of the polarizability of the object at the focal point, and $\in'''$ the imaginary part of the material dielectric permittivity. α can be set to be the polarizability of a "virtual" sphere centered at the focal point: the sphere has the same dielectric permittivity as the background material and can be made arbitrarily small (e.g., the diameter of a computational mesh unit). The electric field, E, can be found by propagation from the current sheet js as described by the Green's function G(r, r').

The optimization problem can now be considered in the operator formalism. Using Dirac bracket notation, E and $j_s$ can be represented respectively as functions $|\psi\rangle$ and $|\phi\rangle$ in Hilbert space. They are related through the operator expression $|\psi\rangle = \hat{G}|\phi\rangle$ where $\hat{G}$ is the Green's function operator. A focal position operator $\hat{\Phi}$ can be defined such that the numerator in Equation 1 can be written as $$\langle\psi|\hat{\Phi}|\psi\rangle = \alpha'' \int dr \delta(r_f)|E(r)|^2 = \alpha''|E(r_f)|^2. \quad \text{Equation 2}$$

Similarly, a power loss operator $\hat{\Sigma}$ can be defined to yield $$\langle\psi|\hat{\Sigma}|\psi\rangle = \int dr \in'''|E(r)|^2. \quad \text{Equation 3}$$

Optimal focusing occurs when the choice of the source current density $|\phi\rangle$ maximizes Equation 1. Focusing can thus be posed as an optimization problem $$\max_{|\phi\rangle \in S} \frac{\langle\phi|\hat{G}^T\hat{\Phi}\hat{G}|\phi\rangle}{\langle\phi|\hat{G}^T\hat{\Sigma}\hat{G}|\phi\rangle} \quad \text{Equation 4}$$

where S is the set of all current sheets on a plane above the z=0 plane. The form of Equation 4 is a generalized eigenvalue problem involving the operators $\hat{A} := \hat{G}^T\hat{\Phi}\hat{G}$ and $\hat{B} := \hat{G}^T\hat{\Sigma}\hat{G}$. The solution is given by the two-dimensional current density that satisfies $\hat{A}|\phi_{opt}\rangle = \lambda_{max}\hat{B}|\phi_{opt}\rangle$ where $\lambda_{max}$ is the largest generalized eigenvalue. If $\hat{B}$ is invertible, then the solution $|\phi_{max}\rangle$ can be obtained from a standard eigenvalue decomposition of the operator $\hat{B}^{-1}\hat{A}$. Numerical computation can be considerably accelerated by (i) selecting the plane wave basis, which diagonalizes the Green's function operator for the multilayer geometry, and/or (ii) exploiting degeneracies due to azimuthal symmetry about the focal axis. The calculation reduces to inversion of dyads at each spatial frequency, without need to explicitly form the full system matrices. This inverse filtering process is closely related to time-reversal and can be generalized to transparent media by allowing the material loss to asymptotically approach zero.

Consider a two-dimensional geometry where the material has a refractive index n=2. For incident s-polarized radiation, Equation 4 can be numerically solved to obtain a source that focuses to a line at a 4λ/n distance. A linear metasurface can be used to shape a normally incident plane wave such that the exiting field matches the solution. The required impedance values of the passive elements can be solved by using a point-matching method. The line width of the focal spot can be subwavelength, such as 0.42λ full-width half-maximum (FWHM). To verify that the focusing effect is due to phase (not amplitude) modulation of incident wave, the passive elements can be removed such that the surface acts as a grated aperture. The focal spot for the grating is not subwavelength (~λ); the intensity at the focal point is also decreased by a factor of four when the passive elements are removed. The physics underlying the lensing effect is substantially different from near-field focusing devices. Unlike near-field plates, which focus evanescent waves at a strictly subwavelength distance (typically less than λ/10), the immersion lens' focusing ability results, at least in part, from conventional interference between propagating waves and, as a result, the focal plane can be many wavelengths away. The enhanced resolution of our lens follows from the shaping of the near-field phase profile, which couples the incident wave to forbidden angles on interaction with material, rather than the near-field interference effects of near-field plates. Because the focusing is not subject to the intrinsic decay of the near-field, the intensity at the focal spot can be comparable to or higher than the incident intensity. As with solid immersion lenses, the focusing resolution remains subject to the diffraction limit, although the spot size is a function of the material rather than the free-space wavelength.

Next, consider a three-dimensional geometry where a planar source is positioned a subwavelength distance (λ/15) above a material whose refractive index at microwave frequencies approximates biological tissue (real part n=8.8). Due to symmetry about the focal axis, the polarization of the fields at the focal point can be arbitrarily specified. Setting the electric field to be linearly polarized in the x direction, the solution to Equation 4 can be a surface wave consisting of concentric ring-like currents around the focal axis. In air, the resulting fields are evanescent and non-stationary, propagating in-plane towards the focal axis. The intensity profile at the source plane is significantly non-zero only within a finite circular region. The radius of this region defines an effective aperture size that is directly related to the loss in the material system and the depth of focus. At the focal plane in the material, the field converges to a spot of width λ/11, measured FWHM, at a distance of about 2.3λ/n (wavelength in material) from the source plane. Although the wave originates in air, the spot size approaches Abbe's diffraction limit $\lambda/(2n \sin \theta_{ap})$ in homogenous material, where $\theta_{ap}$ is the half-angle the aperture subtends the focal point, due to the source's ability to access forbidden wave components.

In sum, FIG. 14 shows a midfield plate with the functionality of a solid immersion lens. The enhanced focusing resolution of the device results, at least in part from the ability of metasurfaces to control the near-field with sub-wavelength resolution on interaction with dielectric material. At optical frequencies, planar immersion lenses can be implemented with closely-spaced plasmonic antennas or dielectric resonators, with mutual interactions accounted for by tuning the properties of optical "lumped" elements. By incorporating subwavelength structures that interact with the magnetic field component of incident radiation, the metasurface could also modify the optical impedance, allowing reflection at the interface to be eliminated. As the fabrication of the metasurface is simple and planar in nature, the metasurface-based lens can be integrated into complex systems, such as nanophotonic chips or conformal biomedical devices.

In the variation shown in FIG. 14, the midfield plate may comprise of an array of curved sub-wavelength structures 1402, 1404, 1406, 1408, 1410, 1412, 1414, and 1416, and a subwavelength dipole 1018. These may be nested to form a bulls-eye-like pattern, as shown. The choice of the structures is configured to produce propagating fields converging to a subwavelength spot in tissue, as described in more detail above. In other variations, the midfield plate may comprise slots instead of metal strips, having the same configuration as shown in FIG. 14. FIG. 10A shows a top view of the midfield source in FIG. 15. Because the midfield source of FIG. 14 comprises more excitation ports than the midfield source of FIG. 15, it may be more invariant to the characteristics of the tissue in between the source and an implant, although the midfield source of FIG. 15 may work well in a wide range of materials.

Excitation Ports

The midfield plates described herein may be configured to manipulate evanescent fields produced by a power source. In some variations, the subwavelength structures of the midfield plates may be excited by excitation ports, as described briefly above. In some variations in which the midfield plate comprises more than one subwavelength structure, each subwavelength structure may be excited by a separate excitation port. In other variations in which the midfield plate comprises more than one subwavelength structure, a single excitation port may excite more than one subwavelength structure.

The excitation port may comprise a radio-frequency port. A radio-frequency signal may be generated by a signal generator (e.g., an oscillator). The radio-frequency signal may have any suitable frequency. In some variations, the frequency may be between about 800 MHz and about 1 GHz. In other variations, the frequency may be between about 2.3 GHz and about 2.5 GHz. As described above, the optimal frequency for efficient power transfer may depend on the material located between the midfield source and the receiver coil. For example, in the example of a chest wall structure, the optimal frequency may be about 1.6 GHz. In some variations, the frequency of the signal may be adjustable. Adjusting the operating frequency of the source may allow for adjustment of the power received by an implant, and/or may allow the midfield source to be used for implants located within different materials and at different locations within materials.

In some variations comprising more than one excitation port, the radio-frequency signal may be divided into multiple radio-frequency signals, for example, using a power divider (e.g., a Wilkinson power divider) on a control board. In some variations, the radio-frequency signal may be divided symmetrically into each of the multiple radio-frequency signals, but need not be. It should also be appreciated that rather than dividing a single radio-frequency signal into multiple radio frequency signals, the device may comprise multiple signal generators. Each radio-frequency signal may be transmitted via cables (e.g., semi-rigid coaxial cables) from the control board to each radio-frequency port. The signals may additionally or alternatively be fed through a phase shifter (e.g., analog 400°, +3.5/−2.0° error) with controllable phase and/or then amplified (e.g., gain 14 dB). This may produce controlled phase and amplitude signals at each radio-frequency port.

Figure 12A:
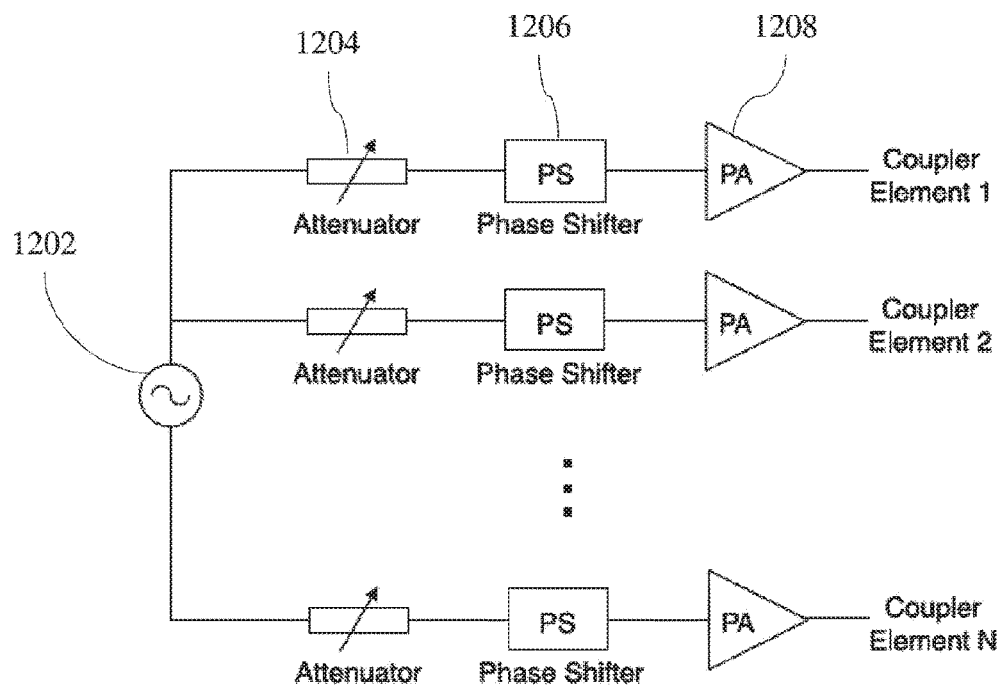
FIGS. 12A-12B show architectures for multiple excitation ports.
Figure 12B:
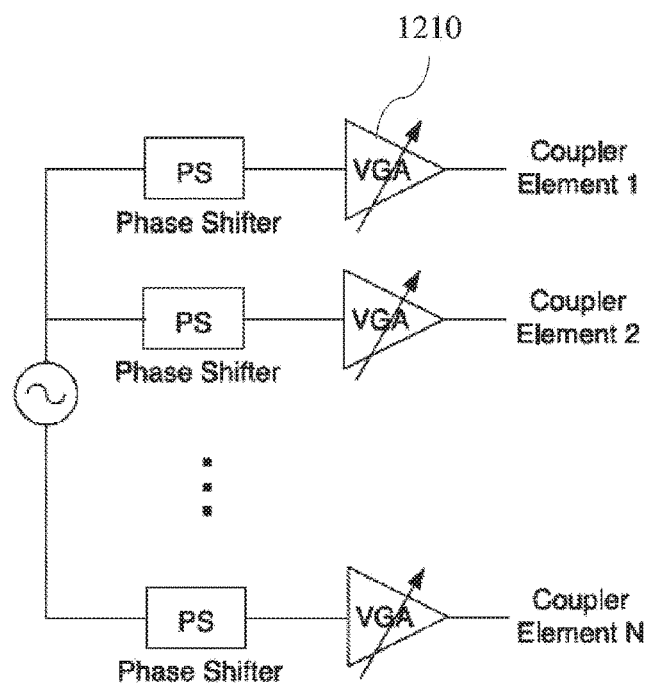
Figure 21A:
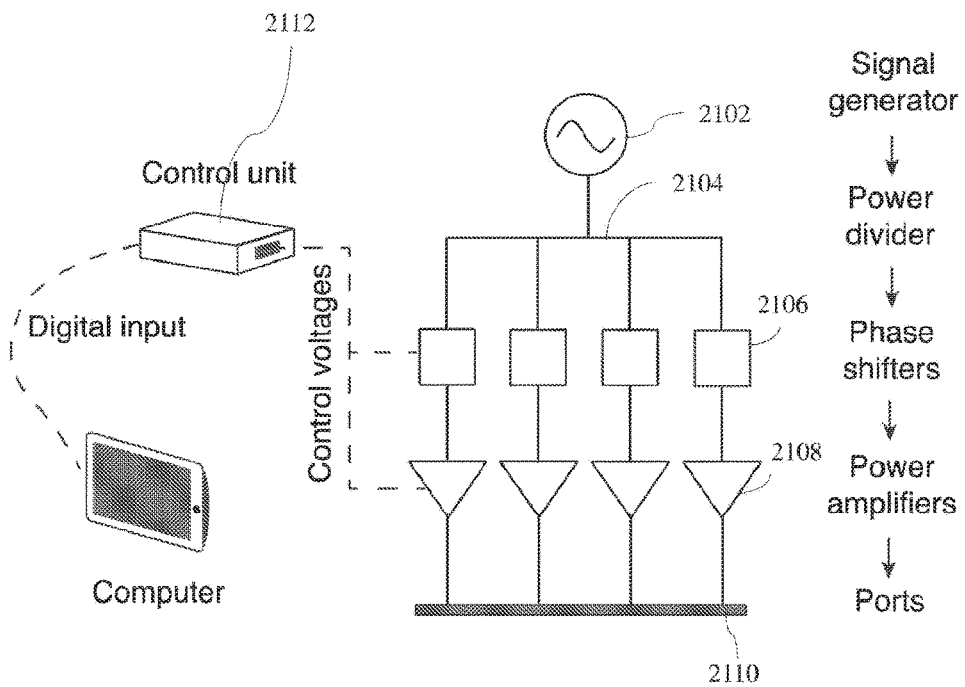
FIGS. 21A-21B show an architecture for a controller of a midfield source.
Figure 21B:
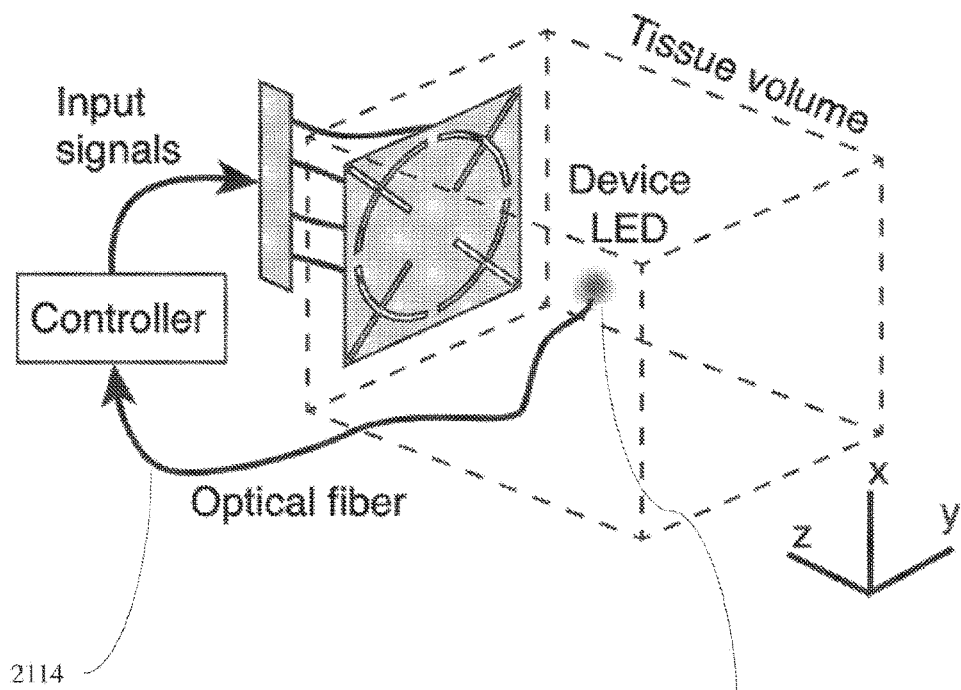

Two example architectures for multiple excitation ports are shown in FIGS. 12A-12B. In the architecture shown in FIG. 12A, the signal generated by the signal generator 1202 may be divided, and then each divided signal may be fed through an attenuator 1204, which may have variable controllable attenuation settings. The signals may then be fed through phase shifters 1206 and amplifiers 1208. The architecture shown in FIG. 12B may be able to produce the same controlled phase and amplitude signals, but with fewer components, by combining the amplifier and the amplitude control element into a single component 1210. FIGS. 21A-21B, described in more detail below, also shows another schematic of a similar architecture for multiple excitation ports 2110.

In some variations in which the midfield source comprises more than one subwavelength structure, two or more subwavelength structures may be excited by a single excitation port. That is, the excitation for each subwavelength structure may not be independent. This may be accomplished by conveying the signal from one radio-frequency port to multiple subwavelength structures, for example, via a microstrip. For example, FIGS. 13A-13B show an example of a source having subwavelength structures similar to those described with respect to FIG. 9B, having a linear slot 1302 and a curved slot 1304 intersecting near their midpoints, wherein the four subwavelength structures described above are excited using the same single excitation port 1306. A ring shaped microstrip transmission line 1308 may be located underneath a ground plane 1310, separated by a dielectric (e.g., air or a substrate 1312). Each point on the microstrip transmission line 1308 may have a different phase. By adjusting the dimension of the microstrip transmission line 1308, multiple subwavelength structures (e.g., four subwavelength structures as shown) may be excited with excitation port 1306.

While the signal generators described above are voltage sources, in other variations, one or more subwavelength structures may be excited by a current source. In yet other variations, the voltage source or current source may be replaced by a reactive element such as a resistor, a capacitor, an inductor, or a combination of these elements. In these variations, the subwavelength structure may be excited by a plane wave or a waveguide. As such, the ratio of the voltage to current may be fixed at the location of the reactive element instead of having a fixed current or a fixed voltage.

Real-Time Dynamic Focusing

Figure 20:
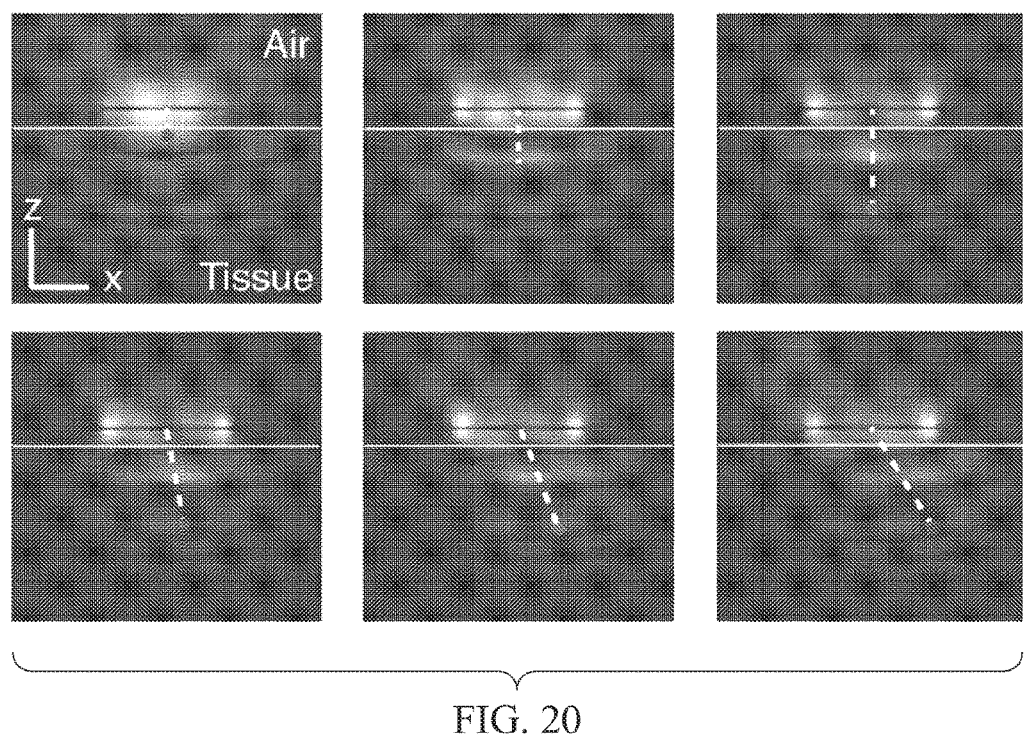
FIG. 20 shows field patterns with spatially shifted focal points created by adjusting the relative amplitude and phases between the port signals in the midfield source of FIG. 15.

In some variations of the midfield sources described here, the focal region may be dynamically shifted without mechanical reconfiguration of the source, using the degrees of freedom provided by the amplitudes and phases of the input port signals. This may be useful in clinical applications in which the source may be used to power implantable devices configured to interact with organs in rhythmic motion (e.g., due to breathing or heartbeat), or implantable devices configured to move inside the body. In order to shift the focal region, the excitation of individual subwavelength structures may be reconfigured in real-time, enabling various field patterns to be synthesized, including those with spatially shifted focal regions. FIG. 20 illustrates field patterns with spatially shifted focal points designed by adjusting the relative phases between the port signals. The upper diagrams in FIG. 20 show formation of a propagating wave in a direction directly below the source. The lower diagrams in FIG. 20 show adjustment of the focal point.

FIGS. 21A-21B show a possible architecture for a controller of a midfield source comprising four excitation ports. As shown in FIG. 21A, a radio-frequency signal may be brought from a signal generator 2102 and may be divided symmetrically into multiple radio-frequency signals through a power divider 2104, such as a Wilkinson power divider. Following power division, the signals may be connected to parallel stages for variable attenuation, phase shifting via elements 2106, and amplification via elements 2108. This may produce controlled phase and amplitude signals at each excitation port 2110. In other embodiments, following power division, the signals may be connected to parallel stages for phase shifting and variable amplification.

The phase shifters 2106 and 2108 may be controlled by a control unit 2112. In some variations, a "greedy" phase search algorithm may be used to change the phase and/or magnitude settings in each element of the midfield coupler so as to dynamically shift the focal region. In some variations, the algorithm may be based on closed-loop feedback, which may be relayed over an optical fiber 2114, as shown in FIG. 21B. In other variations, the implant may comprise a wireless transceiver, which may enable an untethered realization of closed-loop feedback and other related control algorithms. For example, the feedback may be based on detected power levels of received wireless energy by the implant, as described in more detail below. Based on the power measurement feedback from the implant module, the adjustments may be made automatically and in real time to optimize wireless power transmission between the source and the implant.

Figure 22A:
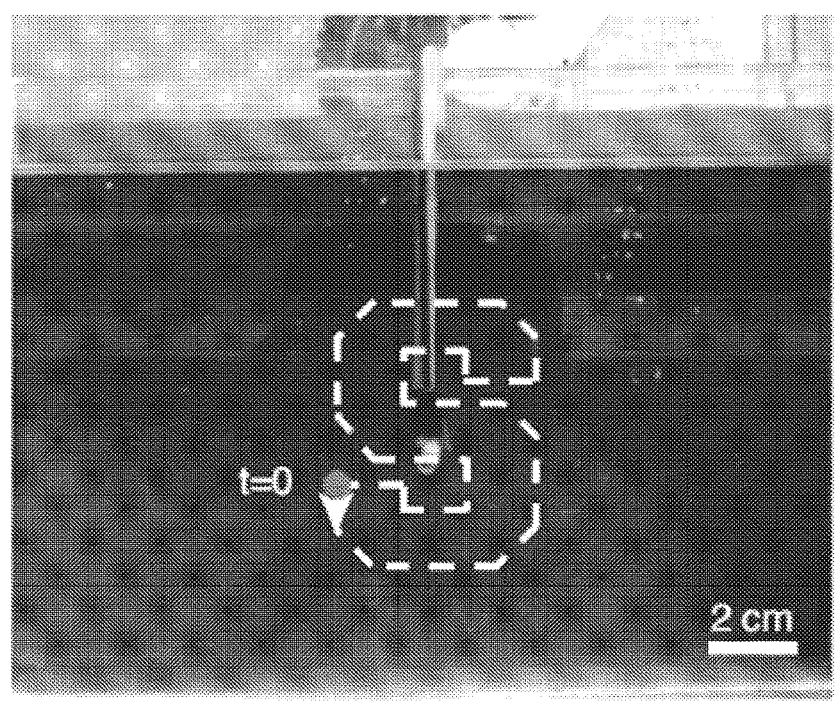
FIGS. 22A-22E show the effect of real-time dynamic focusing.
Figure 22B:
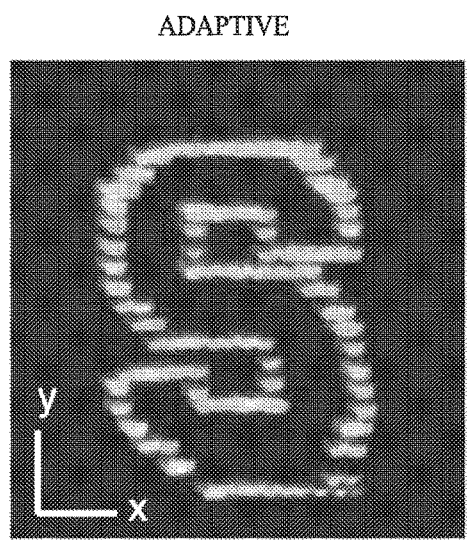
Figure 22C:
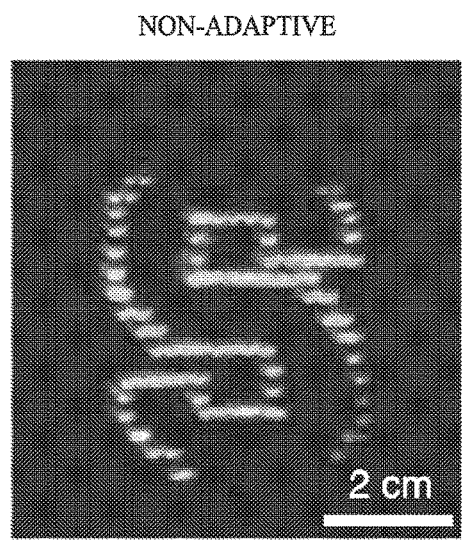
Figures 22D, 22E:
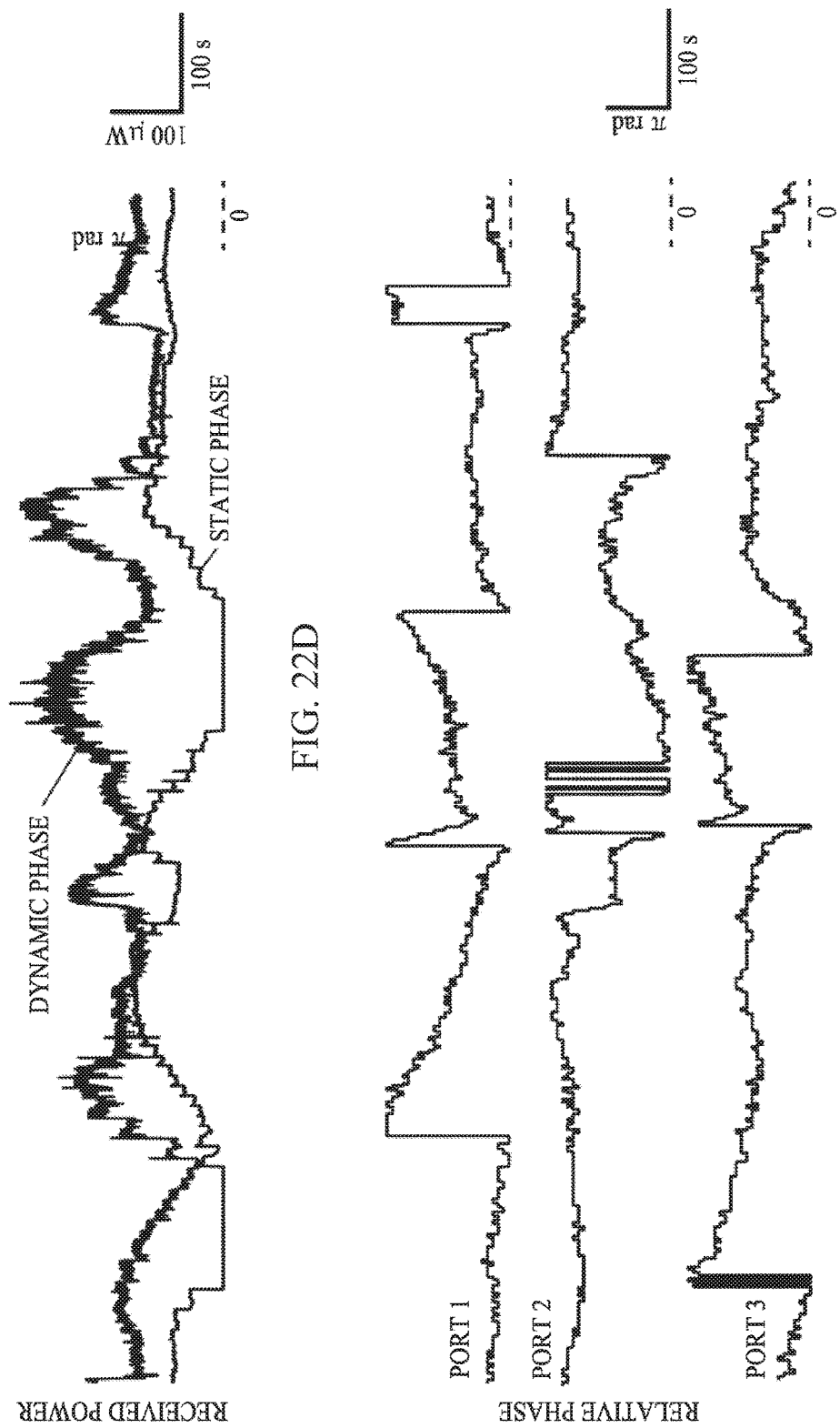

An example of the effect of such an adaptive algorithm is shown in FIGS. 22A-22E. To generate the images shown there, the implant 2216 comprising an LED, shown in FIG. 21B, was moved in an "S" shaped trajectory within a liquid solution whose properties mimicked muscle tissue, as illustrated in FIG. 22A. FIG. 22B shows the strobed position of the LED when a real time control algorithm, such as one described above, dynamically tracked for motion. FIG. 22C shows the strobed position of the LED without dynamic focusing. As can be seen by comparing FIGS. 22B and 22C, the field pattern is static and focused at the center in the non-adaptive case as compared to the adaptive case. Over the "S" shaped trajectory of motion, the adaptation eliminated dark regions that occurred in the static case, indicating a coverage area much wider than that intrinsic to the focal region. The effect of the adaptive algorithm can also be seen in FIGS. 22D and 22E. FIG. 22D shows the power received by the implant, as measured by the flashing rate of the LED. As can be seen, the dynamic phase adaptation algorithm enables higher levels of power to be transferred as the device moves. FIG. 22E shows the phase of each port, relative to a phase stationary port 4, controlled by the algorithm as the implant is in motion.

Internal Module (Implant)

Also described here are implants that may be configured to receive power from a midfield source as described herein. In some variations, the implants may be configured to provide stimulation (e.g., electrical stimulation) to a target site (e.g., a targeted nerve, muscle, or tissue region), described in more detail below. Additionally or alternatively, the implants may be configured to perform a sensory function at a target site, as described in more detail below.

Midfield sources may yield a highly oscillatory electric current density that may force the output field to converge on a subwavelength spot, creating a high-energy density region deep in tissue. Inside this region, a power-harvesting structure in an implant may be able to be made extremely small. Because the system may operate in the midfield region, the implant may mostly harvest energy from the transverse electromagnetic fields (i.e., the oscillation direction of the field is perpendicular to the direction of propagation). This is different from near-field coupling systems, where implants may mostly harvest energy from the axial electromagnetic fields (i.e., the oscillation direction of the field is in parallel to the direction of propagation). The focal region from the midfield sources may be dynamically shifted using the degrees of freedom provided by the amplitudes and phases of the input port signals, as described herein. The implant may incorporate components for received power sensing and wireless communications to enable the realization of real-time dynamic focusing, as described herein.

An implant may comprise of a power receiver, data transceiver, and/or stimulation and sensing components. In some variations, the power receiver may comprise of a coil and one or more AC-DC conversion branches for different output voltage requirements. The data transceiver may comprise of a data receiver, data transmitter, multi-access protocol, and/or an identification, and a digital controller. The stimulation and sensing components may comprise current drivers for both electrical and optical stimulations, sensing frontends for electrical sensing, electrodes, and/or LEDs (light emitting diodes). These components are described in more detail below, but should be appreciated that the implant need not comprise all of these components.

Size and Shape

Figure 23A:
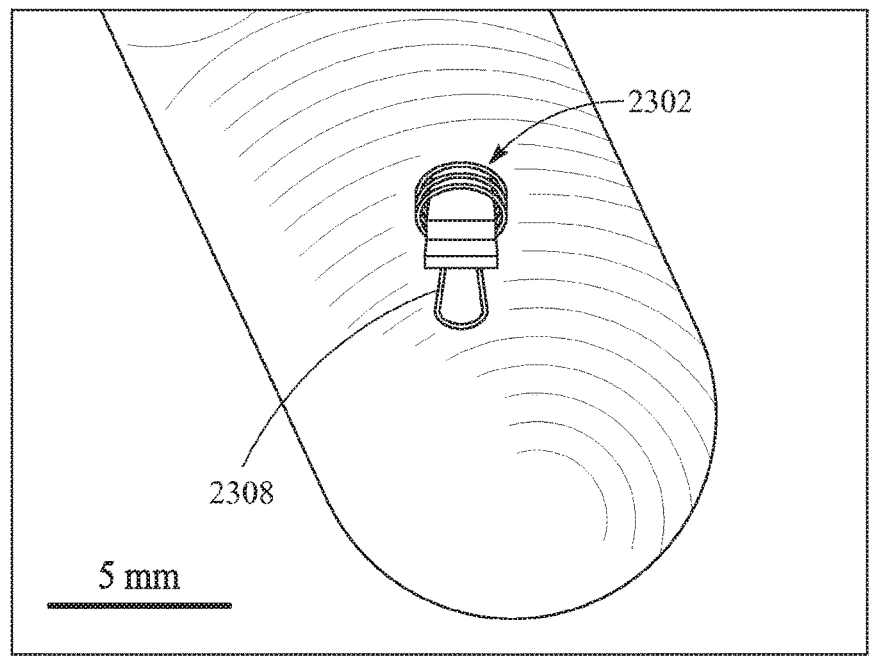
FIG. 23A-23C show photographs of an example of an implant as described here, on a human finger, before epoxy encapsulation next to a catheter sheath for size comparison, and inserted in the lower epicardium of a rabbit, respectively.
Figure 23B:
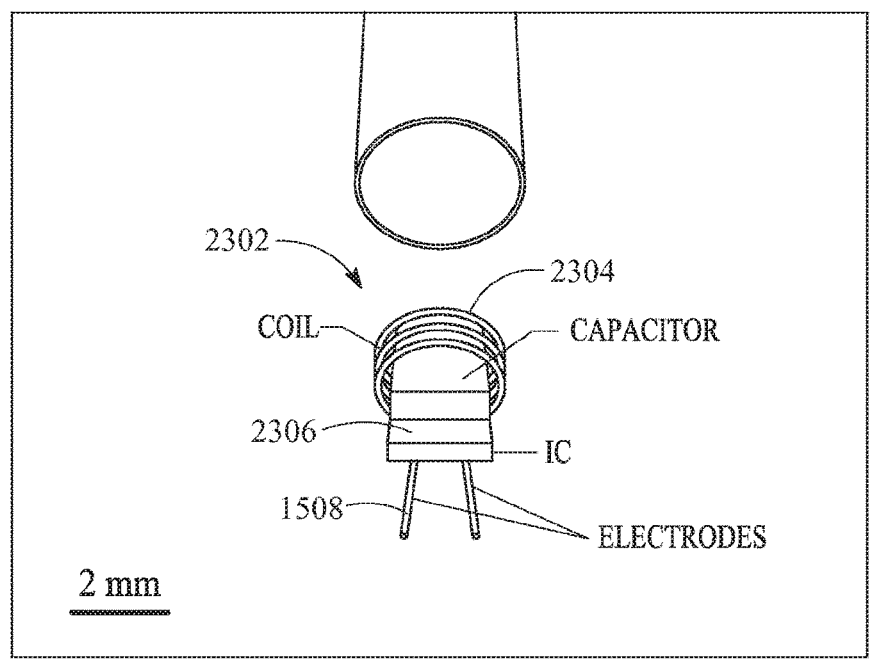
Figure 23C:
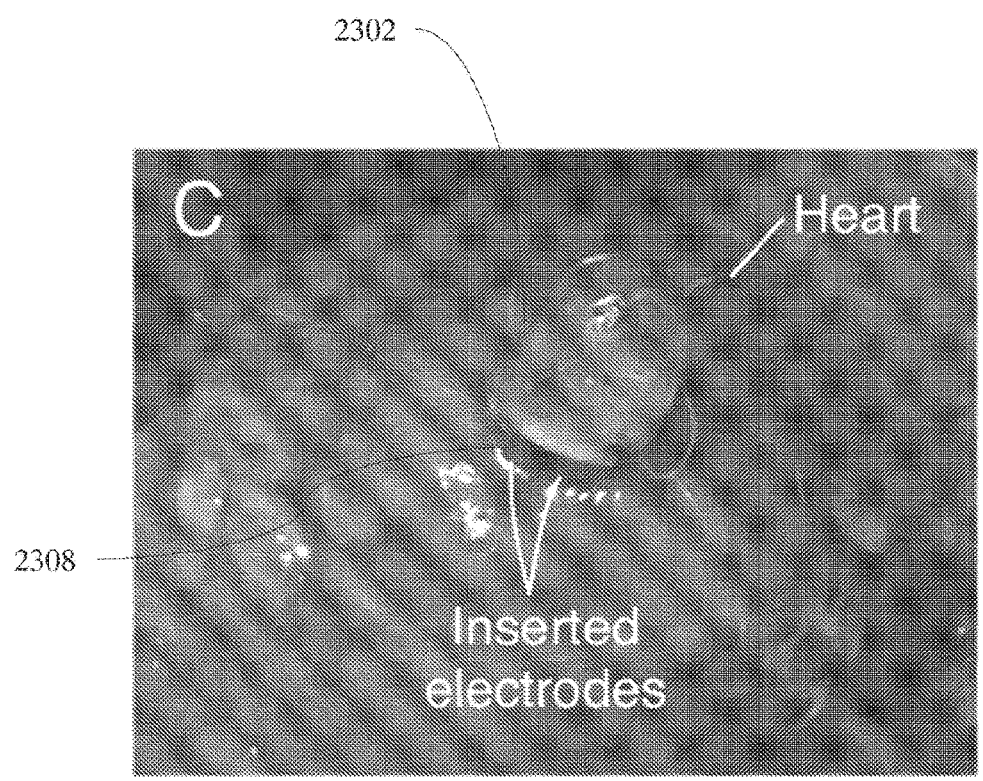

The implants may have any suitable shape and dimensions. In some variations, the implants described here may be configured to fit inside a delivery device, such as but not limited to a catheter or hypodermic needle. In these variations, the implant may be able to be injected into a target site (e.g., a targeted nerve or muscle region) directly without the need for leads and extensions. FIG. 23A shows a photograph of an example of an implant 2302 as described here, on a human finger. FIG. 23B shows the same implant 2302 before epoxy encapsulation next to a 10-French (~3.3 mm) catheter sheath for size comparison. FIG. 23C shows a photograph of the same implant 2302 inserted in the lower epicardium of a rabbit via open-chest surgery. In the variation shown in FIGS. 23A-23C, the implant is a wireless electro-stimulator 2 mm in diameter.

In some variations, the implants may have a cylindrical, semi-cylindrical, circular, or rectangular shape, or the like. In some variations the implants may have a diameter (or greatest cross-sectional dimension) between about 10 μm and about 20 mm, between about 100 μm and about 10 mm, or between about 1 mm and about 5 mm. More specifically, in some variations the implants may have a diameter (or greatest cross-sectional dimension) of about 2 mm. It should be appreciated that in other variations, the diameter (or greatest cross-sectional dimension) of the implants may be greater than 20 mm. In some variations, the implants may have a height of between about 10 µm and about 20 mm, between about 100 µm and about 10 mm, or between about 1 mm and about 5 mm. More specifically, in some variations the implants may have a length of about 3 mm. It should be appreciated that in other variations, the length of the implants may be greater than 20 mm.

In some variations, the implant may be encapsulated in a suitable material. For example, in some variations, the implant may be encapsulated in epoxy. In other variations, the implant may be encapsulated in ceramic or glass. in some variations may comprise anchors or other structures to help secure the implant in place. In some variations, the electrodes may be configured to be used fixation, in addition to stimulation and/or sensing. For example, the electrodes may comprise barbs, as shown in FIG. 23A. In other variations, the electrodes may comprise a screw shape, which may be able to be screwed into tissue. In other variations, the implant may comprise fixation structures that are not also electrodes. For example, the implant may comprise loops or hooks. Such implants may be able to be fixed to tissue by suturing the adjacent tissue through the loops or hooks.

Coil

The coil may be configured to receive energy from a source (e.g., a spatially adaptable electromagnetic field generated by the sources described herein). The energy may be received by the coil as magnetization, due to induced current in the coil. The coil may comprise any suitable material, such as but not limited to copper, gold, or aluminum. The coil may comprise any suitable number of turns. The number of turns may depend on the frequency of the midfield source. In some variations, the coil may comprise between about 1 turn and about 15 turns. FIG. 23B shows an example of a coil 2304 comprising a multi-turn coil structure comprising 200 µm diameter copper wire wound with an inner diameter of 2 mm.

AC-DC Conversion and Charge Pump

In some variations of implants comprising an AC-DC power conversion mechanism, the AC-DC power conversion mechanism may comprise rectifying circuitry. The rectifying circuitry may be configured to convert energy (e.g., a spatially adaptable electromagnetic field generated by the sources described here) received by the implant (e.g., by a coil as described above) to a DC signal. In some variations, the AC-DC conversion circuitry may be divided into low-voltage and high-voltage domains. This may increase the efficiency of rectification and power management of wirelessly powered implants operating in an electromagnetically weakly coupled regime. In some variations, the implants may comprise a charge pump. In one variation, two diodes (e.g., Schottky diodes) and two capacitors (e.g., 10 nF capacitors) may be arranged in a charge pump configuration. At low frequencies, an additional capacitor may be used in order to match the impedance of the coil and the rectifier. A charge pump and flash control integrated circuit may be placed after the rectifier for up-converting the rectified voltage.

Integrated Circuit

In some variations, the implants described here may comprise an integrated circuit. For example, as shown in FIG. 23B, the coil 2304 may be disposed over and connected to an integrated circuit 2306. In some variations, the integrated circuit may be configured to regulate pulse amplitudes. In some variations, the implants may comprise non-volatile memory. For example, the implants may comprise flash memory, which may be configured to record data such as usage information (e.g., the time of activation and setting of the current deriver), and/or to store measurements from sensors (described in more detail below). In some variations, each implant module may have its own identification tag, such as an identification tag stored in the memory of the implant. In some variations, the implant may comprise a digital core, which may be configured to coordinate the interaction among various components of the implant, communication between the implant and external components, and the multi-access protocols, as described below.

Energy Storage Component

In some variations, the implant may comprise an energy storage component. For example, the implant may comprise a rechargeable battery. The rechargeable battery may be configured for temporary energy storage, and/or for use as an efficient charge pump for power management circuitry. In some variations, the rechargeable battery may comprise a thin film battery. In some of these variations, the thin film battery may be stacked, which may allow for increased energy density. In some other variations, the rechargeable battery may comprise a lithium battery. Energy storage components may enable the implant to be operated without continuous coupling to an external power source as described herein. The external power source may be used to charge the implant, which in some variations may be able to be charged with only a few minutes to tens of minutes of wireless charging per week or month.

Sensors

Because the power levels deliverable to the implants by power sources as described herein may exceed requirements for microelectronic technologies, more sophisticated functions may be implemented, such as real-time monitoring of chronic disease states or closed-loop biological sensing and control by the implant. In some variations, the implant may comprise one more sensors. In some variations, the sensors may include, for example, temperature sensors. In other variations, the sensors may comprise optical sensors and/or imaging devices. In yet other variations, the implants may comprise chemical, pressure, oxygen, pH, flow, electrical, strain, magnetic, light, or image sensors. In some variations, the sensors may allow the depth at which the device is operating to be determined. In some variations, the sensors may comprise one or more electrodes.

In variations in which the implant comprises one or more sensors, the implant may comprise one or more pre-amplifiers, analog-to-digital converters, and/or drivers for the one or more sensors. In variations having analog-to-digital converters, the analog-to-digital converters may be used to discretize signals from pre-amplifiers. In some variations, the output signals from the analog-to-digital converters may be stored in non-volatile memory of the implant (as described in more detail above), or in other variations may be sent to the source or other external component via a radio-frequency modulator (as described in more detail below).

In variations in which the implant comprises one or more sensors, the sensors may be configured to provide feedback to the source or to a user. For example, in some variations the implant may comprise one or more sensors configured to detect the instantaneous power level received by the implant. This information may be sent via a data transmitter (described in more detail below) to the source. This may allow for adaptive focusing of the focal region of the field, as described in more detail herein. In other variations, the information from the sensors may be provided to a user, for example via a user interface such as described herein. In some variations, the data may be further analyzed or stored outside of the implant. Information from the sensor or sensors may, for example may allow for wireless real-time monitoring, diagnosing, and/or treatment of patients.

Stimulation

In some variations, the implants described herein may be configured to deliver a stimulus to tissue. The stimulus may be any suitable type, such as but not limited to electrical, optical, chemical (e.g., the implant may be configured for drug delivery), or mechanical. In variations in which the implants are configured to deliver an electrical stimulus, the implant may deliver the electrical stimulus via one or more electrodes. The implants may comprise programmable current drivers, which may allow for a range of stimulus parameters (e.g., for electrical stimuli, intensity, duration, frequency, and shape) to be delivered. In some variations in which the system comprises a user interface as described herein, the programmable current drivers may be programmed via the user interface (e.g., via a wireless data link to the implant). As shown in the variation in FIGS. 23A-23C, in some variations the implant may comprise two electrodes 2308. The two electrodes 2308 may be located on one side of the implant 2302, such that they may be inserted into tissue, as shown inserted in the lower epicardium of a rabbit in FIG. 23C.

Figure 24A:
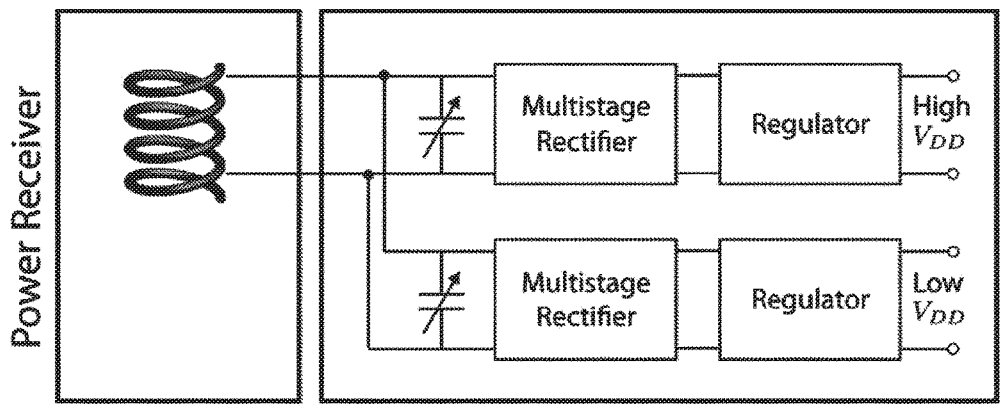
FIGS. 24A-24C show circuit schematic for a power receiver, a data transceiver, and a stimulator and sensor, respectively.
Figure 24B:
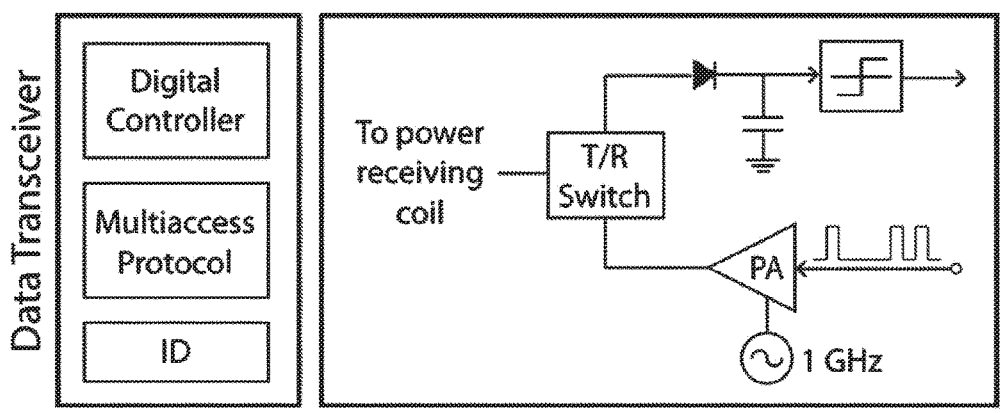
Figure 24C:
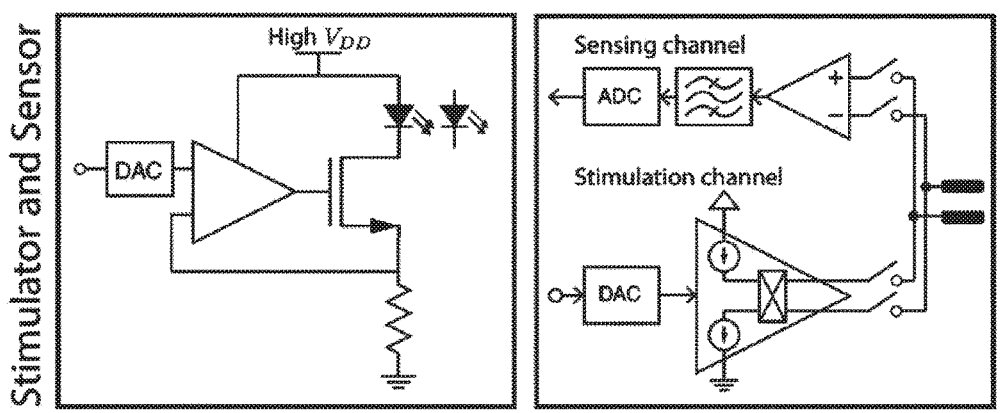

FIG. 24A shows a circuit schematic for a power receiver (an implant). FIG. 24B shows a circuit schematic for a data transceiver. FIG. 24C shows a circuit schematic for a stimulator and sensor.

Figure 25A:
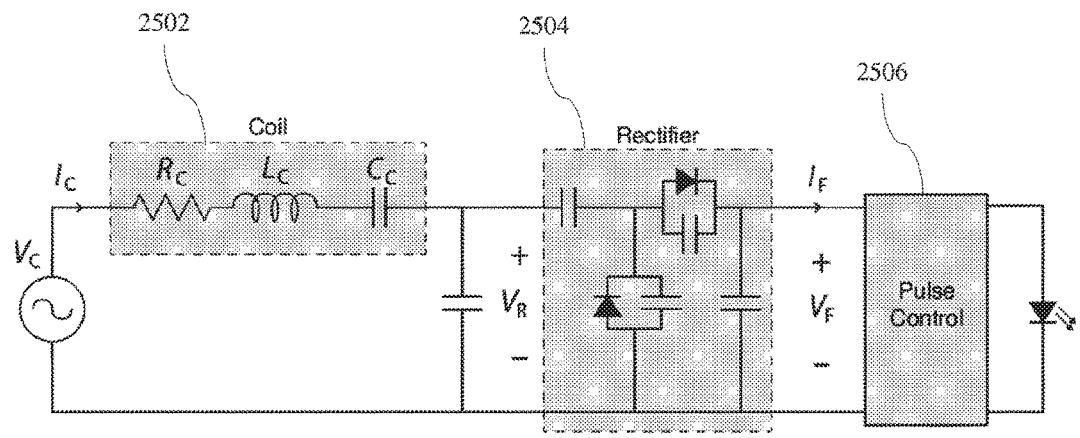
FIGS. 25A-25C show circuit schematics for an implant configured to stimulate tissue.
Figure 25B:
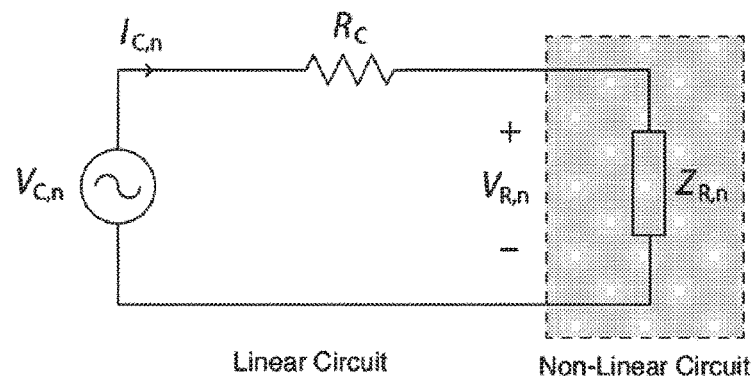
Figure 25C:
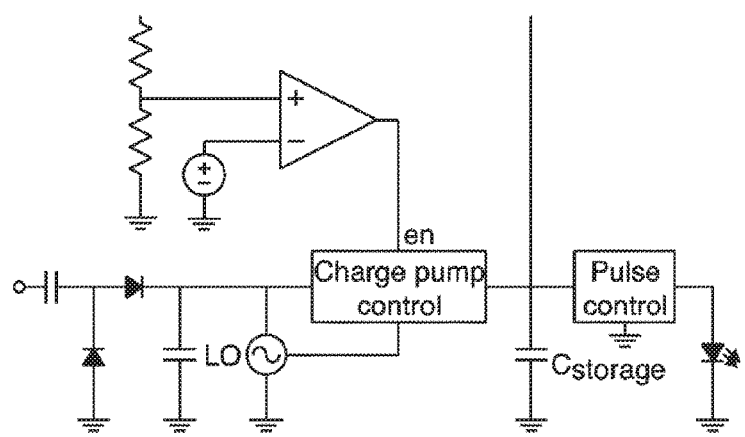

FIGS. 25A-25C show circuit schematics for an implant that may be configured to stimulate tissue (e.g., an implant configured as a pacemaker). FIG. 25A illustrates a lumped circuit model of the receiver. As shown, the AC voltage Vc generated across the coil 2502 by the source (as described in more detail herein) is converted to DC power through the rectifier circuitry 2504. FIG. 25B illustrates the equivalent circuit at the nth reference power level when the circuit is at resonance. FIG. 25C illustrates the detail of the circuit components. As shown, the implant may comprise a rectifier, a charge pump, a pulse control integrated circuit, a storage capacitor, and an LED. In other variations, the LED may be replaced by a pair of electrodes, which may be configured for electrostimulation. In some variations, the rectifier circuits may comprise with two diodes and two capacitors arranged in charge pump configuration. A charge pump may be placed after the rectifier for upconverting the rectified voltage, for example, from 0.7 V to 2 V, necessary to drive the LED or electrodes. Charge may be temporarily stored on a capacitor. A pulse control unit may be used to control the pulse frequency and width. In the example shown in FIG. 25A-25C, the circuitry also included a LED configured to encode the power flowing through the pulse control circuitry 2506 via its flashing frequency. The non-linear properties of the rectifier and pulse control unit may enable the unknown parameter $R_C$ to be estimated if the circuit is characterized at two reference flashing frequencies. Once the environment-dependent parameter $R_C$ is known, the transferred power may be estimated. In some variations, the LED in FIGS. 25A-25C may be replaced by a pair of electrodes, which may be configured to stimulate tissue and/or nerves.

Data Transmission

The implant may be capable of wireless data transmission, and in some variations may comprise a wireless data link between the implant and the midfield source or another external component (e.g., an external user interface). The wireless link may be unidirectional or bidirectional, and thus, in some of these variations the implant may comprise a data receiver. The wireless link may be configured to activate the implant (e.g., activate stimulation in variations comprising stimulators), remotely program or configure the implant (e.g., adjust implant settings), and/or receive data from one or more sensors.

The data transmitter of the implanted module may use pulsed radio-frequency modulation. In some variations, radio-frequency modulation may be desirable because conventional load modulation may not work in the midfield due to the low quality factor of the implant antenna, which may lead to poor signal-to-noise ratio and substantial link margin fluctuation. In other variations, non-coherent modulation techniques such as amplitude shift keying and frequency shift keying may be used for ease of implementation. To ease detection at the external module, the data and power carriers can operate at different center frequencies. In some variations, the implants may utilize multi-access protocols, which may coordinate the functions of the implant (e.g., such as coordinating multi-site stimulation). In some variations, the multi-access protocols may utilize time multiplexing and frequency multiplexing.

The data rate for the wireless data link may be any suitable rate (e.g., from a few kbps to 10's of Mbps). For example, in some variations the data rate for the downlink from the source to the implant may be a few Mbps or lower, while the data rate for the uplink from the implant to the source may be higher, such as in the range of 10's of Mbps or higher.

User Interface

In some variations, the systems described here may comprise a user interface, which may be used, for example, by a clinician or patient. Some variations of the user interface may be integrated with the power source, while in other variations the user interface may be separate from the power source. In some variations in which the user interface is separate from the power source, the user interface may comprise a mobile computing device, such as a smartphone, tablet, or wearable computer. In these instances, the system may comprise a wireless or wired communicating link, which may allow for bidirectional communication between the power source and/or the implant and the mobile computing device. This may allow a patient and/or clinician to interface (e.g., receive or input information) with the power source or implant using the display of the mobile computing device.

While the source, implant, and user interface are described here as a system, it should be appreciated that the devices described herein may be used alone or in combination with other devices and systems. It should also be appreciated that the systems described here may be configured based on the particular needs or requirements of the end user. For example, the implants may have a modular design and may be modified to include those components desirable for the intended use. In some variations, all the above building blocks in the implanted module may be integrated into a single die as system-on-chip (SoC) or multiple dies enclosed in a single module as system-in-package (SiP).

Methods/Applications

Also described herein are methods of wirelessly powering implants, such as those described herein, using midfield sources as described herein. The implants described herein may be implanted in any suitable location. In some variations, they may be implanted through minimally invasive procedures, such as via catheter or hypodermic needle. The implants may be implanted in humans or in other animals such as pets, livestock, or laboratory animals such as rabbits, mice, rats, or other rodents. The implants may be used for any number of applications, such as but not limited to muscular stimulation, stimulation/sensing to regulate a patient's heartbeat, deep brain stimulation, drug delivery, and/or biological, physiological, and chemical sensing.

The midfield sources described herein may be used to transfer power to the implant. In some variations, the power received by the implant may be adjusted by adjusting an operating frequency or other parameter of the midfield source, as described in more detail above. Additionally or alternatively, the parameters may be adjusted in real time to modify the focal region of the midfield source, in order, for example, to track movement of the implant.

For example, in some variations the systems described herein may be used for cardiac pacing. In some of these examples, one implant may be delivered into the right ventricle of a patient, while a separate implant may be delivered to the left ventricular epicardium. The implants may be delivered in any suitable manner, such as via catheters through the vasculature (e.g., the implant may be delivered to the left ventricular epicardium via the coronary sinus and coronary vein). These implants may comprise both stimulation and sensing electrodes, which may be configured to apply leadless pacing to the heart. The systems described herein may thus allow leadless biventricular pacing to be achieved with only minimally invasive procedures. This may substantially reduce procedure time and complications.

Figure 23D:
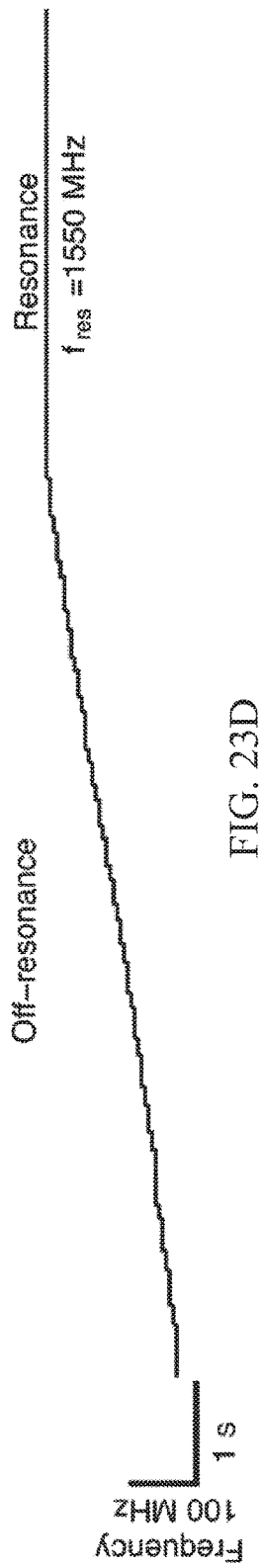
FIG. 23D shows the operating frequency of a midfield source applied to the implant of FIG. 23C.
Figure 23E:
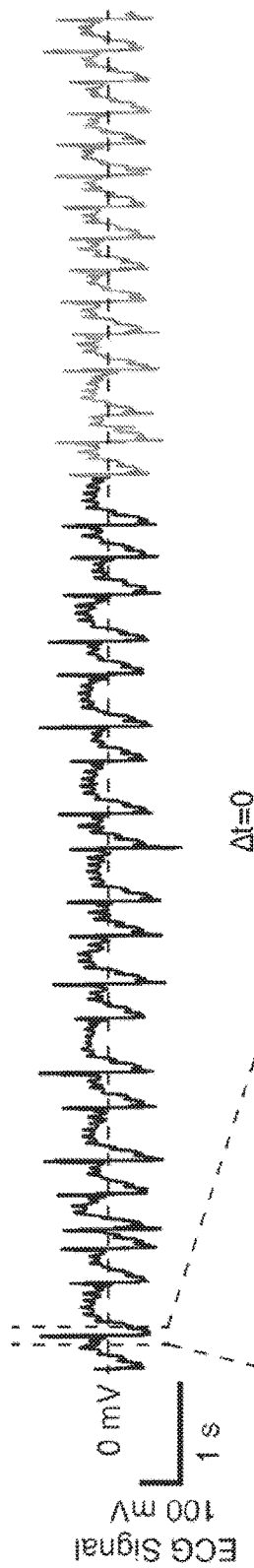
FIG. 23E shows an ECG of the rabbit of FIG. 23C.
Figure 23F:
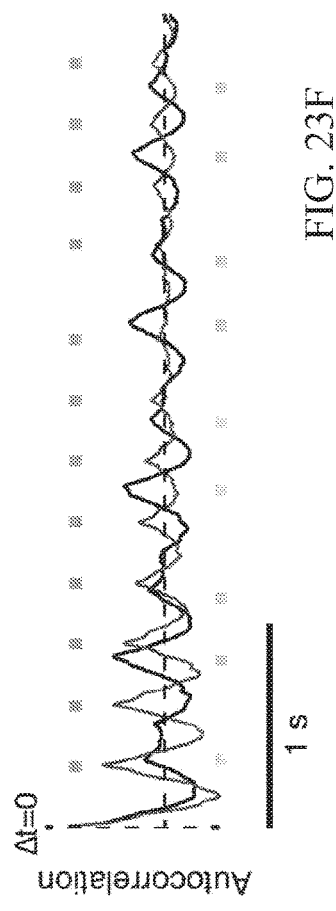
FIG. 23F shows the autocorrelation function of both the off-resonance and resonant sections of the ECG signal of FIG. 23E.

An example of wireless cardiac pacing using a system as described here is shown in FIG. 23C, described in more detail above. After implantation of a wireless electro-stimulator into the lower epicardium of a rabbit as shown in FIG. 23C, the chest was closed. The electro-stimulator device shown in FIG. 23C was about 2 mm in diameter, weighed about 70 mg, and as capable of generating 2.4 µJ pulses at rates dependent on the extracted power. Its characteristic dimension was at least an order of magnitude smaller than existing commercial pacemakers due to the absence of a battery. A portable, battery-powered midfield source shown in FIG. 29 was positioned about 4.5 cm (about 1 cm air gap, and 3.5 cm chest wall) above the implant 2302. The midfield source was used to couple about 1 W of power into the chest, and the operating frequency of the source adjusted to the estimated resonant frequency of the circuit and maintained for several seconds, as shown in FIG. 23D. Cardiac activity of the rabbit was monitored by ECG, shown in FIG. 23E. The cardiac rhythm could be controlled in a fully wireless manner by adjusting the operating frequency. When the operating frequency was coincident with the resonant frequency of the circuit, the pulse amplitudes were sufficient to pace the heart, as indicated by the increased rate and regularity of the ECG signal in FIG. 23E. FIG. 23F shows the autocorrelation function of both the off-resonance and resonant sections of the ECG signal. Peaks in the autocorrelation function are marked with squares.

Similar methods may be applied for any other optical or electrical stimulation task in the body. For example, similar methods may be used to stimulate neurons or muscle cells. For example, similar systems and methods may be used for deep-brain stimulation. Current procedures for deep-brain stimulation involve drilling holes with diameters of over 1 cm in the skull to insert a lead and the extension from the lead to the stimulating module. Due to the invasiveness of the procedure, only a limited number of target sites are generally selected for placing the electrodes. In addition, the leads may not be MRI compatible. By contrast, the implants described herein for use with midfield sources may be injected into the brain via other less invasive routes, and require no lead or extension wire. This may allow for more target sites for stimulation and may be MRI safe. Moreover, multiple devices may be implanted and used for stimulation in a synchronized manner. Additionally, the use of systems as described herein may result in less infection and lower regulatory risk.

As another example, the systems and methods described herein may be used for spinal cord stimulation. Batteries in newer models of spinal cord stimulator are rechargeable due to the high power requirement. However, their powering approaches rely on inductive coupling (or near-field coupling). Since the harvesting components are large in these systems, they can only be placed subcutaneously and not deeper. Therefore, the lead and extension wires in these systems may potentially restrict the location of the electrodes for effective stimulation. Lead dislodgement and infection may be major sources of complications. Because the implants described herein are much smaller, the entire implant may be placed next to the targeted nerve region in the spinal cord and may not require a lead wire. Again, this may result in less infection, less damage to the spinal cord tissue, and more effective stimulation.

As yet another example, the systems and methods described herein may be used for peripheral nerve stimulation. Most current devices support low-frequency stimulation, and only a few support high-frequency low-intensity stimulation, due to the much higher power requirement. The systems described herein may be able to support both modes. In addition, the bidirectional wireless link as described herein may provide the ability to switch between different modes, and to personalize the stimulation paradigms to individual patient.

As mentioned above, the systems and methods described herein may also be used for stimulating muscle cells. For example, the systems and methods described herein may be used to treat obstructive sleep apnea (OSA). The implants described herein may be able to be injected and directly embedded into the muscular tissue near the tongue, and may then be used to deliver electrical stimulation to open the airway of a patient during sleep. Multiple implant modules may be injected into different muscular groups to intensify the muscle contraction. When needed, patients may be able to charge the implants with the midfield source. Additionally or alternatively, the data transmission capabilities may allow for download a time stamp of each OSA episode, which may be able to be sent to a clinician. The implants may also be able to be reprogrammed without removal. In some cases, the reprogramming may be based on the data collected.

When the implants described herein are used to stimulate excitable cells, in some variations they may be used for temporary treatment applications, in which implantation of a long-term implant is undesirable. For example, currently, screening tests are typically performed before a permanent impulse generator is implanted. During the screening test, a patient may receive a temporary, external impulse generator. The generator may connect to an extension and a lead, which may be surgically placed in the body. In this period, the external impulse generator collects patient usage data and efficacy of the treatment. However, an implant as described herein may be injected into the targeted nerve/muscle region, eliminating the need for a temporary generator with leads. In addition, the implants described herein may be used instead of temporary sensing and pacing leads in patients after cardiac surgery.

The systems and methods described herein may also be used for applications other than stimulation of excitable cells. For example, they may be used in medical sensing applications. Battery less implanted sensors are typically passive in nature—that is, there is no active circuitry in the device to condition the sensed signals due to the lack of an efficient wireless powering approach. To compensate for the poor signal quality, a sophisticated and large external reader is generally required. The passivity of the sensors may also limit the stimuli that may be detectable. The midfield sources and implants described herein may allow for the transfer of a substantial amount of power to small implanted modules at nearly any location in the body from a palm-size external module. This enables an array of new sensing applications for continuous monitoring, for example, post-surgery oxygen sensing in the heart and the brain.

As another example, the systems and methods described herein may be used for wireless endoscopes. Current capsule endoscopes have limited battery lifetime, sometimes leading to incomplete small-bowel examination. This limitation may be addressed by the systems described here. In addition, since the implants described here may be able to be significantly smaller than current capsule endoscopes, patients may be able to swallow multiple devices simultaneously. Each device may orient differently in the intestine, and therefore may take images from different angles at the same location, improving the field of view, allowing for improved diagnosis. Finally, the probability of retention may be reduced, avoiding the need for surgical or endoscopic retrieval.

The systems and methods described herein may also be used for implanted drug delivery. Current implanted drug delivery systems are large and are generally cannot be placed sufficiently close to the site at which the drug is needed. An implant as described here may further comprise one or more drug reservoirs. The implant may be injected or delivered via catheter to a target tissue region (e.g., a tumor). The drug reservoirs may be activated to release drug by the midfield source. In some variations, the activation may be controlled by a patient or clinician via a user interface, as described herein.

The systems and methods described herein may also be used in laboratory experiments with lab animals, such as rodents (e.g., mice, rats, etc.). The small size of the implants may allow for monitoring capabilities not previously available or easily implemented. For example, the implants as described herein may be used to monitor or sense parameters and/or provide stimulation. The implants may be, for example, implanted on or near the brain of a rodent to monitor electrical signals. The implant can be wirelessly powered with the midfield source described above, and may be able to be configured to communicate information back to the external module.

Example

Figure 26A:
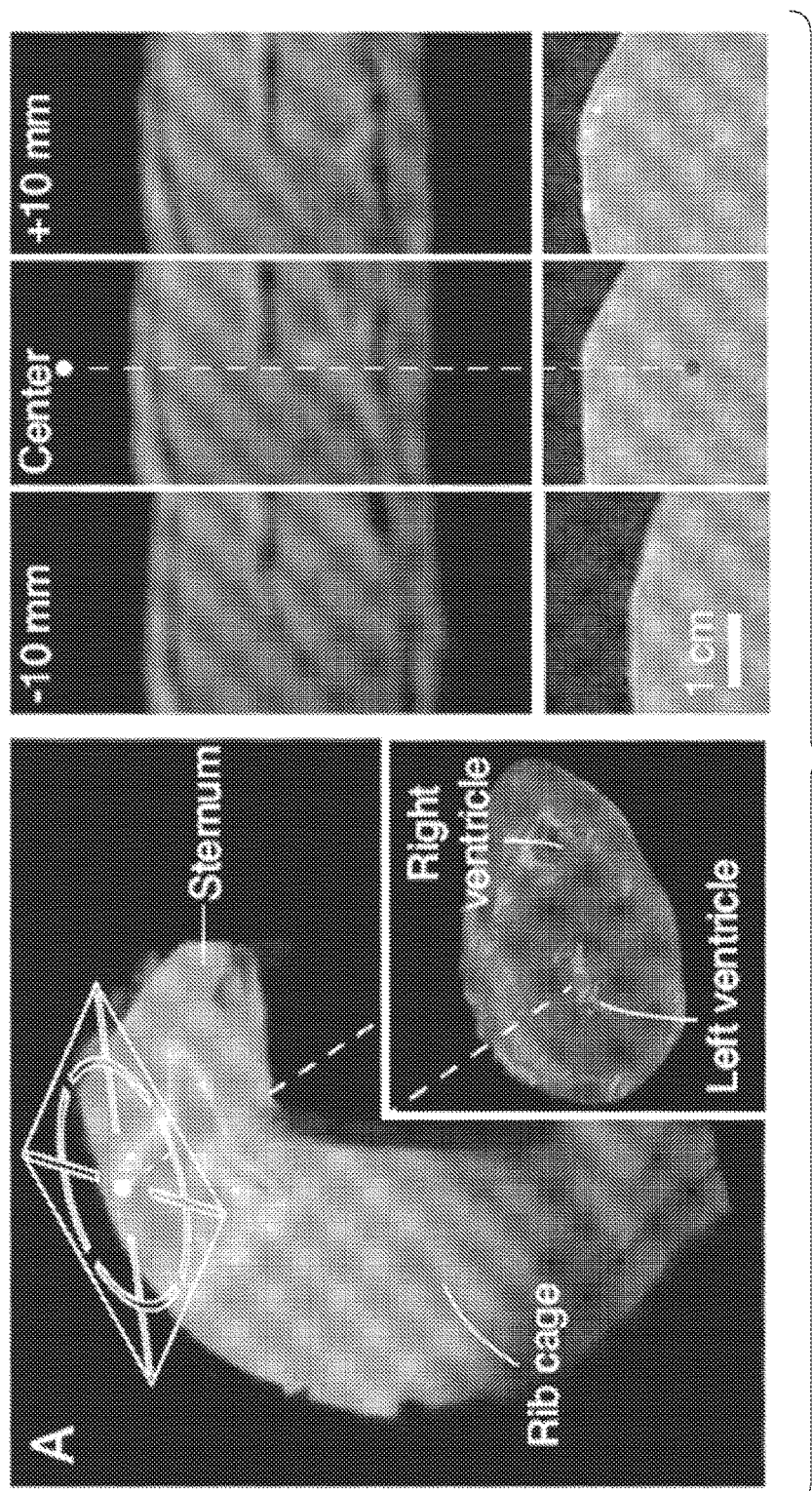
FIGS. 26A-26B show magnetic resonance imaging reconstructions of implant positions within porcine tissue volumes.
Figure 26B:
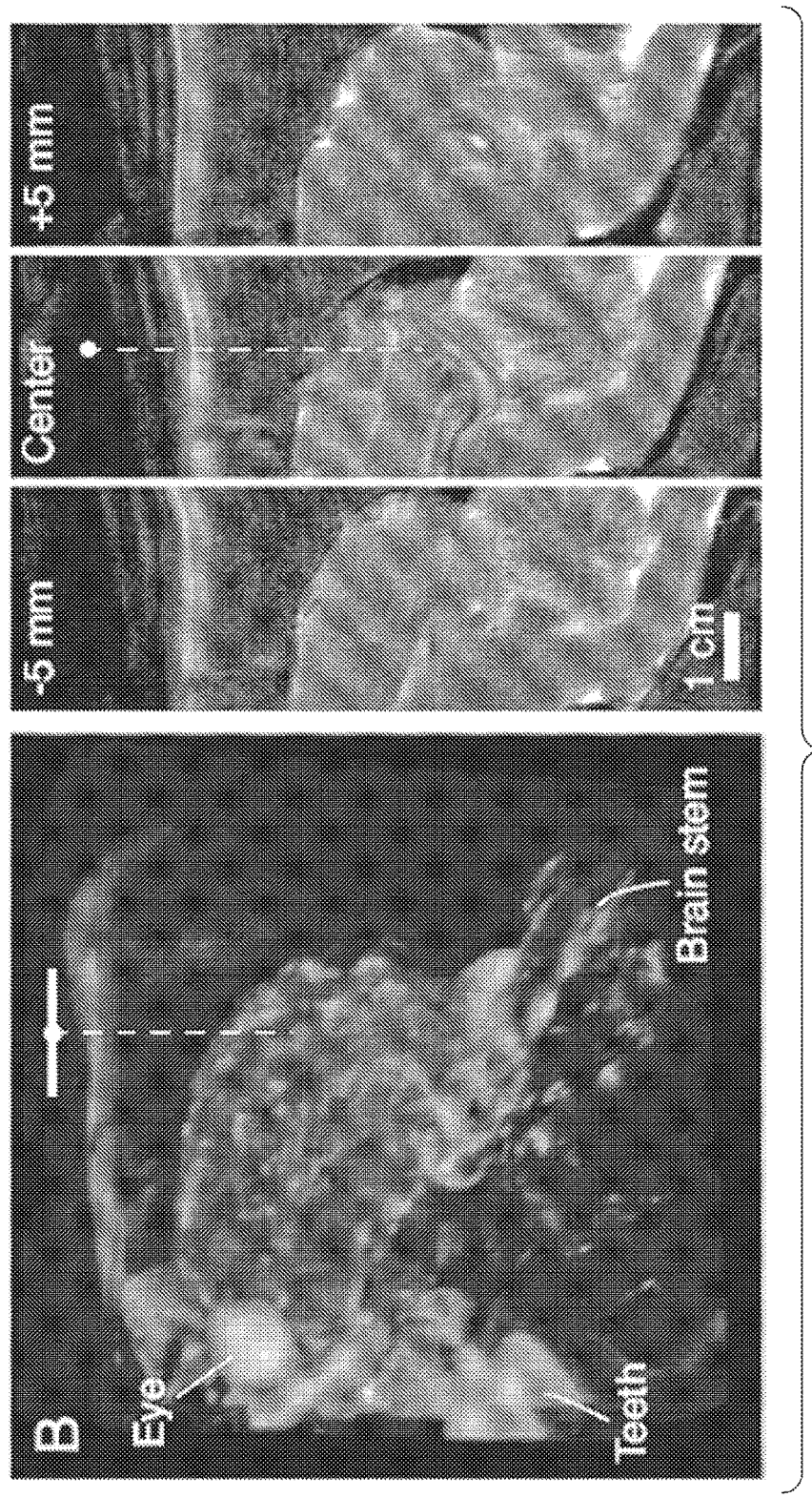

A system as described herein was used in two simulations of power transfer to an implant, using porcine tissue volumes: a first simulating placement in the left ventricle of the heart, and a second simulating placement in the cortex region of the brain. The source and implant were located at least 5 cm apart. FIGS. 26A and 26B show magnetic resonance imaging (MRI) reconstructions of the implant positions within the porcine tissue volumes. FIG. 26A shows an MRI reconstruction of the configuration for power transfer across a porcine chest wall to an implant located on the heart surface. A T2-weighted spin-echo pulse sequence was used to acquire the MRI image, and the image was reconstructed using the OsiriX software package. The source center (white dot) and the coil of the implant (gray dot) were 5 cm apart (1 cm air gap, 4 cm heterogeneous tissue). The fields in FIG. 26A were calculated using a commercial electromagnetic simulator. The patterned metal plate was placed above a tissue multilayer (1 cm air gap, 4 mm skin, 8 mm fat, 8 mm muscle, 16 mm bone, 144 mm heart) and the fields were calculated by a time-domain solver.

FIG. 26B shows an MRI reconstruction of the configuration for power transfer to an implant located in the lower cortex region of a porcine brain. T2-weighted fast spin-echo was used to acquire the MRI image, and the image was reconstructed using the OsiriX software package. In the configuration shown there, the source-implant separation was 5.5 cm. When coupling 500 mW into tissue (approximately the output power of cell phones), the power transferred to the coil of the implant was measured to be 195 µW for the implant located on the heart surface, and 200 µW for the implant located in the lower cortex. The received power remained substantial (~10 µW) even when the operating depth (i.e., the distance between the source and the implant) was increased to 10 cm.

These levels are far greater than requirements for advanced integrated circuits. To illustrate the range of applications available with performance characteristics reported in the main paper, Table 1 below describes the power requirements of selected state-of-the-art integrated circuits. The table is not exhaustive, but is representative of existing solid-state circuit capabilities in the microwatt power regime. Most of these devices are currently powered with either wire tethers or large (>2 cm) near-field coils.

TABLE 1

Fabrication process and power consumption of selected integrated electronics

| Function | Fabrication Process | Power Consumption |
| --- | --- | --- |
| Neural local field potential sensing | 0.8 µm CMOS | 4.5 µW per channel |
| Optogenetic stimulation | 0.8 µm HV CMOS | 400 µW |
| Neural recording | 0.18 µm CMOS | 0.73 µW per channel |
| Pacemaker | 0.5 µm CMOS | 8 µW |
| Intracardiac impedance measurement | 0.18 µm CMOS | 6.67 µW per channel |
| Fluorimeter | 0.6 µm CMOS | <1 µJ per measurement |
| Intraocular pressure sensor | 0.18 µm CMOS | 1.44 µJ per measurement |
| Temperature sensor | 0.16 µm CMOS | 0.027 µJ per |
| CMOS image sensor | 0.18 µm CMOS | 3.4 µJ per frame |
| Locomotion | 65 nm CMOS | 250 µW at 0.53 cm/s |

In comparison, cardiac pacemakers consume about 8 µW. Provided that the fields can be refocused, computational studies show that the performance is insensitive to the fine structure and composition of the intermediate tissue.

The excess energy dissipated over tissue may pose potential safety concerns. The basic metric for radio-frequency exposure is the specific absorption rate (SAR), defined as the power loss integral over a reference volume of tissue. Limits exist on the SAR induced by a source of electromagnetic fields in order to protect against adverse health effects arising from tissue heating. A system is compliant with the IEEE C95.3-2005 standard if (i) the whole-body average SAR is less than 0.4 W/kg and (ii) the maximum local SAR (averaged over 10 g of tissue) does not exceed 10 W/kg. These limits are reduced by a factor of 5 for general public exposure (uncontrolled environments), such as for cell phones.

Figure 27A:
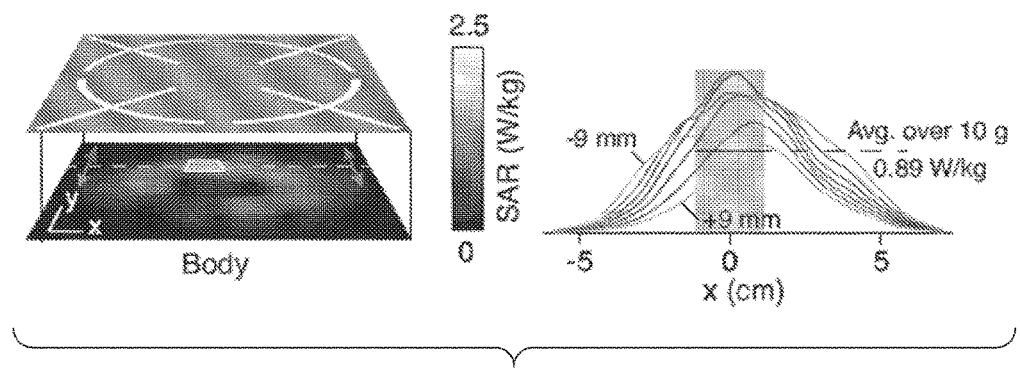
FIGS. 27A-27B shows a specific absorption rate measurement setup.
Figure 27B:
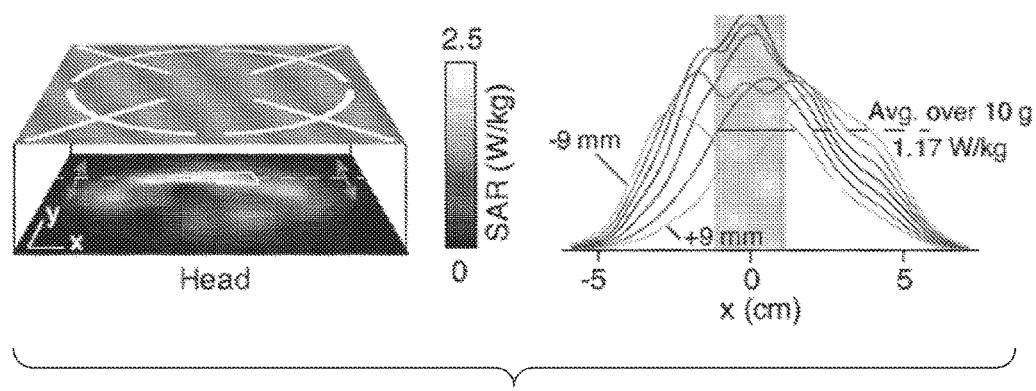
Figure 27C:
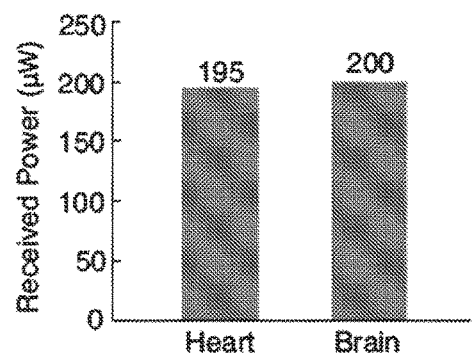
FIGS. 27C-27D show specific absorption rate distribution from the setup of FIG. 27A.
Figure 27D:
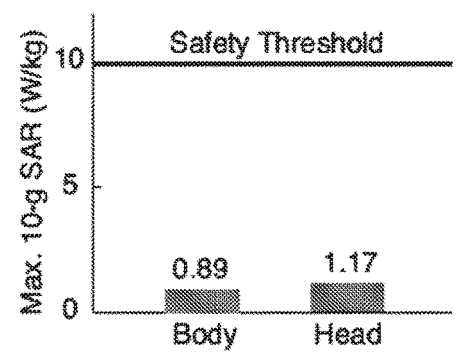
Figure 27E:
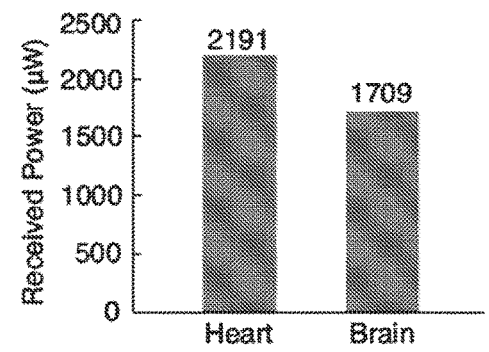
FIG. 27E shows received power when the power coupled into tissue in the setup of FIG. 27B
Figure 27F:
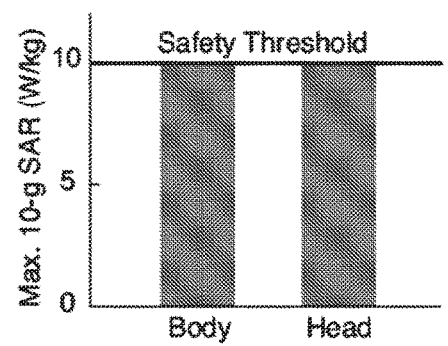
FIG. 27F shows the received power is at or below the maximum permitted level of exposure.

To assess the exposure levels induced by power transfer, a source as described herein was operated over a simulated tissue volume defined by an anthropomorphic fiberglass shell. The spatial distribution of absorbed power was measured by scanning a robotic probe through dosimetric liquids mimicking the body and head, as shown in FIG. 27A. When coupling 500 mW of focused power into tissue, the maximum specific absorption rate (SAR) was found to be 0.89 W/kg for the body and 1.17 W/kg for the head, averaged over 10 g of tissue, as shown in FIGS. 27B and 27C. These levels are far below the exposure threshold for controlled environments, as shown in FIG. 27D. If the power coupled into tissue is allowed to meet the maximum permitted level of exposure, FIG. 27E shows that 2.2 mW and 1.7 mW can be transferred for the configurations shown in FIGS. 26A and 26B, respectively. The low body-averaged absorption (<0.04 W/kg for adult humans) and localized distribution suggest that the power transfer is unlikely to have a meaningful impact on core body temperatures. FIG. 27F shows that the power levels are at or below the safety threshold.

Implantable Midfield Receiver

Previous through tissue wireless power transmission techniques, where the transmitter and receiver are within a wavelength (in air) of each other rely on coupling where the dominant field type in the near field of the transmitter and receiver structures are the same. For example, an external transmitter loop can transmit a magnetic field that is inductively coupled through the magnetic fields to an implanted receiver loop. In another example, an external dipole can be coupled with electric fields to an implanted dipole.

Using a midfield external transmitter, however, an electric field based receiver (e.g., a dipole antenna) can be coupled with a magnetic field (e.g., a tangential H-field) based transmitter. With a strong tangential H-field component, the magnetic field can propagate through the tissue medium. With a midfield transmitter, the electric field and magnetic fields are proportional in the induced propagating waves. A midfield transmitter with a strong magnetic field component can be coupled to an electric field based receiver.

Previous receiver antennas that were coupled to midfield transmitters include a helical structure. In contrast to the helical structure which requires a three dimensional production technique, a dipole can be easily manufactured, such as on a planar surface. Also, the dipole can be more easily integrated into an injectable (e.g., long and thin) implant than the helical structure.

Figure 29:
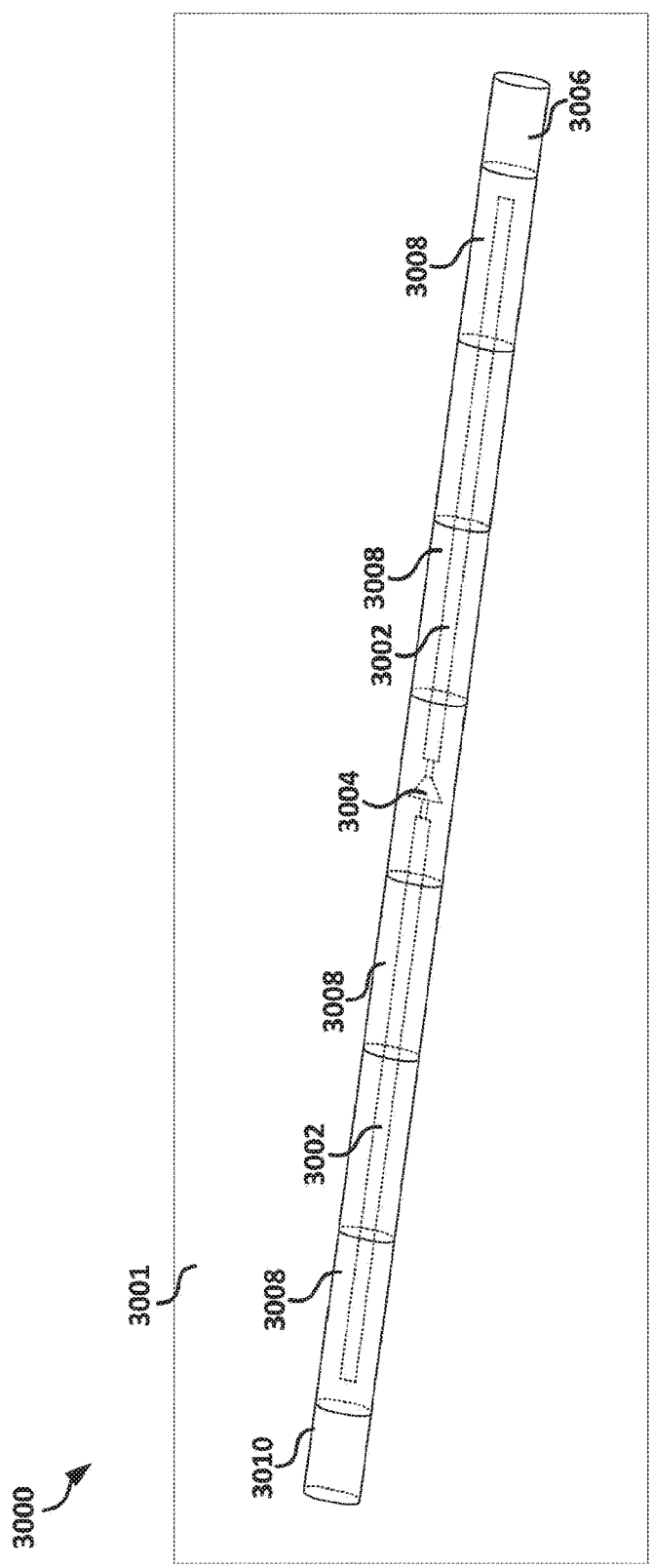
FIG. 29 shows a receiver device implanted in tissue.

FIG. 29 shows an implantable apparatus 3000 implanted in tissue 3001. The implantable apparatus 3000 as illustrated includes a dipole antenna 3002 and receiver 3004 encapsulated in a material 3006 and an outer implant casing 3010. The implantable apparatus 3000 also includes optional surface electrodes 3008 on the outer implant casing 3010. The surface electrodes 3008 are optional. For example, when the apparatus 3000 is being used as an ablation device, the surface electrodes 3008 transfer received energy to the tissue 3001. However, in an application in which the receiver is used to help provide power for electronics within an implanted device, for example an implanted sensor, the electrodes 3008 may not be needed.

The dipole antenna 3002 is made of a conductive material, such as a metal, semiconductor, polymer, or other conductive material. The dipole antenna 3002 can include two straight, thin conductors as shown in FIG. 29, or can include other dipole antenna shapes, such as a folded dipole, short dipole, cage dipole, bow-tie dipole, or batwing dipole. Using a shape other than the straight dipole will generally increase the width (e.g., diameter) of the apparatus 3000 relative to the diameter of the apparatus that includes a straight, thin dipole.

The receiver 3004 can be any receiver capable of receiving a signal from a midfield coupler. In one or more embodiments, the receiver can be an ultra-high frequency (UHF) receiver, such as is capable of receiving signals transmitted at a frequency of about 2.45 GHz. The wavelength of such signals in air is about 12.25 centimeters.

The material 3006 can be a high dielectric, low loss material, for example, PREPERM®, polytetrafluoroethylene (PTFE), such as a high dielectric PTFE, an Eccostock® material, or RT/Duroid®. The material 3006 can have a dielectric permittivity between the dielectric permittivity of the midfield coupler substrate 1312 (see FIG. 13) and the dielectric permittivity of the tissue 3001 in which the material 3006 is implanted. Such a configuration can allow for a larger receiver than would be allowed by a purely tissue loaded receiver, because one or more receiver dimensions are generally proportional to a wavelength of the signal incident thereon. A purely tissue coupled receiver is thus small as compared to a receiver that includes a dielectric with a permittivity between the dielectric permittivity of the midfield coupler substrate 1312 and the dielectric permittivity of the tissue 3001 in which the material 3006 is implanted. This in turn can increase efficiency of the power transmission link.

Consider an implantable receiver coupled to a small antenna encapsulated in a low dielectric material. The receiver is implanted in tissue that has a large dielectric permittivity relative to the low dielectric permittivity encapsulant. A large power loss is realized between the high dielectric tissue and the low dielectric encapsulant. To reduce this loss, the material 3106 can have a dielectric permittivity closer to that of the surrounding tissue, such as to better match the perceived impedances of the tissue and the encapsulant. In general, when using a higher dielectric material as an encapsulant, the receiver circuit has a smaller perceived impedance change than when using a lower dielectric material as an encapsulant. In other words, assume the impedance of the receiver in air is "d1" and the impedance of the receiver in tissue is "d2". Assume also, that the impedance difference, |d2−d1|=delta1 for the high impedance encapsulant and |d2−d1|=delta2 for the low impedance encapsulant. Generally, delta2>delta1. The smaller impedance change allows the dynamic range of an adaptive impedance matching network (e.g., a programmable inductor and/or programmable capacitor) at the interface of the receiver to be reduced. Another advantage of using an encapsulant with a higher dielectric permittivity includes the receiver being less sensitive to changes in surrounding tissue dielectric properties, which may occur due to scar tissue or adipose tissue formation.

The electrodes 3008 are optional and are electrically conductive elements that are electrically coupled to the receiver 3004. The electrodes 3008 transfer energy (electrical field energy) received at the receiver 3004 to the tissue 3001 in contact with the electrodes 3008, such as to ablate the tissue 3001.

The outer implant casing 3010 encloses the dipole antenna 3002, the receiver 3004, and the encapsulant material 3006. In one or more embodiments, the outer implant casing 3010 can be made of polyurethane, silicone, ceramics, other urethane blends, Tecothane®, Polyether ether ketone (PEEK), Pebax®, nylon, polycarbonate, Acrylonitrile butadiene styrene (ABS), thermoplastic, epoxy, combinations thereof, or the like.

Phase and/or Amplitude Adjustment for Transmitter

Previous solutions to help focus energy on an implanted receiver include a power detector integrated into the implant, as previously described. When using a time domain multiplexing communication system between an external transmitter and an implanted receiver, the phase and amplitude can be dynamically adjusted to help focus energy (e.g., more efficiently focus energy) at the implanted receiver without using a power detector at the implant.

Figure 30:
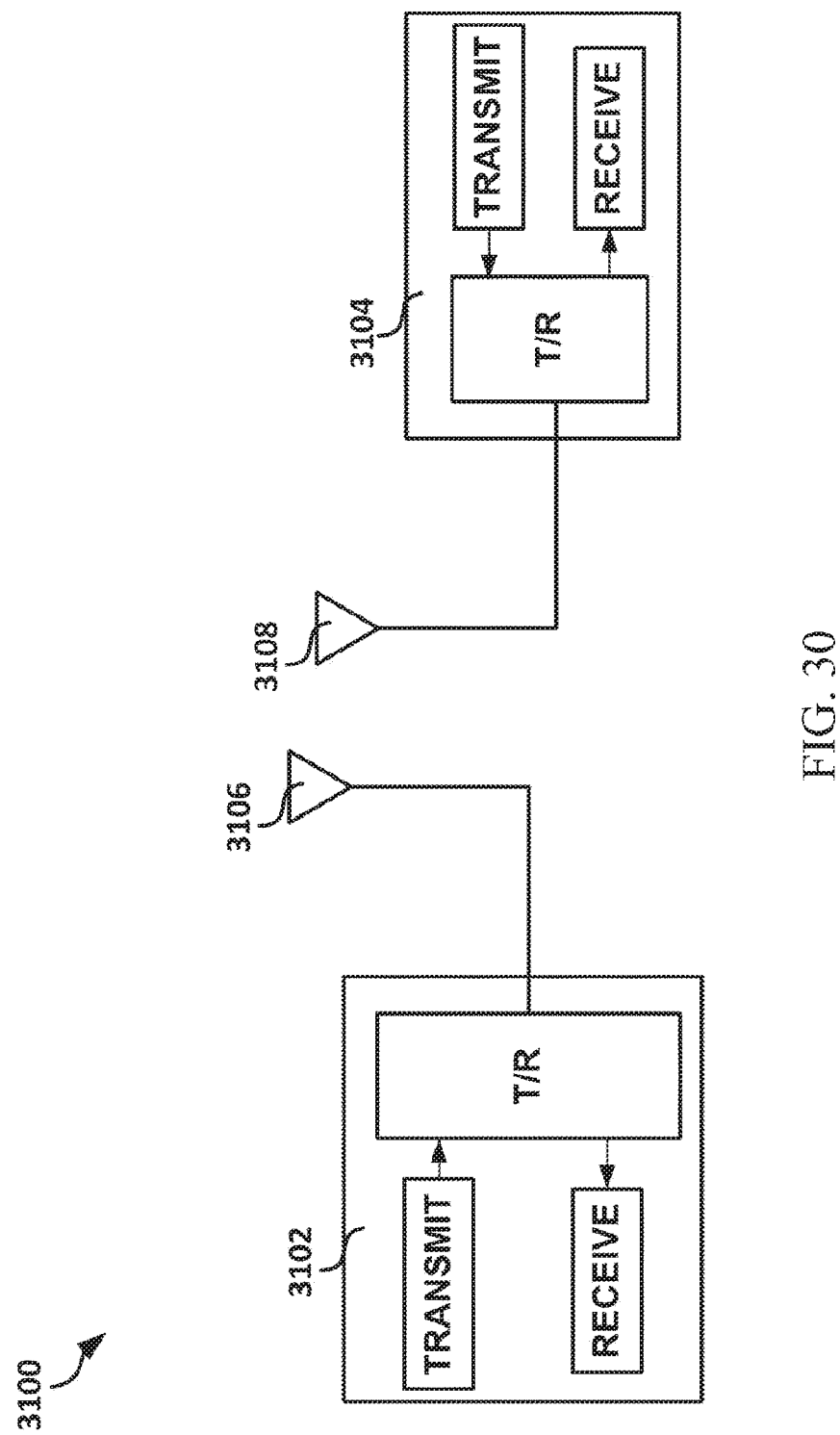
FIG. 30 shows a time domain multiplexed communication system.

FIG. 30 shows a time domain multiplexed communication system 3100. The system 3100 as illustrated includes an external midfield transceiver 3102 and an implantable transceiver 3104. The transceiver 3102 includes a communicatively coupled midfield antenna 3106 and the transceiver 3104 includes a communicatively coupled electric field based antenna 3108. The antennas 3106 and 3108 can be configured (e.g., in length, width, shape, material, etc.) to transmit and receive signals at the same frequency. The transceiver 3104 can transmit data signals through the antenna 3108 to the transceiver 3102 and can receive power and data signals transmitted by the transceiver 3102 through the antenna 3106.

The external midfield coupler (external transmitter) and implant transceiver (that includes the implant antenna) can be used for both transmission and reception of RF signals. T/R switches can be used to switch each RF port of the external transmitter from transmit (transmit data or power) to receive (receive data) mode (see FIG. 31). A T/R switch can be used to switch the implant between transmit (data transmission mode) and receive (power or data receive) mode (see FIG. 31).

Figure 31:
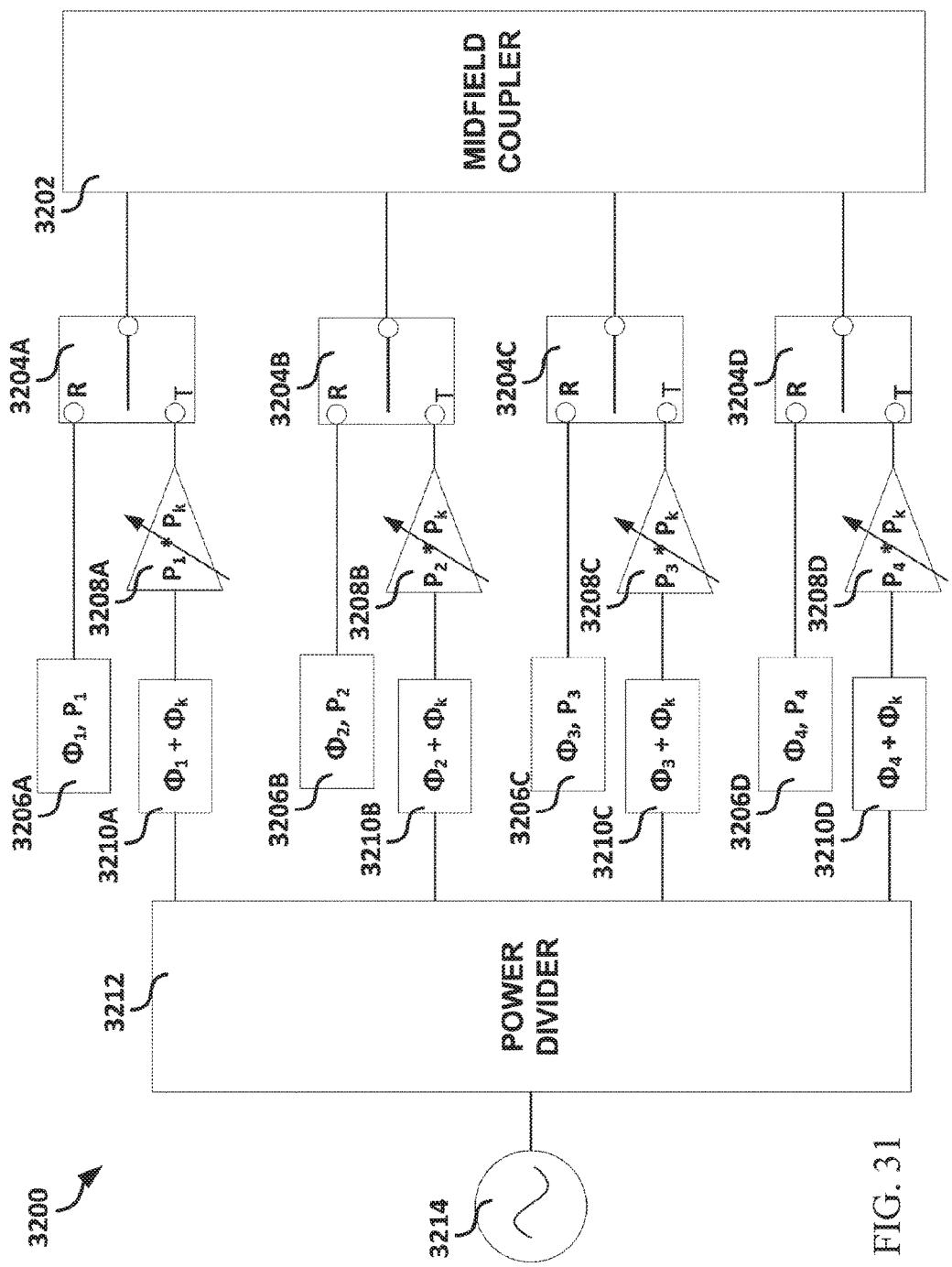
FIG. 31 shows an amplitude and phase shifting network.

The output of the receive terminal (on the external transmitter) of the T/R switch can be connected to one or more components that detect the phase and/or amplitude of the received signal from the implant. This phase and amplitude information can be used to program the phase of the transmit signal to be substantially the same relative phase as the received signal. To help achieve this, the transceiver 3102 can include a phase and amplitude matching network 3200, such as is shown in FIG. 31. The network 3200 is for use with a midfield coupler that includes four ports, such as the midfield coupler 602 of FIG. 6C. The network 3200 as illustrated includes a midfield coupler 3202 electrically coupled to a plurality of switches 3204A, 3204B, 3204C, and 3204D. The switches 3204A-D are each electrically coupled to a phase and/or amplitude detector 3206A, 3206B, 3206C, and 3206D, and a variable gain amplifier 3208A, 3208B, 3208C, and 3208D, respectively. The amplifier 3208A-D is electrically coupled to a phase shifter 3210A, 3210B, 3210C, and 3210D, respectively and the phase shifter 3210A-D is electrically coupled to a power divider 3212 that receives an RF input signal 3214 to be transmitted through the midfield coupler 3202.

The midfield coupler 3202 can be any midfield coupler discussed herein. The switch 3204A-D can be a selector switch that selects either the receive line ("R") or the transmit line ("T"). The number of switches 3204A-D of the network 3200 can be equal to the number of ports of the midfield coupler 3202. In the example of the network 3200 the midfield coupler 3202 has four ports, however any number of ports (and switches), one or more, can be used. In the example of a midfield coupler with a single port, the power divider 3212 is superfluous.

The phase and/or amplitude detector 3206A-D detects the phase ($\phi_1$, $\phi_2$, $\phi_3$, $\phi_4$) and power ($P_1$, $P_2$, $P_3$, $P_4$) of a signal received at each port of the midfield coupler 3202. The phase and/or amplitude detector 3206A-D can be implemented in one or more modules (hardware modules that can include electric or electronic components arranged to perform an operation, such as determining a phase or amplitude of a signal), such can include a phase detector module and/or an amplitude detector module. The detector 3206A-D can include analog and/or digital components arranged to determine the phase and/or amplitude of a signal received at the midfield detector 3202.

The amplifier 3208A-D can receive an input (e.g., M) from the phase shifter 3210A-D (e.g., $P_k$ phase shifted by $\Phi_1+\Phi_k$, $\Phi_2+\Phi_k$, $\Phi_3+\Phi_k$, or $\Phi_4+\Phi_k$). The output of the amplifier, O, is generally the output of the power divider, M when the RF signal 3214 has an amplitude of 4*M in the example of FIG. 31, multiplied by the gain of the amplifier $P_i*P_k$. $P_k$ can be set dynamically as the values for $P_1$, $P_2$, $P_3$, and/or $P_4$ change. $\Phi_k$ is a constant. The phase shifter 3210A-D sets the relative phases of the ports based on the phase from the detector 3206A-D.

Consider a situation in which the transmit power required to be transmitted from the midfield coupler 3202 is $P_{tt}$. The RF signal provided to the power divider 3212 has a power of 4*M. The output of the amplifier 3208A is generally $M*P_1*P_k$. Thus, the power transmitted from the midfield coupler is $M*(P_1*P_k+P_2*P_k+P_3*P_k+P_4*P_k)=P_{tt}$. Solving for $P_k$ yields $P_k=P_{tt}/(M*(P_1+P_2+P_3+P_4))$.

The amplitude of a signal at each RF port can be transmitted with the same relative (scaled) amplitude as the signal received at the respective port of the midfield coupler coupled thereto. The gain of the amplifier 3208A-D can be further refined to account for a loss between the transmission and reception of the signal from the midfield coupler. Consider a reception efficiency of $\eta=P_{ir}/P_{tt}$, where $P_{ir}$ is the power received at the implanted receiver. An efficiency (e.g., a maximum efficiency), given a phase and amplitude tuning, can be estimated from the amplitude received from the transmitter of the implant at the external midfield coupler. This estimation can be given as $\eta \approx (P_1+P_2+P_3+P_4)/P_{it}$, where $P_{it}$ is the original power of the signal from the implanted transmitter. The power of the signal from the implanted transmitter can be communicated to the external transceiver 3102 as data from the implanted transceiver 3104. The amplitude of a signal received at an amplifier 3108A-D can be scaled according to the determined efficiency to help ensure that the implant receives power to perform the programmed operation(s). Given the estimated link efficiency, $\eta$, and an implant power (e.g., amplitude) requirement of $P_{ir}'$, $P_k$ can be scaled as $P_k=P_{ir}'/[\eta(P_1+P_2+P_3+P_4)]$ to help ensure that the implant receives adequate power to perform the programmed functions.

The control signals for the phase shifter 3210A-D and the amplifier 3208A, such as the phase input and gain input, respectively, can be provided by processing circuitry that is not shown in FIG. 31. The circuitry is omitted so as to not overly complicate or obscure the view provided in FIG. 31. The same or different processing circuitry can be used to change the switch 3204A-D from the receive line to the transmit line and vice versa. Again, this processing circuitry is not shown in FIG. 31 so as to not overly complicate or obscure the view provided in FIG. 31. See control unit 2112 of FIG. 21A for an example of such processing circuitry.

Customizing Midfield Coupler Dimension(s)

Every body is different in terms of structure (e.g., tissue, muscle density, fat content, cartilage, scar tissue, tendon makeup, or other structure properties, such as bone), contour, and/or shape. Different midfield coupler shapes can provide a variety of characteristics that help to more efficiently accommodate power transfer to receivers in such bodies and/or fit comfortably on the external surface (e.g., the skin, such as an epidermal layer) of the body. A midfield coupler with a first shape may be more efficient at delivering power to a first body, but less efficient at delivering power to a second body.

Figure 32:
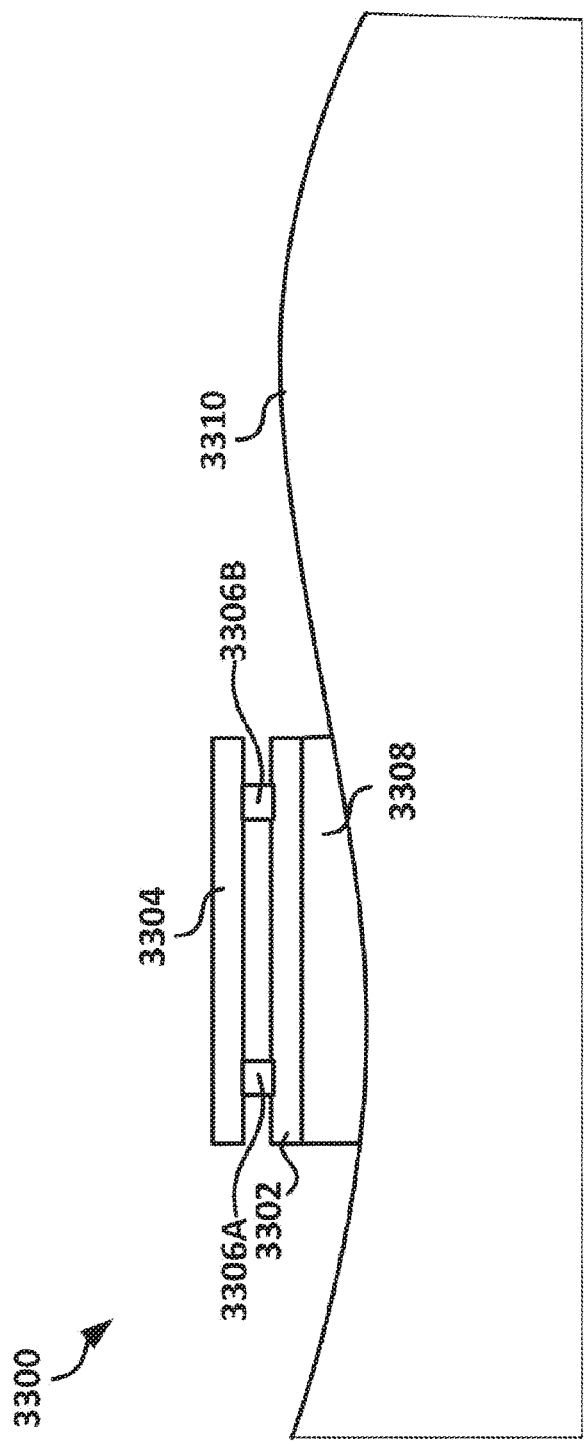
FIG. 32 shows a midfield coupler attached to tissue.

FIG. 32 shows a midfield coupler attached to tissue (e.g., human or other animal skin). The midfield coupler system 3300 as illustrated includes a midfield coupler 3302, an electronics module 3304, RF connectors 3306A and 3306B, and a molded backing layer 3308. The system 3300 is shown attached to tissue 3310.

Figure 33:
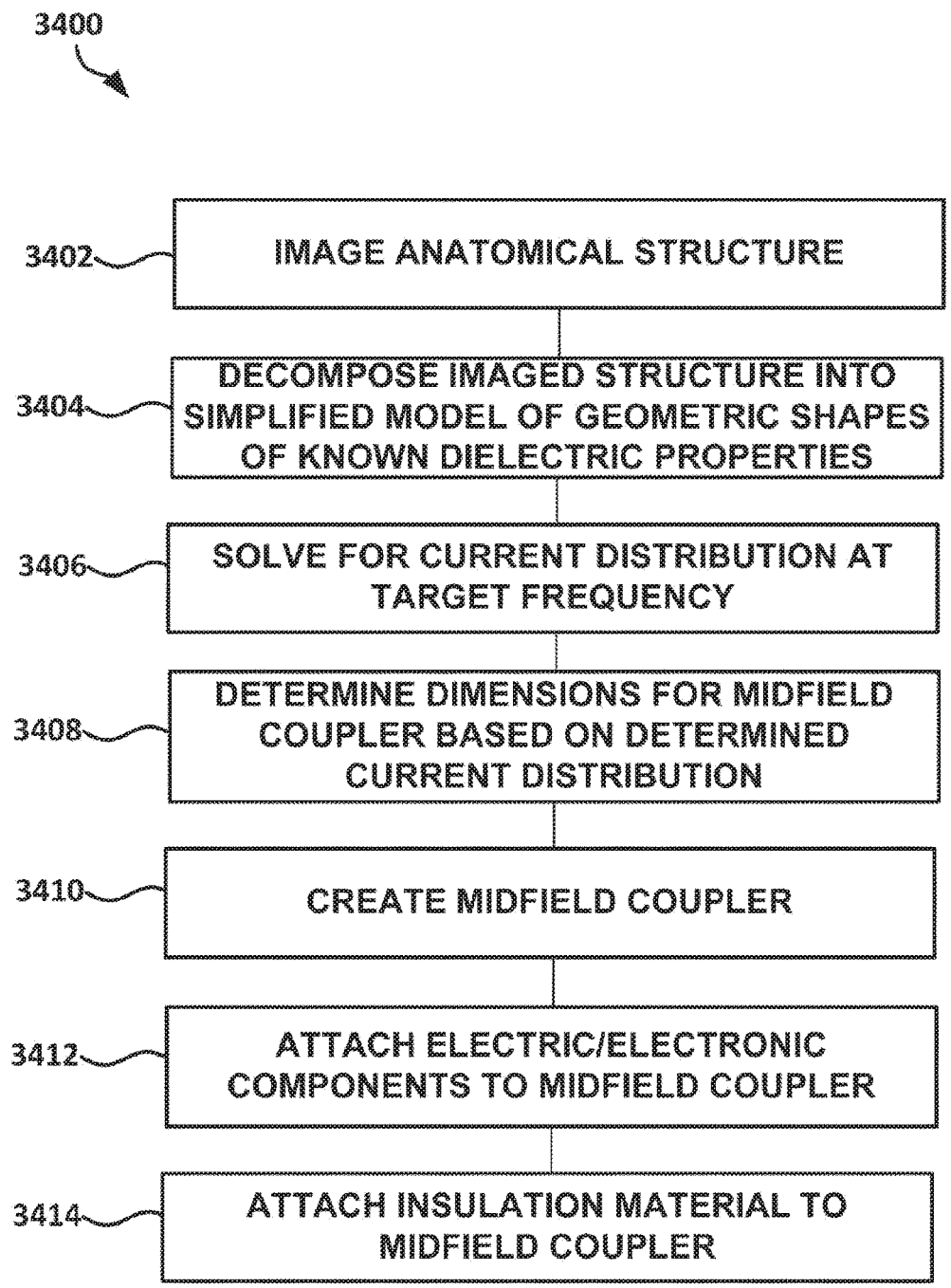
FIG. 33 shows a method for customizing a midfield coupler.

The operations shown in FIG. 33 show a method of designing a midfield coupler to accommodate a specific body shape, contour, and/or structure. This procedure allows for design of a focused midfield transmitter for efficiently powering or otherwise providing energy to an anatomical structure, such as when a high field intensity is required to power more power hungry electronics or perform an ablation at a target region, and when the implant is implanted deeper than the near field, such as in the mid-field.

At operation 3402, an anatomical structure (e.g., the structure 3310) can be imaged, such as by using Magnetic Resonance Imaging (MRI) device, a Computed Tomography (CT) device, or other imaging device. The anatomical structure includes the area at which the implant is to be situated. At operation 3404, the imaged structure can be decomposed into a simplified model of geometric shapes of materials (e.g., tissue, bone, tendon, cartilage, scar tissue, organs, fluids, and/or vessels, etc.) with known dielectric properties. At operation 3406, a current distribution at a target frequency (e.g., 915 MHz, 2.45 GHz, or other microwave frequency) is determined. At operation 3408 dimensions of a midfield coupler (e.g., width/length of strip, slot width/length, spacing between slot(s), value of one or more passive components (e.g., programmable passive components, such as a capacitor or inductor), such as can be used for impedance matching, or ports of midfield source, such as the midfield coupler 3302) that can provide energy at or near the determined current distribution are determined. Not all current distributions may be possible, so it may be necessary to choose a different implantation site, or to operate the midfield coupler at less than optimal efficiency. The current distribution can be determined by solving a current distribution equation previously discussed.

At operation 3410 a customized midfield plate of a midfield coupler can be created (e.g., etched, plated, and/or printed). The plate can be created by using a standard fabrication technique and or materials, such as can include FR4, polyimide, or other material. At operation 3412, electric/electronic components can be electrically coupled to the midfield coupler. The components can include one or more connectors, such as the RF connectors 3306A-B, electric/electronics module 3304 (e.g., one or more transistors, resistors, capacitors, transceivers (e.g., transmit and receive radio and antenna), inductors, digital logic, such as logic gates (e.g., programmable logic gates), an Arithmetic Logic Unit (ALU), a processor, or the like). The electric/electronic module 3304 can include the switches 3204A-D, detector 3206A-D, the amplifier 3208A-D, the phase shifter 3210A-D, and/or the power divider 3212.

At operation 3414, an insulation material, such as the material 3308, can be attached to the midfield coupler 3302. The insulation material can include foam, polymer (e.g., plastic), or silicone. The material 3308 can be attached to the surface of the midfield coupler 3302 to provide an insulation layer between the midfield coupler and the tissue 3310. The material 3308 can be molded, cut, or 3D printed to conform to the shape of the skin surface. Imaging the contour of the surface can be done using a camera, laser, or cast. Conforming the material to the tissue 3310 can increase the comfort of the patient while wearing the transmitter and minimizing slipping or displacement of the transmitter from the target anatomy. Minimizing slipping can be important for non-adjustable midfield couplers in which the focal region of the transmitter is fixed. Additional backing material may be added to provide a soft interface between skin and the midfield coupler unit.

More Applications

One or more of the systems, apparatuses, and methods discussed herein can be used to help treat fecal or urinary incontinence (e.g., overactive bladder), such as by stimulating the tibial nerve or any branch of the tibial nerve, such as but not limited to the posterior tibial nerve, one or more nerves or nerve branches originating from the sacral plexus, including but not limited to S1-S4, the tibial nerve, and/or the pudendal nerve. One or more of the systems, apparatuses, and methods discussed herein can be used to help treat urinary incontinence, such as overactive bladder. Urinary incontinence can be treated by using midfield wireless transfer by stimulating one or more of muscles of the pelvic floor, nerves innervating the muscles of the pelvic floor, internal urethral sphincter, external urethral sphincter, and the pudendal nerve or branches of the pudendal nerve.

One or more of the systems, apparatuses, and methods discussed herein can be used to help treat sleep apnea and/or snoring by stimulating one or more of a nerve or nerve branches of the hypoglossal nerve, the base of the tongue (muscle), phrenic nerve(s), intercostal nerve(s), accessory nerve(s), and cervical nerves C3-C6. Treating sleep apnea and/or snoring can include using a midfield coupler to provide energy to an implant to sense a decrease, impairment, or cessation of breathing (such as by measuring oxygen saturation).

One or more of the systems, apparatuses, and methods discussed herein can be used to help treat vaginal dryness, such as by stimulating one or more of bartholin gland(s), skene's gland(s), and inner wall of vagina. One or more of the systems, apparatuses, and methods discussed herein can be used to help treat a migraine, such as by stimulating one or more of the occipital nerve, supraorbital nerve, C2 cervical nerve, or branches thereof, and the frontal nerve, or branches thereof. One or more of the systems, apparatuses, and methods discussed herein can be used to help treat post-traumatic stress disorder, hot flashes, and/or complex regional pain syndrome such as by stimulating one or more of the stellate ganglion and the C4-C7 of the sympathetic chain.

One or more of the systems, apparatuses, and methods discussed herein can be used to help treat trigeminal neuralgia, such as by stimulating one or more of the sphenopalatine ganglion nerve block, the trigeminal nerve, or branches of the trigeminal nerve. One or more of the systems, apparatuses, and methods discussed herein can be used to help treat dry mouth (e.g., caused by side effects from medications, chemotherapy or radiation therapy cancer treatments, Sjogren's disease, or by other cause of dry mouth), such as by stimulating one or more of Parotid glands, submandibular glands, sublingual glands, submucosa of the oral mucosa in the oral cavity within the tissue of the buccal, labial, and/or lingual mucosa, the soft palate, the lateral parts of the hard palate, and/or the floor of the mouth and/or between muscle fibers of the tongue, Von Ebner glands, glossopharyngeal nerve (CN IX), including branches of CN IX, including otic ganglion, a facial nerve (CN VII), including branches of CN VII, such as the submandibular ganglion, and branches of T1-T3, such as the superior cervical ganglion.

One or more of the systems, apparatuses, and methods discussed herein can be used to help treat a transected nerve, such as by sensing electrical output from the proximal portion of a transected nerve and delivering electrical input into the distal portion of a transected nerve, and/or sensing electrical output from the distal portion of a transected nerve and delivering electrical input into the proximal portion of a transected nerve. One or more of the systems, apparatuses, and methods discussed herein can be used to help treat cerebral palsy, such as by stimulating one or more muscles or one or more nerves innervation one or more muscles affected in a patient with cerebral palsy. One or more of the systems, apparatuses, and methods discussed herein can be used to help treat erectile dysfunction, such as by stimulating one or more of pelvic splanchnic nerves (S2-S4) or any branches thereof, the pudendal nerve, cavernous nerve(s), and inferior hypogastric plexus.

One or more of the systems, apparatuses, and methods discussed herein can be used to help treat menstrual pain, such as by stimulating one or more of the uterus and the vagina. One or more of the systems, apparatuses, and methods discussed herein can be used as an intrauterine device, such as by sensing one or more PH and blood flow or delivering current or drugs to aid in contraception, fertility, bleeding, or pain. One or more of the systems, apparatuses, and methods discussed herein can be used to incite human arousal, such as by stimulating female genitalia, including external and internal, including clitoris or other sensory active parts of the female, or by stimulating male genitalia. One or more of the systems, apparatuses, and methods discussed herein can be used to help treat hypertension, such as by stimulating one or more of a carotid sinus, vagus nerve, or a branch of the vagus nerve. One or more of the systems, apparatuses, and methods discussed herein can be used to help treat paroxysmal supraventricular tachycardia, such as by stimulating one or more of trigeminal nerve or branches thereof, anterior ethmoidal nerve, and the vagus nerve.

One or more of the systems, apparatuses, and methods discussed herein can be used to help treat vocal cord dysfunction, such as by sensing the activity of a vocal cord and the opposite vocal cord or just stimulating one or more of the vocal cords by stimulating nerves innervating the vocal cord, the left and/or Right recurrent laryngeal nerve, and the vagus nerve. One or more of the systems, apparatuses, and methods discussed herein can be used to help repair tissue, such as by stimulating tissue to do one or more of enhancing microcirculation and protein synthesis to heal wounds and restoring integrity of connective and/or dermal tissues. One or more of the systems, apparatuses, and methods discussed herein can be used to help asthma or chronic obstructive pulmonary disease, such as by one or more of stimulating the vagus nerve or a branch thereof, blocking the release of norepinephrine and/or acetylcholine and/or interfering with receptors for norepinephrine and/or acetylcholine. One or more of the systems, apparatuses, and methods discussed herein can be used to help treat cancer, such as by stimulating, to modulate one or more nerves near or in a tumor, such as to decrease the sympathetic innervation, such as epinephrine/NE release, and/or parasympathetic innervation, such as Ach. One or more of the systems, apparatuses, and methods discussed herein can be used to help treat diabetes, such as by powering a sensor inside the human body that detects parameters of diabetes, such as a glucose level or ketone level and using such sensor data to adjust delivery of exogenous insulin from an insulin pump. One or more of the systems, apparatuses, and methods discussed herein can be used to help treat diabetes, such as by powering a sensor inside the human body that detects parameters of diabetes, such as a glucose level or ketone level, and using a midfield coupler to stimulate the release of insulin from islet beta cells.

Additional Examples

Example 1 can include or use subject matter (such as an apparatus, a method, a means for performing operations, or a machine readable memory including instructions that, when performed by the machine, can configure the machine to perform acts), such as can include or use a first transceiver that transmits and receives microwave signals at a first frequency, the first transceiver including a midfield coupler that converts signals from the first transceiver to signals with a non-negligible H-field component parallel to a surface of the midfield coupler and focuses the converted signals to a location within tissue that is within a wavelength, as measured in air, of the microwave signals; and an at least partially implantable biocompatible device comprising a second transceiver, the second transceiver including an E-field based antenna that receives the signals from the midfield coupler and the second transceiver transmits signals at about the same frequency as the first transceiver.

Example 2 can include or use, or can optionally be combined with the subject matter of Example 1, to include or use, wherein the E-field based antenna is a dipole antenna.

Example 3 can include or use, or can optionally be combined with the subject matter of at least one of Examples 1-2, to include or use, wherein the first transceiver comprises a phase matching network comprising a phase detector and a phase shifter, the phase detector and the phase shifter electrically coupled to the midfield coupler, the phase detector determines a phase of a signal received from the second transceiver, and the phase shifter adjusts a phase of a signal to be provided to the midfield coupler based on the determined phase of the signal received from the second transceiver.

Example 4 can include or use, or can optionally be combined with the subject matter of Example 3, to include or use, wherein the phase shifter adjusts the phase of the signal by the determined phase of the signal received from the second transceiver.

Example 5 can include or use, or can optionally be combined with the subject matter of Example 3, to include or use, wherein the phase shifter adjusts the phase of the signal to match the phase of the signal received from the second transceiver.

Example 6 can include or use, or can optionally be combined with the subject matter of at least one of Examples 1-5, to include or use, wherein the first transceiver comprises an amplitude matching network comprising an amplitude detector and a variable gain amplifier electrically coupled to the midfield coupler, the amplitude detector determines an amplitude of a signal received from the second transceiver and the variable gain amplifier adjusts an amplitude of a signal to be provided to the midfield coupler based on the amplitude of the signal received from the second transceiver.

Example 7 can include or use, or can optionally be combined with the subject matter of Example 6, to include or use, wherein the midfield coupler includes two or more ports, the amplitude detector is one of two or more amplitude detectors, each amplitude detector of the two or more amplitude detectors electrically coupled to a respective port of the midfield coupler, the first transceiver further comprises a power divider which receives a radio frequency (RF) signal and divides and separates the RF signal into two or more signals, one signal for each port of the midfield coupler, and wherein the variable gain amplifier is one of a plurality of variable gain amplifiers, each variable gain amplifier is electrically coupled between a respective port of the midfield coupler and the power divider, each amplifier receives a signal of the two or more signals from the power divider and amplifies the signal by a gain, wherein the gain is determined based on an amplitude determined by the amplitude detector coupled to the same respective of the midfield coupler.

Example 8 can include or use, or can optionally be combined with the subject matter of Example 7, to include or use, wherein the gain of each amplifier of the plurality of amplifiers is the amplitude determined by the amplitude detector multiplied by a quantity.

Example 9 can include or use, or can optionally be combined with the subject matter of Example 8, to include or use, wherein the quantity is $$P_k = P_{tt} \bigg/ \sum_{i=1}^{N} P_i,$$

where $P_{tt}$ is a specified amplitude and $P_i$ is an amplitude of the plurality of amplitudes determined at the amplitude detector for each of the i ports of the midfield coupler.

Example 10 can include or use, or can optionally be combined with the subject matter of Example 9, to include or use, wherein the quantity, Pk, is further divided by an efficiency indicator, $\eta$, where $\eta = \Sigma_{i=1}^{N} P_i / P_{it}$ where $P_{it}$ is an amplitude of a signal transmitted from the second transceiver.

Example 11 can include or use, or can optionally be combined with the subject matter of at least one of Examples 1-10, to include or use, wherein the antenna is encapsulated in a dielectric material with a dielectric permittivity between a dielectric permittivity of animal tissue and a dielectric permittivity of a substrate of the midfield coupler on which a midfield plate of the midfield coupler is arranged.

Example 12 can include or use subject matter (such as an apparatus, a method, a means for performing operations, or a machine readable memory including instructions that, when performed by the machine, can configure the machine to perform acts), such as can include or use a radio that transmits and receives microwave signals, a midfield coupler electrically coupled to the radio, the midfield coupler converts signals from the radio to signals with a non-negligible H-field component parallel to a surface of the midfield coupler and focuses the signals to a location within tissue within a wavelength of the microwave signals as measured in air, an amplitude detector electrically coupled to the midfield coupler, the amplitude detector determines an amplitude of a signal received at the midfield coupler, and a variable gain amplifier electrically coupled between the radio and the midfield coupler, the amplifier to amplify a transmit signal from the radio in proportion to the amplitude determined by the amplitude detector.

Example 13 can include or use, or can optionally be combined with the subject matter of Example 12, to include or use a phase matching network comprising a phase detector and a phase shifter, the phase shifter and the phase detector electrically coupled to the midfield coupler, the phase detector determines a phase of a signal received at the midfield coupler and the phase shifter adjusts a phase of a signal provided to the midfield coupler based on the determined phase.

Example 14 can include or use, or can optionally be combined with the subject matter of Example 13, to include or use, wherein the phase shifter adjusts the phase of the signal by the determined phase.

Example 15 can include or use, or can optionally be combined with the subject matter of at least one of Examples 12-14, to include or use, wherein the midfield coupler includes two or more ports, the amplitude detector is one of two or more amplitude detectors, each amplitude detector of the two or more amplitude detectors electrically coupled to a respective port of the midfield coupler, the first transceiver further comprises a power divider which receives a radio frequency (RF) signal and divides and separates the RF signal into two or more signals, one signal for each port of the midfield coupler, and wherein the variable gain amplifier is one of a plurality of variable gain amplifiers, each variable gain amplifier is electrically coupled between a respective port of the midfield coupler and the power divider, each amplifier receives a signal of the two or more signals from the power divider and amplifies the signal by a gain, wherein the gain is determined based on an amplitude determined by the amplitude detector.

Example 16 can include or use, or can optionally be combined with the subject matter of Example 15, to include or use, wherein the gain of each amplifier of the plurality of amplifiers is the amplitude determined by the amplitude detector multiplied by a quantity.

Example 17 can include or use, or can optionally be combined with the subject matter of Example 16, to include or use, wherein the quantity is $$P_k = P_{tt} \bigg/ \left( \eta * \left( \sum_{i=1}^{N} P_i \right) \right),$$

where $P_{tt}$ is a specified amplitude, $P_i$ is an amplitude of the plurality of amplitudes determined at the amplitude detector for each of the i ports of the midfield coupler and $\eta = \Sigma_{i=1}^{N} P_i / P_{it}$ where $P_{it}$ is an amplitude of a signal transmitted to the midfield coupler.

Example 18 can include or use subject matter (such as an apparatus, a method, a means for performing operations, or a machine readable memory including instructions that, when performed by the machine, can configure the machine to perform acts), such as can include or use an at least partially implantable, biocompatible apparatus comprising, an outer casing, a radio that transmits and receives microwave signals encased by the outer casing, an electric field based antenna electrically coupled to the radio and encased by the outer casing, and an encapsulant within the outer casing, the encapsulant surrounding the radio and the antenna and the encapsulant including a dielectric permittivity between a dielectric permittivity of animal tissue and a dielectric permittivity of a substrate of a midfield coupler.

Example 19 can include or use, or can optionally be combined with the subject matter of Example 18, to include or use, wherein the antenna is a dipole antenna.

Example 20 can include or use, or can optionally be combined with the subject matter of at least one of Examples 18-19, to include or use, one or more electrodes exposed on the outer casing and electrically coupled to the radio.

What is claimed is:

1. A system comprising:
a first transceiver that transmits and receives microwave signals at a first frequency, the first transceiver including a midfield coupler that converts signals from the first transceiver to signals with a non-negligible H-field component parallel to a surface of the midfield coupler and focuses the converted signals to a location within tissue that is within a wavelength, as measured in air, of the microwave signals; and
an at least partially implantable biocompatible device comprising a second transceiver, the second transceiver including an E-field based antenna that receives the signals from the midfield coupler and the second transceiver transmits signals at about the same frequency as the first transceiver.

2. The system of claim 1, wherein the E-field based antenna is a dipole antenna.

3. The system of claim 1, wherein the first transceiver comprises:
a phase matching network comprising a phase detector and a phase shifter, the phase detector and the phase shifter electrically coupled to the midfield coupler, the phase detector determines a phase of a signal received from the second transceiver, and the phase shifter adjusts a phase of a signal to be provided to the midfield coupler based on the determined phase of the signal received from the second transceiver.

4. The system of claim 3, wherein the phase shifter adjusts the phase of the signal by the determined phase of the signal received from the second transceiver.

5. The system of claim 3, wherein the phase shifter adjusts the phase of the signal to match the phase of the signal received from the second transceiver.

6. The system of claim 1, wherein the first transceiver comprises:
an amplitude matching network comprising an amplitude detector and a variable gain amplifier electrically coupled to the midfield coupler, the amplitude detector determines an amplitude of a signal received from the second transceiver and the variable gain amplifier adjusts an amplitude of a signal to be provided to the midfield coupler based on the amplitude of the signal received from the second transceiver.

7. The system of claim 6, wherein:
the midfield coupler includes two or more ports,
the amplitude detector is one of two or more amplitude detectors, each amplitude detector of the two or more amplitude detectors electrically coupled to a respective port of the midfield coupler,
the first transceiver further comprises a power divider which receives a radio frequency (RF) signal and divides and separates the RF signal into two or more signals, one signal for each port of the midfield coupler, and
wherein the variable gain amplifier is one of a plurality of variable gain amplifiers, each variable gain amplifier is electrically coupled between a respective port of the midfield coupler and the power divider, each amplifier receives a signal of the two or more signals from the power divider and amplifies the signal by a gain, wherein the gain is determined based on an amplitude determined by the amplitude detector coupled to the same respective of the midfield coupler.

8. The system of claim 7, wherein the gain of each amplifier of the plurality of amplifiers is the amplitude determined by the amplitude detector multiplied by a quantity.

9. The system of claim 8, wherein the quantity is $P_k = P_{tt}/\Sigma_{i=1}^{N} P_i$, where $P_{tt}$ is a specified amplitude and $P_i$ is an amplitude of the plurality of amplitudes determined at the amplitude detector for each of the i ports of the midfield coupler.

10. The system of claim 9, wherein the quantity, Pk, is further divided by an efficiency indicator, $\eta$, where $\eta = \Sigma_{i=1}^{N} P_i/P_{tt}$ where $P_{tt}$ is an amplitude of a signal transmitted from the second transceiver.

11. The system of claim 1, wherein the antenna is encapsulated in a dielectric material with a dielectric permittivity between a dielectric permittivity of animal tissue and a dielectric permittivity of a substrate of the midfield coupler on which a midfield plate of the midfield coupler is arranged.

* * * * *